(12) United States Patent
Ogiwara et al.

(10) Patent No.: US 8,013,137 B2
(45) Date of Patent: Sep. 6, 2011

(54) MODIFIED ENTEROPEPTIDASE PROTEIN

(75) Inventors: Katsueki Ogiwara, Hokkaido (JP); Takayuki Takahashi, Hokkaido (JP)

(73) Assignee: National University Corporation Hokkaido University, Hokkaido (JP)

( * ) Notice: Subject to any disclaimer, the term of this patent is extended or adjusted under 35 U.S.C. 154(b) by 976 days.

(21) Appl. No.: 11/973,157

(22) Filed: Oct. 4, 2007

(65) Prior Publication Data

US 2008/0213836 A1 Sep. 4, 2008

Related U.S. Application Data

(60) Provisional application No. 60/852,454, filed on Oct. 17, 2006.

(51) Int. Cl.
- C12N 15/57 (2006.01)
- C12N 15/70 (2006.01)
- C12N 9/50 (2006.01)
- C12N 9/64 (2006.01)
- C12N 15/52 (2006.01)
- C12N 15/74 (2006.01)
- C12N 15/79 (2006.01)

(52) U.S. Cl. ...... 536/23.2; 435/69.1; 435/219; 435/226; 435/252.3; 435/252.33; 435/320.1; 435/810; 536/23.5

(58) Field of Classification Search .................. None
See application file for complete search history.

(56) References Cited

U.S. PATENT DOCUMENTS

| 6,444,644 B1 * | 9/2002 | Bruckdorfer et al. ........... 514/12 |
| 2002/0164588 A1 * | 11/2002 | Eisenberg et al. ................ 435/6 |
| 2003/0167477 A1 * | 9/2003 | Cottingham et al. ............. 800/7 |

FOREIGN PATENT DOCUMENTS

| JP | 2005-253325 A | * | 9/2005 |
| JP | 20052533325 A1 | | 9/2005 |

OTHER PUBLICATIONS

Kimura, A., et al., 1999, "Structure and Localization of the Mouse Prolyl Oligopeptidase Gene", The Journal of Biological Chemistry, vol. 274, No. 34, pp. 24047-24053.*
Novagen Catalogue, 2004/2005, "Site-Specific Proteases and Cleavage Capture Kits/Recombinant Enterokinase", p. 301.*
Rajapakse, S., et al., 2005, "Biochemical characterization of human kallikrein 8 and its possible involvement in the degradation of extracellular matrix proteins", FEBS letters, vol. 579, pp. 6879-6884.*
Ogiwara, K., et al., 2005, "Gelatinase A and membrane-type matrix metalloproteinases 1 and 2 are responsible for follicle rupture during ovulation in the medaka", Proceedings of the National Academy of Sciences, USA, vol. 202, No. 24, pp. 8442-8447.*

(Continued)

*Primary Examiner* — Nashaat Nashed
*Assistant Examiner* — William W Moore
(74) *Attorney, Agent, or Firm* — Peter F. Corless; Christine C. O'Day; Edwards Angell Palmer & Dodge LLP

(57) ABSTRACT

Disclosed are novel enteropeptidase polypeptides, polynucleotides encoding the polypeptides, nucleotide constructs, vectors, host cells comprising the polynucleotides, and methods for producing the polypeptides and polynucleotides. Such polypeptides are useful as protein engineering tool for enzymatic cleavage of fusion proteins. Also provided are kits comprising the polypeptides of the invention.

48 Claims, 21 Drawing Sheets

OTHER PUBLICATIONS

A. Light et al., "Enterokinase (enteropeptidase): comparative aspects", TIBS 14, pp. 110-112 (1989).

E.R. LaVallie et al. "Cloning and Functional Expression of a cDNA Encoding the Catalytic Subunit of Bovine Enterokinase", The Journal of Biological Chemistry, 268(31), pp. 23311-23317 (1993).

Y. Kitamoto et al., "Enterokinase, the initiator of intestinal digestion, is a mosaic protease composed of a distinctive assortment of domains", Proc. Natl. Acad. Sci. USA, vol. 91, pp. 7588-7592 (1994).

Y. Kitamoto et al., "cDNA Sequence and Chromosomal Localization of Human Enterokinase, the Proteolytic Activator of Trypsinogen", Biochemistry, vol. 34, pp. 4562-4568 (1995).

M. Matsushima et al., "Structural Characterization of Porcine Enteropeptidase", The Journal of Biological Chemistry, 269(31), pp. 19976-19982 (1994).

A.G. Mikhailova et al., "Autolysis of bovine enteropeptidase heavy chain: evidence of fragment 118-465 involvement in trypsinogen activation", FEBS Letters, vol. 442, pp. 226-230 (1999).

D. Lu et al., "Crystal Structure of Enteropeptidase Light Chain Complexed with an Analog of the Trypsinogen Activation Peptide", J. Mol. Biol., vol. 292, pp. 361-373 (1999).

X. Zheng et al., "Mucin-like Domain of Enteropeptidase Directs Apical Targeting in Mardin-Darby Canine Kidney Cells", The Journal of Biological Chemistry, 277(9), pp. 6858-6863 (2002).

S. Bricteux-Gregoire et al., "Phylogeny of Trypsinogen Activiation Peptides", Comp. Biochem. Physiol., vol. 42B, pp. 23-39 (1972).

N. Yahagi et al., "Complementary DNA Cloning and Sequencing of Rat Enteropeptidase and Tissue Distribution of Its mRNA", Biochemical and Biophysical Research Communications, vol. 219, pp. 806-812 (1996).

X. Yuan et al., "Structure of murine enterokinase (enteropeptidase) and expression in small intestine during development", Am. J. Phys. vol. 274, pp. G342-G349 (1998).

D. Lu et al., "Bovine Proenteropeptidase is Activated by Trypsin, and the Specificity of Enteropeptidase Depends on the Heavy Chain", The Journal of Biological Chemistry, 272(50), pp. 31293-31300 (1997).

L.A. Collins-Racie et al., "Production of Recombinant Bovine Enterokinase Catalytic Subunit in *Escherichia coli* Using the Novel Secretory Fusion Partner DsbA" Biotechnology, vol. 13, pp. 982-987 (1995).

F.A. Ghishan et al., "Isolated Congenital Enterokinase Deficiency", Gastroenterology, vol. 85, pp. 727-731 (1983).

\* cited by examiner

FIG. 1B

| | | 10 | | 20 | | 30 | | 40 | | 50 |
|---|---|---|---|---|---|---|---|---|---|---|
| Medaka | CGQRQ | VYNSKENNGV | PR | VGGVNA | EKGAWPWM | VSLHW | -RGR | ---- | -HGCGASLIGR |
| Human | CGKKL | LAAQ | DIT | ---- | PKIVGGS | NAKEGAWPWV | VGLYY | --GGR | ---- | -LLCGASLVSS |
| Mouse | CGEKK | VTQK | VS | ---- | PKIVGGS | DAQAGAWPWV | VALYH | -RDRSTDR | LLCGASLVSS |
| Bovine | CGKKL | VTQ | EVS | ---- | PKIVGGS | REGAWPWV | VALYF | -DDQ | ---- | -QVCGASLVSR |
| Porcine | CGKKQ | VAQ | EVS | ---- | PKIVGGN | DSREGAWPWV | VALYY | -NGQ | ---- | -LLCGASLVSR |
| Chymo | CGVPA | IQPVLSGLS | -KI | VNGEE | AVPGSWPWQ | VSLQ | DKTGF | ---- | -HFCGGSLINE |
| | (10) | | (20) | | (30) | | (40) | |

| | | 60 | | 70 | | 80 | | 90 | | 100 | |
|---|---|---|---|---|---|---|---|---|---|---|---|
| Medaka | DWLLTAAH | CVYG | KNTHLQYW | SAVLGLHA | QSMNS | QEVQIRQ | VDRI | INKNYNRRT |
| Human | DWLVSAAH | CVYG | RNLEPSKW | TAILGLHM | KSNLTSPQ | TVPRLI | DEIVINPHY | NRR |
| Mouse | DWLVSAAH | CVYG | RNLDPTRW | TAVLGLHM | QSNLTSPQ | IETRLI | DEIVINPHY | NSS |
| Bovine | DWLVSAAH | CVYG | MEPSKW | KAVLGLHM | ASNLTSPQ | IETRLI | DQIVINPHY | DRR |
| Porcine | DWLVSAAH | CVYG | RNLEPSKW | KAILGLHM | TSNLTSPQ | IVTRLI | DEIVINPHY | NKR |
| Chymo | GV | ---- | -TTSDVV | VAGEFDQGSSS | -EKIQKLKI | AKVFKNS | KYNSLT |
| | (50) | | (60) | | (70) | | (80) | | (90) |

FIG. 1B-1

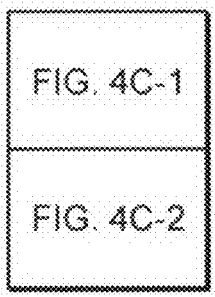
FIG. 4C
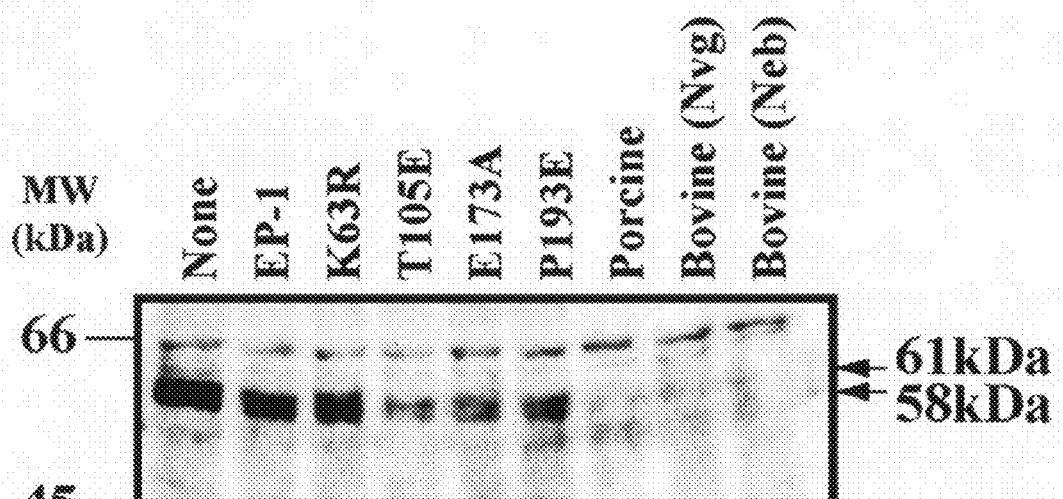
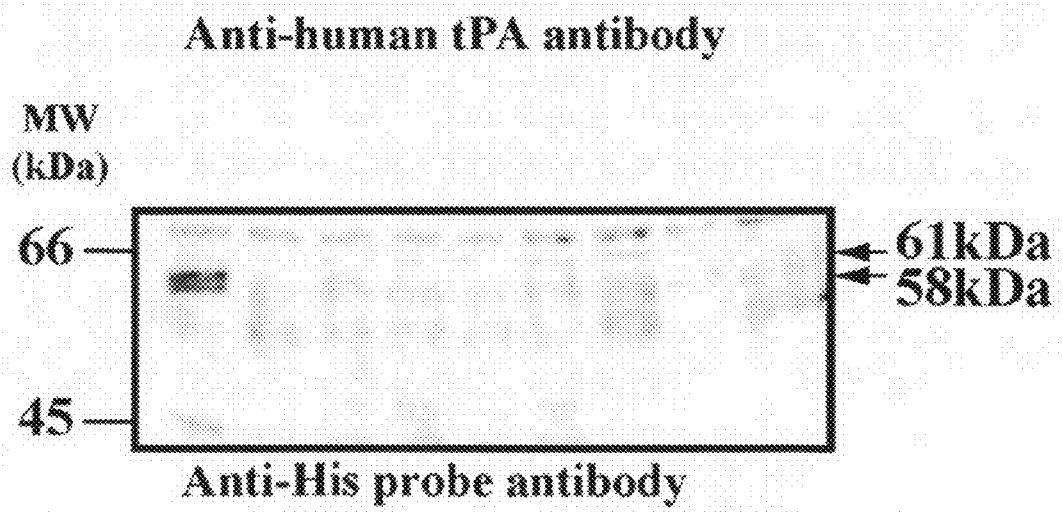
FIG. 4C-1

```
1    MKRRLTNLEVLLTVTTSLFAVCCVCLIVVSCIGLKPEGAAQPVQLTGQMVITAGAAFSEE   60
1    MKRRLTNLEVLLTVTTSLFAVCCVCLIVVSCIGLKPEGAAEPVQLIGQMVITAGAAFSEE   60

61   LRNSSSHFFKSLAFDVQQLVSDAFGASELRLLYRSFRVLYFRPGSIAVTFDLEFNQQIDL   120
61   LRNSSSHLFKSLAFDVQQLVSDAFGASELRLLYRSFRVLYFRPGSIAVTFDLEFNQQIDL   120

121  NEVKQQLGEGLQQIEDGALVIDVDSIQITVKPSSTTPQPTTGHITTETMPITGHTTPA    180
121  NEVKQQLGEGLQQIEDGALVIDVDSIQITEKPSSTTPETSTTGHITTETMPITGHTTPA    180

181  ATPTAASCPPDHSLCWDRSTCVLTDVLCDGVSDCPDASDENSSRCATTCDGQFVLGGPNG   240
181  ATPTAASCPPDHSLCWDRSTCVLTDVLCDGVSDCPDASDENSSRCATTCDGQFVLGGPNG   240

241  TFRSSETETYRNNSNCRWIIRMDGGLSVQVNFHHFETEEYSDVLKLYEGVGPHKQLAAEL   300
241  TFRSSETETYRNNSNCRWIIRMDGGLSVQVNFHHFETEEYSDVLKLYEGVGPHKQLAAEL   300

301  SGPSPPGTVLLLNNQVTVEFTSDGVNDLSGFRASYAAVNTSSLSNQEKLSCSFDQGFCFW   360
301  SGPSPPGTVLLLNNQVTVEFTSDGVNDLSGFRASYVAVNTSSLSNQEKLSCSFDQGFCFW   360

361  RQLQDSFDTWIRTNVPTFPPLTGPNFDHTFGNSSGFYIVTSLSPGQWLKSFVINSLPLAP   420
361  RQLQDSFDTWIRTNVPTFPPLTGPNFDHTFGNSSGFYIVTSLSPGQWLKSFVINSLPLAP   420

421  SSHPTCLSFWYHMFGEDVYRLRVLLRPSQPELTEVVLFHKEGNFGDNWNYAQITLNLSTE   480
421  SSHPTCLSFWYHMFGEDVYRLRVLLRPSQPELTEVVLFHKEGNFGDNWNYAQITLNLSTE   480

481  STVVFEAQKEGGNQNDIALDDDISLRSEGCCGPAPPEPTNVPLPTTAAPIPPDCGGPFDLWE   540
481  STVVFEAQKEGGNQNDIALDDDISLRSEGCCGPAPPEPTNVPLPTTAAPIPPDCGGPFDLWE   540
```

FIG. 5A-1

```
541  PNSTFTSPNYPQSYGD RAECLWTLHAEKGQNIQLHFLDFDVEATYDVVEVRDGAGLNSTL  600
541  PNSTFTSPNYPQSYGD GAECLWTLHAEKGQNIQLHFLDFDVEATYDVVEVRDGAGLNSTL  600

601  LAVLSGSDGPT HDLYSTDNQMTVWFYTDSGGFGRGFRANFTSGVNLGSQAPC ANGQFQCQ  660
601  LAVLSGSDGPT RDLYSTDNQMTVWFYTDSGGFGRGFRANFTSGVNLGSQAPC TNGQFQCQ  660

661  TGDCIHGDRQCDGVADCPDGYDEADCVALQVNGSHRLHFR LHSLLTVCADTWDSELSDF  720
661  TGDCIHGDRQCDGVADCPDGYDEADCVALQVNGSHRLHFL LLRSLLTVCADTWDSELSDF  720

721  TCQYLGYRSGEESLQ PVLPQDAAFAVVTVSSNGTLETQVRETCSSGEVISLNCSNQPCGQ  780
721  TCQYLGYRSGEESLQ SVLPQDAAFAVVTVSSNGTLETQVRETCSSGEVISLNCSNQPCGQ  780

781  RQVYN------SKENNGVPRVVGGVNAEKGAWPWMVSLHWRGRHGCGASLIGRDWLLTA  833
781  RQVYN HGDQSENSKENNGVPRVVGGVNAEKGAWPWMVSLHWRGRHGCGASLIGRDWLLTA  840

834  AHCVYGKNTHLQYWSAVLGLHAQSSMNSQEVQIRQVDRIIINKNYNRRTKEADIAMMHLQ  893
841  AHCVYGKNTHLQYWSAVLGLHAQSSMNSQEVQIRQVDRIIINKNYNRRTKEADIAMMHLQ  900

894  QPVNFTEWVLPVCLASE DQHFPAGRRCFIAGWGRDAEGGSLPDILQEAEVPLVDQDECQR  953
901  QPVNFTEWVLPVCLASE GQHFPAGRRCFIAGWGRDAEGGSLPDILQEAEVPLVDQDECQR  960

954  LLPEYTFFTSSMLCAGYPEGGVDSCQGDSGGPLMCLEDARWTLIGVTSFGVGCGRPERPGA  1013
961  LLPEYTFFTSSMLCAGYPEGGVDSCQGDSGGPLMCLEDARWTLIGVTSFGVGCGRPERPGA  1020

1014 YARVSAFT TSWIAETRRSSFSDLD  1036
1021 YARVSAFA SSWIAETRRSSFSDLD  1043
```

FIG. 5A-2

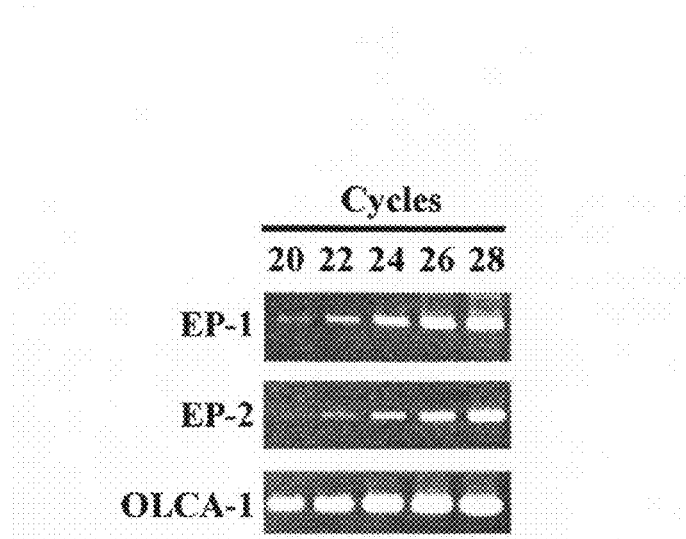
FIG. 5B
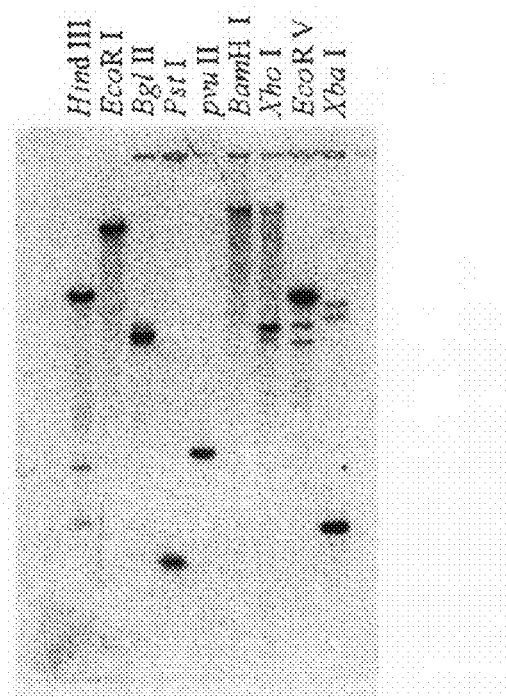
FIG. 5C
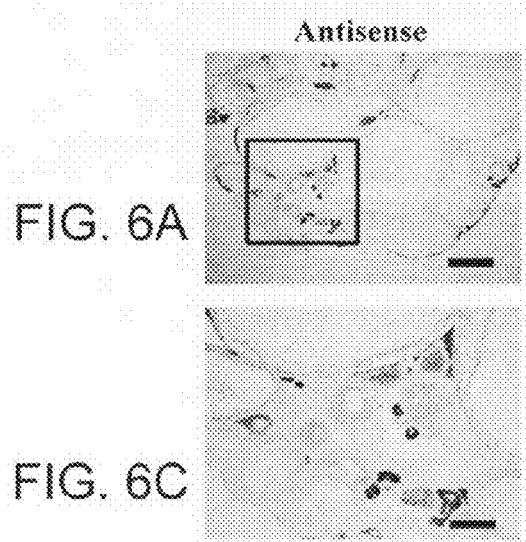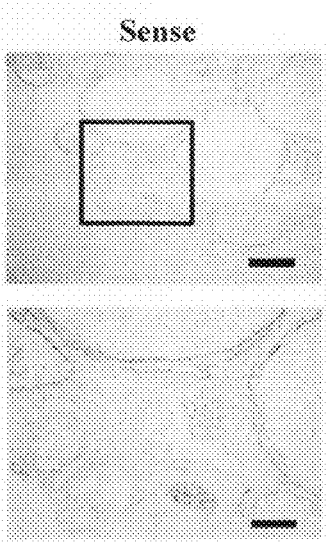
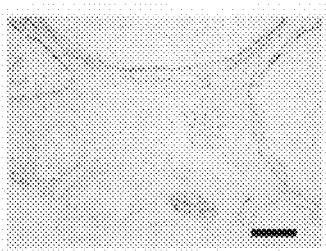
FIG. 6A  FIG. 6B
FIG. 6C  FIG. 6D

FIG. 9A

SEQ ID NO:1

DDDDK

SEQ ID NO:2

VVGGVNAEKGAWPWMVSLHWRGRHGCGASLIGRDWLLTAAHCVYGKNTHLQYWSAVLGLHAQSSMNSQ
EVQIRQVDRIINKNYNRRTKEADIAMMHLQQPVNFTEWVLPVCLASEDQHFPAGRKCFIAGWGRDAEGGSLP
DILQEAEVPLVDQDECQRLLPEYTFTSSMLCAGYPEGGVDSCQGDSGGPLMCLEDARWTLIGVTSFGVGCGR
PERPGAYARVSAFTSWIAETRRSSFSDLD*

SEQ ID NO:3

GTGGTGGGTGTCAATGCTGAAAAGGGGGCGTGGCCATGGATGGTGTCCCTACACTGGAGGGGCGT
CATGGCTGTGTGCCTCACTGATCGGCAGCTGTGTTGCCTTGGCCTTCATGCTGACTGCTGCTGGAAGA
ACACACACCTGCAGTACTGGTCAGTGCTGGGACTGGCTTCTTGGCCTTCAAGAGCAGCAGACTCACAGAAGT
TCAGATCCGGCAGGTGGACCGCATTATCAACAAGAACTACAACAGAAGAACCAAAGAGGCAGACAT
CGCCATGATGCACCTGCAGCAGCCAGTCAACTTCACTGAGTGGGTTCTGCCTGTGTTTAGCATCAGAA
GATCAACATTTTCCAGCTGGAAGAAGGCTGTTCATTGCAGGGTCGGGGTGGGACGCTGAAGGAGGATCTC
TACCTGACATTCTACAGAGAGGCTGAGGTTCCCCTGGTGGACATATCCTGGATATCCTGATGTGCTGAAGGCGGAGGTGACCAGGA
GTACACCTTCACCTGAGAGACTCTGATGTGCTTAGAAGATGCACGGTGACTCTGATTGGTGACATCATTGGCGTTG
TCTGGAGACCTGGGGTCTCGAGAGACTGGAGCTTATGCTGTCGAGTTCGAGTCCTGCTTTCACTTCATGGATTGCTGAGACC
AGGGCGCTCCTCTGTTCTCAGATCTAGACTGA

SEQ ID NO:4

VVGGVNAEKGAWPWMVSLHWRGRHGCGASLIGRDWLLTAAHCVYGKNTHLQYWSAVLGLHAQSSMNSQ
EVQRQVDRIIINKNYNRRTKEADIAMMHLQQPVNFTEWVLPVCLASEDQHFPAGRRCFIAGWGRDAEGGSLP
DILQEAEVPLVDQDACQRLLPEYTFTSSMLCAGYPEGGVDSCQGDSGGPLMCLEDARWTLIGVTSFGVGCR
PERPGAYARVSAFTSWIAETRRSSFSDLD*

SEQ ID NO:5

GTGGTGGGGTGGGGTCAATGCTGAAAAGGGCGGTGGCCATGGATGGTGTCCCTACACTGAGGGGCGT
CATGGCTGTGTGGTGCCTCACTGACTGGCCAGAGACTGGTTGCTGACTGTCTCGAGAGCATGAAGA
ACACACCTGACTACTGGACCGCAGTGCTGTTCTTGGCCTTCATGAGACAGCAGAAGAACCAAGAGT
TCAGATCCGGACAGGTGGACCGCCAGTCAGTGAAGAAGGTGTTTCATTGCAGGTGGGGACCAGACAT
CGCCATGATGCACCTGCAGCAGCCAGTCAGTGAAGAAGGTGTTTCATTGCAGGTGGGGACGCTGAA
GATCAACATTTTCAGTGGGACCTGAAGAGGCTGAGGTTCCCCTGGTGCTGAGATATCCTGAAGGCGGAGTTGA
TACCTGACATTCCACCTTCACCTGCAGCATGCTAGAGATGCACGGTCGAGCTTATGCTGACTTCACTCTGT
GTACACCTTCACCTGCAGCATGCTAGAGATGCACGGTCGAGCTTATGCTGACTTCACTCTGTGTGCATCATTTGGCGTTG
TCTGGAGACCTGTCCGAGAGACCTGGAGCTCGAGTTCTCGAGTCGAGCTTATGCTGACTTCACTCTGTGTGCATCATTTGGCGTTG
GCTGTGGGGCGTCGAGAGACCTGGAGCTCGAGTCGAGCTTATGCTGACTTCACTCTGTGTGCATCATTTGGCGTTG
AGGCGCTCCTCGTTCTCAGATCTAGACTGA

SEQUENCE LISTING

```
<160> NUMBER OF SEQ ID NOS: 76

<210> SEQ ID NO 1
<211> LENGTH: 5
<212> TYPE: PRT
<213> ORGANISM: Oryzias latipes

<400> SEQUENCE: 1

Asp Asp Asp Asp Lys
1               5

<210> SEQ ID NO 2
<211> LENGTH: 242
<212> TYPE: PRT
<213> ORGANISM: Oryzias latipes

<400> SEQUENCE: 2

Val Val Gly Gly Val Asn Ala Glu Lys Gly Ala Trp Pro Trp Met Val
```

```
              1               5              10              15
         Ser Leu His Trp Arg Gly Arg His Gly Cys Gly Ala Ser Leu Ile Gly
                            20                  25                  30

Arg Asp Trp Leu Leu Thr Ala Ala His Cys Val Tyr Gly Lys Asn Thr
                         35                  40                  45

His Leu Gln Tyr Trp Ser Ala Val Leu Gly Leu His Ala Gln Ser Ser
                     50                  55                  60

Met Asn Ser Gln Glu Val Gln Ile Arg Gln Val Asp Arg Ile Ile Ile
          65                  70                  75                  80

Asn Lys Asn Tyr Asn Arg Arg Thr Lys Glu Ala Asp Ile Ala Met Met
                             85                  90                  95

His Leu Gln Gln Pro Val Asn Phe Thr Glu Trp Val Leu Pro Val Cys
                         100                 105                 110

Leu Ala Ser Glu Asp Gln His Phe Pro Ala Gly Arg Cys Phe Ile
                     115                 120                 125

Ala Gly Trp Gly Arg Asp Ala Glu Gly Gly Ser Leu Pro Asp Ile Leu
                     130                 135                 140

Gln Glu Ala Glu Val Pro Leu Val Asp Gln Asp Glu Cys Gln Arg Leu
         145                 150                 155                 160

Leu Pro Glu Tyr Thr Phe Thr Ser Ser Met Leu Cys Ala Gly Tyr Pro
                             165                 170                 175

Glu Gly Gly Val Asp Ser Cys Gln Gly Asp Ser Gly Gly Pro Leu Met
                         180                 185                 190

Cys Leu Glu Asp Ala Arg Trp Thr Leu Ile Gly Val Thr Ser Phe Gly
                     195                 200                 205

Val Gly Cys Gly Arg Pro Glu Arg Pro Gly Ala Tyr Ala Arg Val Ser
                     210                 215                 220

Ala Phe Thr Ser Trp Ile Ala Glu Thr Arg Arg Ser Ser Phe Ser Asp
         225                 230                 235                 240

Leu Asp

<210> SEQ ID NO 3
<211> LENGTH: 729
<212> TYPE: DNA
<213> ORGANISM: Oryzias latipes

<400> SEQUENCE: 3
gtggtgggtg gggtcaatgc tgaaaagggg gcgtggccat ggatggtgtc cctacactgg      60
agggggcgtc atggctgtgg tgcctcactg atcggcagag actggttgct gactgctgca     120
cactgtgtct atgggaagaa cacacacctg cagtactggt cagctgttct tggccttcat     180
gctcagagca gcatgaactc acaggaagtt cagatccggc aggtggaccg cattatcatc     240
aacaagaact acaacagaag aaccaaagag gcagacatcg ccatgatgca cctgcagcag     300
ccagtcaact tcactgagtg ggttctgcct gtgtgtttag catcagaaga tcaacatttt     360
ccagctggaa gaaggtgttt cattgcaggg tgggtcggga cgctgaagg aggatctcta      420 cctgacattc tacaggaggc tgaggttccc ctggtggacc aggatgagtg ccagcgtctc     480
ttacccgagt acaccttcac ctccagcatg ctatgtgctg gatatcctga aggcggagtt     540
gactcctgtc aggtgactc tggaggacct ctgatgtgct agaagatgc acggtggact      600 ctgattggtg tgacatcatt ggcgttggc tgtgggcgtc ctgagagacc tggagcttat      660
gctcgagtgt ctgctttcac ttcatggatt gctgagacca ggcgctcctc gttctcagat     720
ctagactga                                                              729
```

<210> SEQ ID NO 4
<211> LENGTH: 242
<212> TYPE: PRT
<213> ORGANISM: Oryzias latipes

<400> SEQUENCE: 4

Val Val Gly Gly Val Asn Ala Glu Lys Gly Ala Trp Pro Trp Met Val
1               5                   10                  15

Ser Leu His Trp Arg Gly Arg His Gly Cys Gly Ala Ser Leu Ile Gly
            20                  25                  30

Arg Asp Trp Leu Leu Thr Ala Ala His Cys Val Tyr Gly Lys Asn Thr
        35                  40                  45

His Leu Gln Tyr Trp Ser Ala Val Leu Gly Leu His Ala Gln Ser Ser
    50                  55                  60

Met Asn Ser Gln Glu Val Gln Ile Arg Gln Val Asp Arg Ile Ile Ile
65                  70                  75                  80

Asn Lys Asn Tyr Asn Arg Arg Thr Lys Glu Ala Asp Ile Ala Met Met
                85                  90                  95

His Leu Gln Gln Pro Val Asn Phe Thr Glu Trp Val Leu Pro Val Cys
            100                 105                 110

Leu Ala Ser Glu Asp Gln His Phe Pro Ala Gly Arg Arg Cys Phe Ile
        115                 120                 125

Ala Gly Trp Gly Arg Asp Ala Glu Gly Gly Ser Leu Pro Asp Ile Leu
    130                 135                 140

Gln Glu Ala Glu Val Pro Leu Val Asp Gln Asp Ala Cys Gln Arg Leu
145                 150                 155                 160

Leu Pro Glu Tyr Thr Phe Thr Ser Ser Met Leu Cys Ala Gly Tyr Pro
                165                 170                 175

Glu Gly Gly Val Asp Ser Cys Gln Gly Asp Ser Gly Gly Pro Leu Met
            180                 185                 190

Cys Leu Glu Asp Ala Arg Trp Thr Leu Ile Gly Val Thr Ser Phe Gly
        195                 200                 205

Val Gly Cys Gly Arg Pro Glu Arg Pro Gly Ala Tyr Ala Arg Val Ser
    210                 215                 220

Ala Phe Thr Ser Trp Ile Ala Glu Thr Arg Ser Ser Phe Ser Asp
225                 230                 235                 240

Leu Asp

<210> SEQ ID NO 5
<211> LENGTH: 729
<212> TYPE: DNA
<213> ORGANISM: Oryzias latipes

<400> SEQUENCE: 5
gtggtgggtg gggtcaatgc tgaaaagggg gcgtggccat ggatggtgtc cctacactgg      60 aggggcgtc atggctgtgg tgcctcactg atcggcagag actggttgct gactgctgca     120
cactgtgtct atgggaagaa cacacacctg cagtactggt cagctgttct tggccttcat    180
gctcagagca gcatgaactc acaggaagtt cagatccggc aggtggaccg cattatcatc    240
aacaagaact acaacagaag aaccaaagag gcagacatcg ccatgatgca cctgcagcag    300
ccagtcaact tcactgagtg ggttctgcct gtgtgtttag catcagaaga tcaacatttt    360
ccagctggaa gaaggtgttt cattgcaggg tggggtcggg acgctgaagg aggatctcta    420
cctgacattc tacaggaggc tgaggttccc ctggtggacc aggatgcgtg ccagcgtctc    480
ttacccgagt acaccttcac ctccagcatg ctatgtgctg gatatcctga aggcggagtt    540

-continued

```
gactcctgtc agggtgactc tggaggacct ctgatgtgct tagaagatgc acggtggact    600
ctgattggtg tgacatcatt tggcgttggc tgtgggcgtc ctgagagacc tggagcttat    660
gctcgagtgt ctgctttcac ttcatggatt gctgagacca ggcgctcctc gttctcagat    720
ctagactga                                                            729
```

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Asp Asp Asp Asp Lys
1               5

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtkstbwcwg ctgcycactg                                                 20

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Leu Thr Ala Ala His Cys
1               5

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
wgggccwccd gagtcwcc                                                   18

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Asp Ser Gly Gly Pro
1               5

<210> SEQ ID NO 11
<211> LENGTH: 16

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aggaggtgat gaactg                                                        16

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctcggttccg tcattgttcc gggat                                              25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccagacgcac ctccactcgg gact                                               24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
catgatcacc aactccatgt tctg                                               24

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tggatacctg gagggagg                                                      18

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agaacatcac aggtgaaccg gtga                                               24

<210> SEQ ID NO 17
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 17
ttctgacatt cctgaaggga cagc                                              24

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caagaactac aacagaagaa                                                   20

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtgtattgag aaaaaggttg ttaa                                              24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctgtactaag aaaaaatttg tcat                                              24

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aggtaaccaa gcagag                                                       16

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gagaacgagg agcgcctggt ctca                                              24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
```

```
                                           primer

<400> SEQUENCE: 23
atccatgaag tgaaagcaga cact                                          24

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aggaccaaac ggaacatttc                                               20

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gagagggacg caggagga                                                 18

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccggaattcc ttgacgatga caag                                          24

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cccaagcttt cagttgctag ccatggt                                       27

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cccaagctta tgaagagagg gctctgctgt                                    30

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 29
cttatcgtca tcatgatgat gatgatggtg tctggctcct cttct            45

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caccatcatc atcatcatga tgacgacgat aagtcttacc aagtgatc          48

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccgctcgagt cacggtcgca tgttgtcacg aat                          33

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

His His His His His His Asp Asp Asp Asp Lys
1               5                   10

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: Inosine

<400> SEQUENCE: 33
tcngcygcmc actgygtsta yrgr                                    24

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Ala Ala His Cys Val Tyr Gly
1               5

<210> SEQ ID NO 35
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 35
kartggycck ccwgaatcmc cctg                                            24

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gly Asp Ser Gly Gly Pro Leu
1               5

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gacattctac aggaggctga ggtt                                            24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cgtctcttac ccgagtacac cttc                                            24

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgcggatccc aagctggtgt ggtgggtgg                                       29

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cccaagcttt cagtctagat ctgagaa                                         27

<210> SEQ ID NO 41
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 41
gtctatggga ggaacacaca c                                               21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtgtgtgttc ctcccataga c                                               21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gtctatgggg cgaacacaca c                                               21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gtgtgtgttc gccccataga c                                               21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtctatgggg agaacacaca c                                               21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gtgtgtgttc tccccataga c                                               21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 47
aacagaagaa ggaaagaggc a                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tgcctctttc cttcttctgt t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aacagaagag ccaaagaggc a                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgcctctttg gctcttctgt t                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aacagaagag aaaagaggc a                                               21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tgcctctttt tctcttctgt t                                              21

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
```
ggaagaaggt gttccattgc agggtgg                                              27

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccaccctgca atggaacacc ttcttcc                                              27

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggaagaaggt gtgccattgc agggtgg                                              27

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ccaccctgca atggcacacc ttcttcc                                              27

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gtggaccagg ataagtgcca gcgtctc                                              27

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gagacgctgg cacttatcct ggtccac                                              27

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gagacgctgg cacttatcct ggtccac                                              27

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gagacgctgg cacgcatcct ggtccac                                        27

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgtgctggat atgaagaagg cggagtt                                        27

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aactccgcct tcttcatatc cagcaca                                        27

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tgtgctggat atgctgaagg cggagtt                                        27

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
aactccgcct tcagcatatc cagcaca                                        27

<210> SEQ ID NO 65
<211> LENGTH: 259
<212> TYPE: PRT
<213> ORGANISM: Oryzias latipes

<400> SEQUENCE: 65

Cys Gly Gln Arg Gln Val Tyr Asn Ser Lys Glu Asn Asn Gly Val Pro
1               5                   10                  15

Arg Val Val Gly Gly Val Asn Ala Glu Lys Gly Ala Trp Pro Trp Met
            20                  25                  30

Val Ser Leu His Trp Arg Gly Arg His Gly Cys Gly Ala Ser Leu Ile
         35                  40                  45

Gly Arg Asp Trp Leu Leu Thr Ala Ala His Cys Val Tyr Gly Lys Asn
 50                  55                  60

Thr His Leu Gln Tyr Trp Ser Ala Val Leu Gly Leu His Ala Gln Ser
 65                  70                  75                  80

Ser Met Asn Ser Gln Glu Val Gln Ile Arg Gln Val Asp Arg Ile Ile
                 85                  90                  95

Ile Asn Lys Asn Tyr Asn Arg Arg Thr Lys Glu Ala Asp Ile Ala Met
             100                 105                 110

Met His Leu Gln Gln Pro Val Asn Phe Thr Glu Trp Val Leu Pro Val
         115                 120                 125

Cys Leu Ala Ser Glu Asp Gln His Phe Pro Ala Gly Arg Arg Cys Phe
130                 135                 140

Ile Ala Gly Trp Gly Arg Asp Ala Glu Gly Gly Ser Leu Pro Asp Ile
145                 150                 155                 160

Leu Gln Glu Ala Glu Val Pro Leu Val Asp Gln Asp Glu Cys Gln Arg
                165                 170                 175

Leu Leu Pro Glu Tyr Thr Phe Thr Ser Ser Met Leu Cys Ala Gly Tyr
            180                 185                 190

Pro Glu Gly Gly Val Asp Ser Cys Gln Gly Asp Ser Gly Gly Pro Leu
        195                 200                 205

Met Cys Leu Glu Asp Ala Arg Trp Thr Leu Ile Gly Val Thr Ser Phe
210                 215                 220

Gly Val Gly Cys Gly Arg Pro Glu Arg Pro Gly Ala Tyr Ala Arg Val
225                 230                 235                 240

Ser Ala Phe Thr Ser Trp Ile Ala Glu Thr Arg Arg Ser Ser Phe Ser
                245                 250                 255

Asp Leu Asp

<210> SEQ ID NO 66
<211> LENGTH: 248
<212> TYPE: PRT
<213> ORGANISM: Homo sapiens

<400> SEQUENCE: 66

Cys Gly Lys Lys Leu Ala Ala Gln Asp Ile Thr Pro Lys Ile Val Gly
 1               5                  10                  15

Gly Ser Asn Ala Lys Glu Gly Ala Trp Pro Trp Val Val Gly Leu Tyr
             20                  25                  30

Tyr Gly Gly Arg Leu Leu Cys Gly Ala Ser Leu Val Ser Ser Asp Trp
         35                  40                  45

Leu Val Ser Ala Ala His Cys Val Tyr Gly Arg Asn Leu Glu Pro Ser
 50                  55                  60

Lys Trp Thr Ala Ile Leu Gly Leu His Met Lys Ser Asn Leu Thr Ser
 65                  70                  75                  80

Pro Gln Thr Val Pro Arg Leu Ile Asp Glu Ile Val Ile Asn Pro His
                 85                  90                  95

Tyr Asn Arg Arg Arg His Asp Asn Asp Ile Ala Met Met His Leu Glu
             100                 105                 110

Phe Lys Val Asn Tyr Thr Asp Tyr Ile Gln Pro Ile Cys Leu Pro Glu
         115                 120                 125

Glu Asn Gln Val Phe Pro Pro Gly Arg Asn Cys Ser Ile Ala Gly Trp
130                 135                 140

Gly Thr Val Val Tyr Gln Gly Thr Thr Ala Asn Ile Leu Gln Glu Ala

```
                145                 150                 155                 160
Asp Val Pro Leu Leu Ser Asn Glu Arg Cys Gln Gln Gln Met Pro Glu
                    165                 170                 175

Tyr Asn Ile Thr Glu Asn Met Ile Cys Ala Gly Tyr Glu Glu Gly Gly
                180                 185                 190

Ile Asp Ser Cys Gln Gly Asp Ser Gly Gly Pro Leu Met Cys Gln Glu
            195                 200                 205

Asn Asn Arg Trp Phe Leu Ala Gly Val Thr Ser Phe Gly Tyr Lys Cys
        210                 215                 220

Ala Leu Pro Asn Arg Pro Gly Val Tyr Ala Arg Val Ser Arg Phe Thr
225                 230                 235                 240

Glu Trp Ile Gln Ser Phe Leu His
                245

<210> SEQ ID NO 67
<211> LENGTH: 253
<212> TYPE: PRT
<213> ORGANISM: Mus sp.

<400> SEQUENCE: 67

Cys Gly Glu Lys Lys Val Thr Gln Lys Val Ser Pro Lys Ile Val Gly
1               5                   10                  15

Gly Ser Asp Ala Gln Ala Gly Ala Trp Pro Trp Val Val Ala Leu Tyr
            20                  25                  30

His Arg Asp Arg Ser Thr Asp Arg Leu Leu Cys Gly Ala Ser Leu Val
        35                  40                  45

Ser Ser Asp Trp Leu Val Ser Ala Ala His Cys Val Tyr Arg Arg Asn
50                  55                  60

Leu Asp Pro Thr Arg Trp Thr Ala Val Leu Gly Leu His Met Gln Ser
65                  70                  75                  80

Asn Leu Thr Ser Pro Gln Val Val Arg Arg Val Val Asp Gln Ile Val
                85                  90                  95

Ile Asn Pro His Tyr Asp Arg Arg Lys Val Asn Asp Ile Ala Met
            100                 105                 110

Met His Leu Glu Phe Lys Val Asn Tyr Thr Asp Tyr Ile Gln Pro Ile
        115                 120                 125

Cys Leu Pro Glu Glu Asn Gln Ile Phe Ile Pro Gly Arg Thr Cys Ser
130                 135                 140

Ile Ala Gly Trp Gly Tyr Asp Lys Ile Asn Ala Gly Ser Thr Val Asp
145                 150                 155                 160

Val Leu Lys Glu Ala Asp Val Pro Leu Ile Ser Asn Glu Lys Cys Gln
                165                 170                 175

Gln Gln Leu Pro Glu Tyr Asn Ile Thr Glu Ser Met Ile Cys Ala Gly
            180                 185                 190

Tyr Glu Glu Gly Gly Ile Asp Ser Cys Gln Gly Asp Ser Gly Gly Pro
        195                 200                 205

Leu Met Cys Gln Glu Asn Asn Arg Trp Phe Leu Val Gly Val Thr Ser
    210                 215                 220

Phe Gly Val Gln Cys Ala Leu Pro Asn His Pro Gly Val Tyr Val Arg
225                 230                 235                 240

Val Ser Gln Phe Ile Glu Trp Ile His Ser Phe Leu His
                245                 250

<210> SEQ ID NO 68
<211> LENGTH: 248
<212> TYPE: PRT
```

<213> ORGANISM: Bos sp.

<400> SEQUENCE: 68

```
Cys Gly Lys Lys Leu Val Thr Gln Glu Val Ser Pro Lys Ile Val Gly
1               5                   10                  15

Gly Ser Asp Ser Arg Glu Gly Ala Trp Pro Trp Val Val Ala Leu Tyr
            20                  25                  30

Phe Asp Asp Gln Gln Val Cys Gly Ala Ser Leu Val Ser Arg Asp Trp
        35                  40                  45

Leu Val Ser Ala Ala His Cys Val Tyr Gly Arg Asn Met Glu Pro Ser
    50                  55                  60

Lys Trp Lys Ala Val Leu Gly Leu His Met Ala Ser Asn Leu Thr Ser
65                  70                  75                  80

Pro Gln Ile Glu Thr Arg Leu Ile Asp Gln Ile Val Ile Asn Pro His
                85                  90                  95

Tyr Asn Lys Arg Arg Lys Asn Asn Asp Ile Ala Met Met His Leu Glu
            100                 105                 110

Met Lys Val Asn Tyr Thr Asp Tyr Ile Gln Pro Ile Cys Leu Pro Glu
        115                 120                 125

Glu Asn Gln Val Phe Pro Pro Gly Arg Ile Cys Ser Ile Ala Gly Trp
    130                 135                 140

Gly Ala Leu Ile Tyr Gln Gly Ser Thr Ala Asp Val Leu Gln Glu Ala
145                 150                 155                 160

Asp Val Pro Leu Leu Ser Asn Glu Lys Cys Gln Gln Gln Met Pro Glu
                165                 170                 175

Tyr Asn Ile Thr Glu Asn Met Val Cys Ala Gly Tyr Glu Ala Gly Gly
            180                 185                 190

Val Asp Ser Cys Gln Gly Asp Ser Gly Gly Pro Leu Met Cys Gln Glu
        195                 200                 205

Asn Asn Arg Trp Leu Leu Ala Gly Val Thr Ser Phe Gly Tyr Gln Cys
    210                 215                 220

Ala Leu Pro Asn Arg Pro Gly Val Tyr Ala Arg Val Pro Arg Phe Thr
225                 230                 235                 240

Glu Trp Ile Gln Ser Phe Leu His
                245
```

<210> SEQ ID NO 69
<211> LENGTH: 248
<212> TYPE: PRT
<213> ORGANISM: Sus sp.

<400> SEQUENCE: 69

```
Cys Gly Lys Lys Gln Val Ala Gln Glu Val Ser Pro Lys Ile Val Gly
1               5                   10                  15

Gly Asn Asp Ser Arg Glu Gly Ala Trp Pro Trp Val Val Ala Leu Tyr
            20                  25                  30

Tyr Asn Gly Gln Leu Leu Cys Gly Ala Ser Leu Val Ser Arg Asp Trp
        35                  40                  45

Leu Val Ser Ala Ala His Cys Val Tyr Gly Arg Asn Leu Glu Pro Ser
    50                  55                  60

Lys Trp Lys Ala Ile Leu Gly Leu His Met Thr Ser Asn Leu Thr Ser
65                  70                  75                  80

Pro Gln Ile Val Thr Arg Leu Ile Asp Glu Ile Val Ile Asn Pro His
                85                  90                  95

Tyr Asn Arg Arg Arg Lys Asp Ser Asp Ile Ala Met Met His Leu Glu
            100                 105                 110
```

Phe Lys Val Asn Tyr Thr Asp Tyr Ile Gln Pro Ile Cys Leu Pro Glu
            115                 120                 125

Glu Asn Gln Val Phe Pro Pro Gly Arg Ile Cys Ser Ile Ala Gly Trp
        130                 135                 140

Gly Lys Val Ile Tyr Gln Gly Ser Pro Ala Asp Ile Leu Gln Glu Ala
145                 150                 155                 160

Asp Val Pro Leu Leu Ser Asn Glu Lys Cys Gln Gln Gln Met Pro Glu
                165                 170                 175

Tyr Asn Ile Thr Glu Asn Met Met Cys Ala Gly Tyr Glu Glu Gly Gly
            180                 185                 190

Ile Asp Ser Cys Gln Gly Asp Ser Gly Gly Pro Leu Met Cys Leu Glu
        195                 200                 205

Asn Asn Arg Trp Leu Leu Ala Gly Val Thr Ser Phe Gly Tyr Gln Cys
210                 215                 220

Ala Leu Pro Asn Arg Pro Gly Val Tyr Ala Arg Val Pro Lys Phe Thr
225                 230                 235                 240

Glu Trp Ile Gln Ser Phe Leu His
            245

<210> SEQ ID NO 70
<211> LENGTH: 245
<212> TYPE: PRT
<213> ORGANISM: Bos sp.

<400> SEQUENCE: 70

Cys Gly Val Pro Ala Ile Gln Pro Val Leu Ser Gly Leu Ser Arg Ile
1               5                   10                  15

Val Asn Gly Glu Glu Ala Val Pro Gly Ser Trp Pro Trp Gln Val Ser
            20                  25                  30

Leu Gln Asp Lys Thr Gly Phe His Phe Cys Gly Gly Ser Leu Ile Asn
        35                  40                  45

Glu Asn Trp Val Val Thr Ala Ala His Cys Gly Val Thr Thr Ser Asp
    50                  55                  60

Val Val Val Ala Gly Glu Phe Asp Gln Gly Ser Ser Ser Glu Lys Ile
65                  70                  75                  80

Gln Lys Leu Lys Ile Ala Lys Val Phe Lys Asn Ser Lys Tyr Asn Ser
                85                  90                  95

Leu Thr Ile Asn Asn Asp Ile Thr Leu Leu Lys Leu Ser Thr Ala Ala
            100                 105                 110

Ser Phe Ser Gln Thr Val Ser Ala Val Cys Leu Pro Ser Ala Ser Asp
        115                 120                 125

Asp Phe Ala Ala Gly Thr Thr Cys Val Thr Thr Gly Trp Gly Leu Thr
    130                 135                 140

Arg Tyr Thr Asn Ala Asn Thr Pro Asp Arg Leu Gln Gln Ala Ser Leu
145                 150                 155                 160

Pro Leu Leu Ser Asn Thr Asn Cys Lys Lys Tyr Trp Gly Thr Lys Ile
                165                 170                 175

Lys Asp Ala Met Ile Cys Ala Gly Ala Ser Gly Val Ser Ser Cys Met
            180                 185                 190

Gly Asp Ser Gly Gly Pro Leu Val Cys Lys Lys Asn Gly Ala Trp Thr
        195                 200                 205

Leu Val Gly Ile Val Ser Trp Gly Ser Ser Thr Cys Ser Thr Ser Thr
    210                 215                 220

Pro Gly Val Tyr Ala Arg Val Thr Ala Leu Val Asn Trp Val Gln Gln
225                 230                 235                 240

```
Thr Leu Ala Ala Asn
                245

<210> SEQ ID NO 71
<211> LENGTH: 1036
<212> TYPE: PRT
<213> ORGANISM: Oryzias latipes

<400> SEQUENCE: 71

Met Lys Arg Arg Leu Thr Asn Leu Glu Val Leu Leu Thr Val Thr Thr
1               5                   10                  15

Ser Leu Phe Ala Val Cys Cys Val Cys Leu Ile Val Val Ser Cys Ile
                20                  25                  30

Gly Leu Lys Pro Glu Gly Ala Ala Gln Pro Val Gln Leu Thr Gly Gln
            35                  40                  45

Met Val Ile Thr Ala Gly Ala Ala Phe Ser Glu Glu Leu Arg Asn Ser
        50                  55                  60

Ser Ser His Phe Phe Lys Ser Leu Ala Phe Asp Val Gln Gln Leu Val
65                  70                  75                  80

Ser Asp Ala Phe Gly Ala Ser Glu Leu Arg Leu Leu Tyr Arg Ser Phe
                85                  90                  95

Arg Val Leu Tyr Phe Arg Pro Gly Ser Ile Ala Val Thr Phe Asp Leu
                100                 105                 110

Glu Phe Asn Gln Gln Ile Asp Leu Asn Glu Val Lys Gln Gln Leu Gly
            115                 120                 125

Glu Gly Leu Gln Gln Ile Glu Asp Gly Ala Leu Val Ile Asp Val Asp
        130                 135                 140

Ser Ile Gln Ile Thr Val Lys Pro Ser Ser Thr Thr Pro Gln Pro Thr
145                 150                 155                 160

Pro Thr Thr Gly His Ile Thr Thr Glu Thr Met Pro Ile Thr Gly His
                165                 170                 175

Thr Thr Pro Ala Ala Thr Pro Thr Ala Ala Ser Cys Pro Pro Asp His
                180                 185                 190

Ser Leu Cys Trp Asp Arg Ser Thr Cys Val Leu Thr Asp Val Leu Cys
            195                 200                 205

Asp Gly Val Ser Asp Cys Pro Asp Ala Ser Asp Glu Asn Ser Ser Arg
        210                 215                 220

Cys Ala Thr Thr Cys Asp Gly Gln Phe Val Leu Gly Gly Pro Asn Gly
225                 230                 235                 240

Thr Phe Arg Ser Ser Glu Thr Glu Thr Tyr Arg Asn Asn Ser Asn Cys
                245                 250                 255

Arg Trp Ile Ile Arg Met Asp Gly Gly Leu Ser Val Gln Val Asn Phe
                260                 265                 270

His His Phe Glu Thr Glu Glu Tyr Ser Asp Val Leu Lys Leu Tyr Glu
            275                 280                 285

Gly Val Gly Pro His Lys Gln Leu Ala Ala Glu Leu Ser Gly Pro Ser
        290                 295                 300

Pro Pro Gly Thr Val Leu Leu Leu Asn Asn Gln Val Thr Val Glu Phe
305                 310                 315                 320

Thr Ser Asp Gly Val Asn Asp Leu Ser Gly Phe Arg Ala Ser Tyr Ala
                325                 330                 335

Ala Val Asn Thr Ser Ser Leu Ser Asn Gln Glu Lys Leu Ser Cys Ser
                340                 345                 350

Phe Asp Gln Gly Phe Cys Phe Trp Arg Gln Leu Gln Asp Ser Phe Asp
            355                 360                 365
```

```
Thr Trp Ile Arg Thr Asn Val Pro Thr Phe Pro Pro Leu Thr Gly Pro
    370                 375                 380

Asn Phe Asp His Thr Phe Gly Asn Ser Ser Gly Phe Tyr Ile Val Thr
385                 390                 395                 400

Ser Leu Ser Pro Gly Gln Trp Leu Lys Ser Phe Val Ile Asn Ser Leu
                405                 410                 415

Pro Leu Ala Pro Ser Ser His Pro Thr Cys Leu Ser Phe Trp Tyr His
            420                 425                 430

Met Phe Gly Glu Asp Val Tyr Arg Leu Arg Val Leu Leu Arg Pro Ser
        435                 440                 445

Gln Pro Glu Leu Thr Glu Val Val Leu Phe His Lys Glu Gly Asn Phe
    450                 455                 460

Gly Asp Asn Trp Asn Tyr Ala Gln Ile Thr Leu Asn Leu Ser Thr Glu
465                 470                 475                 480

Ser Thr Val Val Phe Glu Ala Gln Lys Glu Gly Asn Gln Asn Asp
                485                 490                 495

Ile Ala Leu Asp Asp Ile Ser Leu Arg Ser Glu Gly Cys Gly Pro Ala
            500                 505                 510

Pro Pro Glu Pro Thr Asn Val Pro Leu Pro Thr Thr Ala Ala Pro Ile
        515                 520                 525

Pro Pro Asp Cys Gly Gly Pro Phe Asp Leu Trp Glu Pro Asn Ser Thr
    530                 535                 540

Phe Thr Ser Pro Asn Tyr Pro Gln Ser Tyr Gly Asp Arg Ala Glu Cys
545                 550                 555                 560

Leu Trp Thr Leu His Ala Glu Lys Gly Gln Asn Ile Gln Leu His Phe
                565                 570                 575

Leu Asp Phe Asp Val Glu Ala Thr Tyr Asp Val Val Glu Val Arg Asp
            580                 585                 590

Gly Ala Gly Leu Asn Ser Thr Leu Leu Ala Val Leu Ser Gly Ser Asp
        595                 600                 605

Gly Pro Thr His Asp Leu Tyr Ser Thr Asp Asn Gln Met Thr Val Trp
    610                 615                 620

Phe Tyr Thr Asp Ser Gly Gly Phe Gly Arg Gly Phe Arg Ala Asn Phe
625                 630                 635                 640

Thr Ser Gly Val Asn Leu Gly Ser Gln Ala Pro Cys Ala Asn Gly Gln
                645                 650                 655

Phe Gln Cys Gln Thr Gly Asp Cys Ile His Gly Asp Arg Gln Cys Asp
            660                 665                 670

Gly Val Ala Asp Cys Pro Asp Gly Tyr Asp Glu Ala Asp Cys Val Ala
        675                 680                 685

Leu Gln Val Asn Gly Ser His Arg Leu His Phe Arg Leu Leu His Ser
    690                 695                 700

Leu Leu Thr Val Cys Ala Asp Thr Trp Asp Ser Glu Leu Ser Asp Phe
705                 710                 715                 720

Thr Cys Gln Tyr Leu Gly Tyr Arg Ser Gly Glu Glu Ser Leu Gln Pro
                725                 730                 735

Val Leu Pro Gln Asp Ala Ala Phe Ala Val Val Thr Val Ser Ser Asn
            740                 745                 750

Gly Thr Leu Glu Thr Gln Val Arg Glu Thr Cys Ser Ser Gly Glu Val
        755                 760                 765

Ile Ser Leu Asn Cys Ser Asn Gln Pro Cys Gly Gln Arg Gln Val Tyr
    770                 775                 780

Asn Ser Lys Glu Asn Asn Gly Val Pro Arg Val Val Gly Gly Val Asn
```

```
                        785                 790                 795                 800

Ala Glu Lys Gly Ala Trp Pro Trp Met Val Ser Leu His Trp Arg Gly
                805                 810                 815

Arg His Gly Cys Gly Ala Ser Leu Ile Gly Arg Asp Trp Leu Leu Thr
            820                 825                 830

Ala Ala His Cys Val Tyr Gly Lys Asn Thr His Leu Gln Tyr Trp Ser
            835                 840                 845

Ala Val Leu Gly Leu His Ala Gln Ser Ser Met Asn Ser Gln Glu Val
            850                 855                 860

Gln Ile Arg Gln Val Asp Arg Ile Ile Asn Lys Asn Tyr Asn Arg
865                 870                 875                 880

Arg Thr Lys Glu Ala Asp Ile Ala Met Met His Leu Gln Gln Pro Val
                885                 890                 895

Asn Phe Thr Glu Trp Val Leu Pro Val Cys Leu Ala Ser Glu Asp Gln
                900                 905                 910

His Phe Pro Ala Gly Arg Arg Cys Phe Ile Ala Gly Trp Gly Arg Asp
            915                 920                 925

Ala Glu Gly Gly Ser Leu Pro Asp Ile Leu Gln Glu Ala Glu Val Pro
            930                 935                 940

Leu Val Asp Gln Asp Glu Cys Gln Arg Leu Leu Pro Glu Tyr Thr Phe
945                 950                 955                 960

Thr Ser Ser Met Leu Cys Ala Gly Tyr Pro Glu Gly Gly Val Asp Ser
                965                 970                 975

Cys Gln Gly Asp Ser Gly Gly Pro Leu Met Cys Leu Gly Asp Ala Arg
            980                 985                 990

Trp Thr Leu Ile Gly Val Thr Ser Phe Gly Val Gly Cys Gly Arg Pro
            995                 1000                1005

Glu Arg Pro Gly Ala Tyr Ala Arg Val Ser Ala Phe Thr Ser Trp
    1010                1015                1020

Ile Ala Glu Thr Arg Ser Ser Phe Ser Asp Leu Asp
    1025                1030                1035

<210> SEQ ID NO 72
<211> LENGTH: 1043
<212> TYPE: PRT
<213> ORGANISM: Oryzias latipes

<400> SEQUENCE: 72

Met Lys Arg Arg Leu Thr Asn Leu Glu Val Leu Leu Thr Val Thr Thr
1               5                   10                  15

Ser Leu Phe Ala Val Cys Cys Val Cys Leu Ile Val Val Ser Cys Ile
                20                  25                  30

Gly Leu Lys Pro Glu Gly Ala Ala Glu Pro Val Gln Leu Ile Gly Gln
            35                  40                  45

Met Val Ile Thr Ala Gly Ala Ala Phe Ser Glu Glu Leu Arg Asn Ser
        50                  55                  60

Ser Ser His Leu Phe Lys Ser Leu Ala Phe Asp Val Gln Gln Leu Val
65                  70                  75                  80

Ser Asp Ala Phe Gly Ala Ser Glu Leu Arg Leu Leu Tyr Arg Ser Phe
                85                  90                  95

Arg Val Leu Tyr Phe Arg Pro Gly Ser Ile Ala Val Thr Phe Asp Leu
                100                 105                 110

Glu Phe Asn Gln Gln Ile Asp Leu Asn Glu Val Lys Gln Gln Leu Gly
            115                 120                 125

Glu Gly Leu Gln Gln Ile Glu Asp Gly Ala Leu Val Ile Asp Val Asp
```

```
            130                 135                 140
Ser Ile Gln Ile Thr Glu Lys Pro Ser Ser Thr Thr Pro Glu Pro Thr
145                 150                 155                 160

Ser Thr Thr Gly His Ile Thr Thr Glu Thr Met Pro Ile Thr Gly His
                165                 170                 175

Thr Thr Pro Ala Ala Thr Pro Thr Ala Ala Ser Cys Pro Pro Asp His
                180                 185                 190

Ser Leu Cys Trp Asp Arg Ser Thr Cys Val Leu Thr Asp Val Leu Cys
                195                 200                 205

Asp Gly Val Ser Asp Cys Pro Asp Ala Ser Asp Glu Asn Ser Ser Arg
        210                 215                 220

Cys Ala Thr Thr Cys Asp Gly Gln Phe Val Leu Gly Gly Pro Asn Gly
225                 230                 235                 240

Thr Phe Arg Ser Ser Glu Thr Glu Thr Tyr Arg Asn Asn Ser Asn Cys
                    245                 250                 255

Arg Trp Ile Ile Arg Met Asp Gly Gly Leu Ser Val Gln Val Asn Phe
                260                 265                 270

His His Phe Glu Thr Glu Glu Tyr Ser Asp Val Leu Lys Leu Tyr Glu
            275                 280                 285

Gly Val Gly Pro His Lys Gln Leu Ala Ala Glu Leu Ser Gly Pro Ser
        290                 295                 300

Pro Pro Gly Thr Val Leu Leu Asn Asn Gln Val Thr Val Glu Phe
305                 310                 315                 320

Thr Ser Asp Gly Val Asn Asp Leu Ser Gly Phe Arg Ala Ser Tyr Val
                325                 330                 335

Ala Val Asn Thr Ser Ser Leu Ser Asn Gln Glu Lys Leu Ser Cys Ser
                340                 345                 350

Phe Asp Gln Gly Phe Cys Phe Trp Arg Gln Leu Gln Asp Ser Phe Asp
            355                 360                 365

Thr Trp Ile Arg Thr Asn Val Pro Thr Phe Pro Leu Thr Gly Pro
            370                 375                 380

Asn Phe Asp His Thr Phe Gly Asn Ser Ser Gly Phe Tyr Ile Val Thr
385                 390                 395                 400

Ser Leu Ser Pro Gly Gln Trp Leu Lys Ser Phe Val Ile Asn Ser Leu
                405                 410                 415

Pro Leu Ala Pro Ser Ser His Pro Thr Cys Leu Ser Phe Trp Tyr His
                420                 425                 430

Met Phe Gly Glu Asp Val Tyr Arg Leu Arg Val Leu Leu Arg Pro Ser
            435                 440                 445

Gln Pro Glu Leu Thr Glu Val Val Leu Phe His Lys Glu Gly Asn Phe
        450                 455                 460

Gly Asp Asn Trp Asn Tyr Ala Gln Ile Thr Leu Asn Leu Ser Thr Glu
465                 470                 475                 480

Ser Thr Val Val Phe Glu Ala Gln Lys Glu Gly Asn Gln Asn Asp
                485                 490                 495

Ile Ala Leu Asp Asp Ile Ser Leu Arg Ser Glu Gly Cys Gly Pro Ala
                500                 505                 510

Pro Pro Glu Pro Thr Asn Val Pro Leu Pro Thr Thr Ala Ala Pro Ile
            515                 520                 525

Pro Pro Asp Cys Gly Gly Pro Phe Asp Leu Trp Glu Pro Asn Ser Thr
            530                 535                 540

Phe Thr Ser Pro Asn Tyr Pro Gln Ser Tyr Gly Asp Gly Ala Glu Cys
545                 550                 555                 560
```

```
Leu Trp Thr Leu His Ala Glu Lys Gly Gln Asn Ile Gln Leu His Phe
                565                 570                 575
Leu Asp Phe Asp Val Glu Ala Thr Tyr Asp Val Val Glu Val Arg Asp
            580                 585                 590
Gly Ala Gly Leu Asn Ser Thr Leu Leu Ala Val Leu Ser Gly Ser Asp
        595                 600                 605
Gly Pro Thr Arg Asp Leu Tyr Ser Thr Asp Asn Gln Met Thr Val Trp
    610                 615                 620
Phe Tyr Thr Asp Ser Gly Gly Phe Gly Arg Gly Phe Arg Ala Asn Phe
625                 630                 635                 640
Thr Ser Gly Val Asn Leu Gly Ser Gln Ala Pro Cys Thr Asn Gly Gln
                645                 650                 655
Phe Gln Cys Gln Thr Gly Asp Cys Ile His Gly Asp Arg Gln Cys Asp
            660                 665                 670
Gly Val Ala Asp Cys Pro Asp Gly Tyr Asp Glu Ala Asp Cys Val Ala
        675                 680                 685
Leu Gln Val Asn Gly Ser His Arg Leu His Phe Leu Leu Arg Ser
    690                 695                 700
Leu Leu Thr Val Cys Ala Asp Thr Trp Asp Ser Glu Leu Ser Asp Phe
705                 710                 715                 720
Thr Cys Gln Tyr Leu Gly Tyr Arg Ser Gly Glu Glu Ser Leu Gln Ser
                725                 730                 735
Val Leu Pro Gln Asp Ala Ala Phe Ala Val Thr Val Ser Ser Asn
            740                 745                 750
Gly Thr Leu Glu Thr Gln Val Arg Glu Thr Cys Ser Ser Gly Glu Val
        755                 760                 765
Ile Ser Leu Asn Cys Ser Asn Gln Pro Cys Gly Gln Arg Gln Val Tyr
770                 775                 780
Asn His Gly Asp Gln Ser Glu Asn Ser Lys Glu Asn Asn Gly Val Pro
785                 790                 795                 800
Arg Val Val Gly Gly Val Asn Ala Glu Lys Gly Ala Trp Pro Trp Met
                805                 810                 815
Val Ser Leu His Trp Arg Gly Arg His Gly Cys Gly Ala Ser Leu Ile
            820                 825                 830
Gly Arg Asp Trp Leu Leu Thr Ala Ala His Cys Val Tyr Gly Lys Asn
        835                 840                 845
Thr His Leu Gln Tyr Trp Ser Ala Val Leu Gly Leu His Ala Gln Ser
    850                 855                 860
Ser Met Asn Ser Gln Glu Val Gln Ile Arg Gln Val Asp Arg Ile Ile
865                 870                 875                 880
Ile Asn Lys Asn Tyr Asn Arg Arg Thr Lys Glu Ala Asp Ile Ala Met
                885                 890                 895
Met His Leu Gln Gln Pro Val Asn Phe Thr Glu Trp Val Leu Pro Val
            900                 905                 910
Cys Leu Ala Ser Glu Gly Gln His Phe Pro Ala Gly Arg Arg Cys Phe
        915                 920                 925
Ile Ala Gly Trp Gly Arg Asp Ala Glu Gly Gly Ser Leu Pro Asp Ile
    930                 935                 940
Leu Gln Glu Ala Glu Val Pro Leu Val Asp Gln Asp Glu Cys Gln Arg
945                 950                 955                 960
Leu Leu Pro Glu Tyr Thr Phe Thr Ser Ser Met Leu Cys Ala Gly Tyr
                965                 970                 975
Pro Glu Gly Gly Val Asp Ser Cys Gln Gly Asp Ser Gly Gly Pro Leu
            980                 985                 990
```

```
Met Cys Leu Glu Asp Ala Arg Trp Thr Leu Ile Gly Val Thr Ser Phe
            995                1000                1005

Gly Val Gly Cys Gly Arg Pro Glu Arg Pro Gly Ala Tyr Ala Arg
   1010                1015                1020

Val Ser Ala Phe Ala Ser Trp Ile Ala Glu Thr Arg Arg Ser Ser
   1025                1030                1035

Phe Ser Asp Leu Asp
       1040

<210> SEQ ID NO 73
<211> LENGTH: 242
<212> TYPE: PRT
<213> ORGANISM: Oryzias latipes

<400> SEQUENCE: 73

Met Arg Ser Leu Val Phe Val Leu Leu Ile Gly Ala Ala Phe Ala Leu
1               5                   10                  15

Asp Asp Asp Lys Ile Val Gly Gly Tyr Glu Cys Thr Pro His Ser Gln
                20                  25                  30

Pro His Gln Val Ser Leu Asn Ala Gly Tyr His Phe Cys Gly Gly Ser
            35                  40                  45

Leu Val Asn Gln Asn Trp Val Val Ser Ala Ala His Cys Tyr Gln Ser
        50                  55                  60

Arg Val Glu Val Arg Leu Gly Glu His His Ile Arg Asn Asn Asp Gly
65                  70                  75                  80

Thr Glu Gln Phe Ile Thr Ser Ser Arg Val Ile Arg His Pro Ser Tyr
                85                  90                  95

Asn Ser Tyr Thr Ile Asp Asn Asp Ile Met Leu Ile Lys Leu Ser Thr
            100                 105                 110

Pro Ala Thr Leu Asn Gln Tyr Val Gln Pro Val Ser Leu Pro Ser Gly
        115                 120                 125

Cys Ala Pro Ala Gly Thr Met Cys Leu Val Ser Gly Trp Gly Asn Thr
    130                 135                 140

Met Ser Pro Ala Asp Asp Gly Asp Lys Leu Gln Cys Leu Asn Ile Pro
145                 150                 155                 160

Ile Leu Ser Asp Ser Asp Cys Ser Asn Ser Tyr Pro Gly Met Ile Thr
                165                 170                 175

Asn Ser Met Phe Cys Ala Gly Tyr Leu Glu Gly Gly Lys Asp Ser Cys
            180                 185                 190

Gln Gly Asp Ser Gly Gly Pro Val Val Cys Asn Gly Gln Leu Gln Gly
        195                 200                 205

Ile Val Ser Trp Gly Tyr Gly Cys Ala Glu Arg Asn His Pro Gly Val
    210                 215                 220

Tyr Ala Lys Val Cys Ile Phe Ser Asp Trp Leu Asp Ser Thr Met Ala
225                 230                 235                 240

Ser Asn

<210> SEQ ID NO 74
<211> LENGTH: 247
<212> TYPE: PRT
<213> ORGANISM: Homo sapiens

<400> SEQUENCE: 74

Met Asn Pro Phe Leu Ile Leu Ala Phe Val Gly Ala Ala Val Ala Val
1               5                   10                  15

Pro Phe Asp Asp Asp Asp Lys Ile Val Gly Gly Tyr Thr Cys Glu Glu
```

-continued

```
                 20                  25                  30
Asn Ser Leu Pro Tyr Gln Val Ser Leu Asn Ser Gly Ser His Phe Cys
             35                  40                  45
Gly Gly Ser Leu Ile Ser Glu Gln Trp Val Val Ser Ala Ala His Cys
         50                  55                  60
Tyr Lys Thr Arg Ile Gln Val Arg Leu Gly Glu His Asn Ile Lys Val
65                  70                  75                  80
Leu Glu Gly Asn Glu Gln Phe Ile Asn Ala Ala Lys Ile Ile Arg His
                 85                  90                  95
Pro Lys Tyr Asn Arg Asp Thr Leu Asp Asn Asp Ile Met Leu Ile Lys
             100                 105                 110
Leu Ser Ser Pro Ala Val Ile Asn Ala Arg Val Ser Thr Ile Ser Leu
         115                 120                 125
Pro Thr Ala Pro Pro Ala Ala Gly Thr Glu Cys Leu Ile Ser Gly Trp
     130                 135                 140
Gly Asn Thr Leu Ser Phe Gly Ala Asp Tyr Pro Asp Glu Leu Lys Cys
145                 150                 155                 160
Leu Asp Ala Pro Val Leu Thr Gln Ala Glu Cys Lys Ala Ser Tyr Pro
                 165                 170                 175
Gly Lys Ile Thr Asn Ser Met Phe Cys Val Gly Phe Leu Glu Gly Gly
             180                 185                 190
Lys Asp Ser Cys Gln Arg Asp Ser Gly Gly Pro Val Val Cys Asn Gly
         195                 200                 205
Gln Leu Gln Gly Val Val Ser Trp Gly His Gly Cys Ala Trp Lys Asn
     210                 215                 220
Arg Pro Gly Val Tyr Thr Lys Val Tyr Asn Tyr Val Asp Trp Ile Lys
225                 230                 235                 240
Asp Thr Ile Ala Ala Asn Ser
                 245

<210> SEQ ID NO 75
<211> LENGTH: 246
<212> TYPE: PRT
<213> ORGANISM: Mus musculus

<400> SEQUENCE: 75

Met Arg Ala Leu Leu Phe Leu Ala Leu Val Gly Ala Ala Val Ala Phe
1               5                   10                  15
Pro Val Asp Asp Asp Lys Ile Val Gly Gly Tyr Thr Cys Arg Glu
             20                  25                  30
Asn Ser Val Pro Tyr Gln Val Ser Leu Asn Ser Gly Tyr His Phe Cys
             35                  40                  45
Gly Gly Ser Leu Ile Asn Asp Gln Trp Val Val Ser Ala Ala His Cys
         50                  55                  60
Tyr Lys Ser Arg Ile Gln Val Arg Leu Gly Glu His Asn Ile Asn Val
65                  70                  75                  80
Leu Glu Gly Asn Glu Gln Phe Val Asn Ser Ala Lys Ile Ile Lys His
                 85                  90                  95
Pro Asn Phe Asn Ser Arg Thr Leu Asn Asn Asp Ile Met Leu Ile Lys
             100                 105                 110
Leu Ala Ser Pro Val Thr Leu Asn Ala Arg Val Ala Thr Val Ala Leu
         115                 120                 125
Pro Ser Ser Cys Ala Pro Ala Gly Thr Gln Cys Leu Ile Ser Gly Trp
     130                 135                 140
Gly Asn Thr Leu Ser Phe Gly Val Asn Asn Pro Asp Leu Leu Gln Cys
```

```
            145                 150                 155                 160
Leu Asp Ala Pro Leu Leu Pro Gln Ala Asp Cys Glu Ala Ser Tyr Pro
                165                 170                 175

Gly Lys Ile Thr Asn Asn Met Ile Cys Val Gly Phe Leu Glu Gly Gly
            180                 185                 190

Lys Asp Ser Cys Gln Gly Asp Ser Gly Gly Pro Val Val Cys Asn Gly
        195                 200                 205

Gln Leu Gln Gly Ile Val Ser Trp Gly Tyr Gly Cys Ala Leu Lys Asp
    210                 215                 220

Asn Pro Gly Val Tyr Thr Lys Val Cys Asn Tyr Val Asp Trp Ile Gln
225                 230                 235                 240

Asn Thr Ile Ala Ala Asn
                245

<210> SEQ ID NO 76
<211> LENGTH: 242
<212> TYPE: PRT
<213> ORGANISM: Salmo salar

<400> SEQUENCE: 76

Met Ile Ser Leu Val Phe Val Leu Leu Ile Gly Ala Ala Phe Ala Thr
1               5                   10                  15

Glu Asp Asp Lys Ile Val Gly Gly Tyr Glu Cys Lys Ala Tyr Ser Gln
                20                  25                  30

Ala His Gln Val Ser Leu Asn Ser Gly Tyr His Phe Cys Gly Gly Ser
            35                  40                  45

Leu Val Asn Glu Asn Trp Val Val Ser Ala Ala His Cys Tyr Lys Ser
        50                  55                  60

Arg Val Glu Val Arg Leu Gly Glu His Asn Ile Lys Val Thr Glu Gly
65                  70                  75                  80

Ser Glu Gln Phe Ile Ser Ser Ser Arg Val Ile Arg His Pro Asn Tyr
                85                  90                  95

Ser Ser Tyr Asn Ile Asp Asn Asp Ile Met Leu Ile Lys Leu Ser Lys
                100                 105                 110

Pro Ala Thr Leu Asn Thr Tyr Val Gln Pro Val Ala Leu Pro Thr Ser
            115                 120                 125

Cys Ala Pro Ala Gly Thr Met Cys Thr Val Ser Gly Trp Gly Asn Thr
    130                 135                 140

Met Ser Ser Thr Ala Asp Ser Asn Lys Leu Gln Cys Leu Asn Ile Pro
145                 150                 155                 160

Ile Leu Ser Tyr Ser Asp Cys Asn Asn Ser Tyr Pro Gly Met Ile Thr
                165                 170                 175

Asn Ala Met Phe Cys Ala Gly Tyr Leu Glu Gly Gly Lys Asp Ser Cys
            180                 185                 190

Gln Gly Asp Ser Gly Gly Pro Val Val Cys Asn Gly Glu Leu Gln Gly
        195                 200                 205

Val Val Ser Trp Gly Tyr Gly Cys Ala Glu Pro Gly Asn Pro Gly Val
    210                 215                 220

Tyr Ala Lys Val Cys Ile Phe Asn Asp Trp Leu Thr Ser Thr Met Ala
225                 230                 235                 240

Ser Tyr
```

MODIFIED ENTEROPEPTIDASE PROTEIN

This application is a continuation of U.S. Provisional Application No. 60/852,454.

INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List, or in the text itself; and, each of these documents or references ("herein-cited references"), as well as each document or reference cited in each of the herein-cited references (including any manufacturer's specifications, instructions, etc.), is hereby expressly incorporated herein by reference.

BACKGROUND OF THE INVENTION

The present invention relates to novel enteropeptidase (EP) variant polypeptides derived from Japanese Medaka (*Oryzias latipes*). More particularly, the present invention relates to novel EP variant polypeptides with enhanced substrate specificity, polynucleotides encoding the EP polypeptides, nucleotide constructs, vectors and host cells comprising the polynucleotides, methods for producing the polypeptides and polynucleotides, and kits.

EP (enterokinase, EC 3.4.21.9) is a heterodimeric glycoprotein present in the duodenal and jejunal mucosa and is involved in the digestion of dietary proteins. Specifically, EP catalyzes the conversion, in the duodenal lumen, of trypsinogen into active trypsin via the cleavage of the acidic propeptide from trysinogen (Light et al., *Trends Biochem. Sci.*, 14:110-112 (1989)). The activation of trypsin initiates a cascade of proteolytic reactions leading to the activation of many pancreatic zymogens, including chymotrypsinogen, proelastase, procarboxypeptidases, and some prolipases (Grishan et al., *Gastroenterology*, 85:727-731 (1983)).

To date, studies have reported the molecular cloning of EP from several mammalian sources, including cattle (LaVallie et al., *J. Biol. Chem.*, 268:23311-13317 (1993); Kitamoto et al., *Proc. Natl. Acad. Sci. USA*, 91:7588-7592 (1994)), humans (Kitamoto et al., *Biochemistry*, 34:4562-4568 (1995)), pigs (Matsushima et al., *J. Boil. Chem.*, 269:19976-19982 (1994)), rats (Yahagi et al., *Biochem. Biophys. Res. Commun.*, 219:806-812 (1996)), and mice (Yuan et al., *Am. J. Physiol.*, 274:342-349 (1998)). These studies provided much information on the structural details and organization of EP, and opened a path to further investigation of the molecular properties of this protease. For example, it was reported that the N-terminal heavy-chain is required for efficient activation of trypsinogen by the serine protease domain of the C-terminal light chain (Lu et al., *J. Biol. Chem.*, 272:31293-31300 (1997); Mikhailova et al., *FEBS Lett.*, 442:226-230 (1999)). In addition, a recent study by Lu et al. established the tertiary structure of the bovine EP catalytic domain, thereby demonstrating that Lys99, which is situated in a unique exosite on the enzyme surface, involves in the specific cleavage of trypsinogen and similar peptidyl substrates (Lu et al., *J. Mol. Biol.*, 292:361-373 (1999)). A more recent study reported that a mucin-like domain found in the heavy chain of EP can be a targeting signal for apical sorting of the protein (Zheng et al., *J. Biol. Chem.*, 277:6858-6863 (2002)).

EP is highly specific for the sequence Asp-Asp-Asp-Asp-Lys ($D_4K$) (SEQ ID NO: 1) of trypsinogen (Bricteux-Gregoire et al., *Comp. Biochem. Physiol.*, 42B: 23-39 (1972)). It is generally believed that EP (or enteropeptidase-like enzyme) is present in all vertebrates. This belief comes from the finding that in almost all vertebrate species a short peptide sequence of Asp-Asp-Asp-Asp-Lys ($D_4K$) (SEQ ID NO: 1) is found in the presumed activation site of trypsinogens (14). However, no information on EP in vertebrates other than mammals has been made available to date. EP is highly specific for the sequence Asp-Asp-Asp-Asp-Lys ($D_4K$) (SEQ ID NO: 1) of trypsinogen (Bricteux-Gregoire et al., *Comp. Biochem. Physiol.*, 42B:23-39 (1972)). Because of the high degree of $D_4K$ (SEQ ID NO: 1) specificity, EP has been used as a suitable reagent for cleaving substrate proteins. Indeed, bovine EP has been widely used for this purpose (Collins-Racie et al., *Biotechnology*, 13:982-987 (1995)).

Nonetheless, the conventional system utilizing bovine EP still has significant drawbacks for industrial application due to its nonspecific proteolytic activity. More particularly, while bovine EP protease cleaves at the EP-cleavage site of recombinant fusion proteins, it also simultaneously hydrolyzes other peptide bonds of the proteins to a considerable degree because of its nonspecific proteolytic activity. This causes a seriously low yield of the targeted protein. Such nonspecific activities of bovine EP also can be an obstacle in the preparation of active recombinant proteases where the EP is employed for cleavage of the inactive fusion protein. This is particularly serious when the proteases to be examined are ones with very low activity for synthetic and naturally occurring protein substrates. In addition, such nonspecific activities of bovine EP make it difficult to determine whether the target recombinant proteases have been successfully activated.

Hence there is a need to generate a novel EP variant polypeptide that substantially lacks nonspecific proteolytic activity while retaining its high specificity for $D_4K$ sequence (SEQ ID NO: 1).

SUMMARY OF THE INVENTION

The present inventors have now generated novel EP variant polypeptides from a non-mammalian source, Japanese Medaka, which demonstrates substantially reduced nonspecific proteolytic activity while retaining its high specificity for Asp-Asp-Asp-Asp-Lys ($D_4K$) sequence (SEQ ID NO: 1).

The inventors here report on the isolation of cDNAs encoding EP of the medaka (*Oryzias latipes*), a freshwater teleost, and its expression in the tissues. The present study also describes some enzymatic properties of the catalytic serine protease domain. Surprisingly, the protease domain of medaka EP exhibits very limited amidolytic activity for any of the synthetic peptide substrates tested, indicating that the medaka protease itself is much more highly specific for the Asp-Asp-Asp-Asp-Lys ($D_4K$) (SEQ ID NO: 1), than those of its mammalian counterparts. Various mutant proteases of medaka EP were generated by site-directed mutagenesis. Some of the mutated proteases exhibited cleavage specificity that was stricter than that of the wild-type enzyme, and may prove to be more effective tools for recombinant protein technology.

In a first aspect, the invention provides an isolated nucleic acid molecule selected from the group consisting of a nucleic acid molecule comprising a nucleotide sequence which is at least 75% homologous to the nucleotide sequence SEQ ID NO: 3, or SEQ ID NO: 5, or a complement thereof, a nucleic acid molecule comprising a fragment of at least 15 nucleotides of a nucleic acid comprising the nucleotide sequence of SEQ ID NO: 3, SEQ ID NO: 5, or a complement thereof, a nucleic acid molecule which encodes a polypeptide comprising an amino acid sequence at least about 50% identical to the amino acid sequence of SEQ ID NO:2, or SEQ ID NO:4, a nucleic acid molecule which encodes a fragment of a polypeptide comprising the amino acid sequence of SEQ ID NO:2, or SEQ ID NO:4; wherein the fragment comprises at least 10 contiguous amino acid residues of the amino acid sequence of SEQ ID NO:2 or SEQ ID NO:4, and a nucleic acid molecule which encodes a variant of a polypeptide comprising the amino acid sequence of SEQ ID NO:2, or SEQ ID NO:4; wherein the nucleic acid molecule hybridizes to a complement of a nucleic acid molecule comprising, SEQ ID NO:3 or SEQ ID NO:5, under stringent conditions.

In one embodiment of the first aspect, the isolated nucleic acid molecule is selected from the group consisting of a nucleic acid molecule comprising the nucleotide sequence of SEQ ID NO: 3, SEQ ID NO: 5, or a complement thereof, and a nucleic acid molecule which encodes a polypeptide comprising the amino acid sequence of SEQ ID NO: 2, or SEQ ID NO: 4.

In another embodiment, the nucleic acid further comprises vector nucleic acid sequences. In a further embodiment, the nucleic acid is operably linked to a surrogate promoter. IN another particular embodiment of the aspect, the nucleic acid further comprises nucleic acid sequences encoding a heterologous polypeptide.

In a particular embodiment of the aspect, a host cell contains the nucleic acid molecule of claim 1. In one embodiment, the host cell is selected from the group consisting of: bacterial cells, fungal cells, and animal cells. In a particular embodiment, the bacterial cell is *Escherichia coli*.

In another aspect, the invention provides isolated polypeptides that are selected from the group consisting of a fragment of a polypeptide comprising the amino acid sequence of SEQ ID NO: 2, or SEQ ID NO: 4, wherein the fragment comprises at least 15 contiguous amino acids of SEQ ID NO: 2 or SEQ ID NO: 4, a variant of a polypeptide comprising the amino acid sequence of SEQ ID NO: 2, or SEQ ID NO: 4, wherein the polypeptide is encoded by a nucleic acid molecule which hybridizes to a complement of a nucleic acid molecule comprising, SEQ ID NO:3, or SEQ ID NO:5, under stringent conditions, a polypeptide which is encoded by a nucleic acid molecule comprising a nucleotide sequence which is at least 50% identical to a nucleic acid comprising the nucleotide sequence SEQ ID NO:3, or SEQ ID NO:5, and a polypeptide comprising an amino acid sequence which is at least 30% homologous to the amino acid sequence of, SEQ ID NO:2, or SEQ ID NO:4.

In one embodiment of the aspect, the isolated polypeptides comprise the amino acid sequence of SEQ ID NO: 2, or SEQ ID NO: 4.

In another embodiment of the aspect, the polypeptide comprising the amino acid sequence of SEQ ID NO: 2 has at least one mutation. In a particular embodiment, the mutation is selected from the group consisting of a substitution, deletion, and addition. In a more particular embodiment, the mutation is a substitution. In a further embodiment, the substitution occurs at amino acid residue selected from the group consisting of: residue 93 through residue 193. In another embodiment, the substitution comprises a substitution at one or more residues selected from position 63, 105, 144, 173 or 193. In a particular embodiment, the substitution is at residue 63. In another embodiment, the substitution at residue 63 is selected from the group consisting of: K63R, K63A, and K63E. In a particular embodiment, the substitution is at residue 105. In another embodiment, the substitution at residue 105 is selected from the group consisting of T105A, T105R, and T105E. In a particular embodiment, the substitution is at residue 144. In another embodiment, the substitution at residue 144 is F144S. In another embodiment, the substitution is at residue 173. In a particular embodiment, the substitution at residue 173 is E173A. In another embodiment, the substitution is at residue 193. In another embodiment, the substitution at residue 193 is selected from the group consisting of: P193E and P193A.

In a further embodiment, the isolated polypeptide with E173A substitution consists of the amino acid sequence of SEQ ID NO: 4. In another further embodiment, the isolated polypeptide with E173A substitution comprises the amino acid sequence of SEQ ID NO: 4.

In one embodiment, any of the isolated polypeptides according to any of the aspects described herein is cleavage specific for Asp-Asp-Asp-Asp-Lys (SEQ ID NO: 1).

In another embodiment, any of the isolated polypeptides according to any of the aspects described herein, has low non-specific proteolytic activity. In a further embodiment, the polypeptide has low-specific proteolytic activity for a synthetic peptide substrate. In another further embodiment, the synthetic peptide substrate is a 4-methylcoumaryl-7-amide (MCA)-substrate. In a particular embodiment, the synthetic peptide substrate is selected from the group consisting of: Boc-Glu (OBzl)-Ala-Arg-MCA, Z-Phe-Arg-MCA, and Pro-Phe-Arg-MCA. In a further embodiment, the synthetic peptide substrate consists of a fusion protein. In a more particular embodiment, the fusion protein comprises SEQ ID NO: 1 and another protein.

In another embodiment, the polypeptide has low non-specific proteolytic activity for a biological peptide substrate. In a further embodiment, the biological peptide substrate is selected from the group consisting of: kininogen, fibrinogen, fibronectin, gelatin and laminin. In one embodiment, the biological peptide substrate consists of a recombinant fusion protein. In another embodiment, the recombinant fusion protein comprises SEQ ID NO: 1 and another protein. In a particular embodiment, the recombinant fusion protein is selected from the group consisting of: gelatinaseA, human kallikrein 8 and tissue type plasminogen activator (tPA).

In one aspect, the invention provides an isolated polypeptide comprising the amino acid sequence of SEQ ID NO: 2 that has at least one mutation at one or more residues selected from position 63, 105, 144, 173 or 193, wherein the isolated polypeptide is cleavage specific for Asp-Asp-Asp-Asp-Lys (SEQ ID NO: 1), and has low non-specific proteolytic activity.

In one embodiment, the mutation is a substitution selected from the group consisting of: K63R, K63A, K63E, T105A, T105R, T105E, F144S, E173A, P193A, and P193A. In another particular embodiment of the aspect, the mutation is E173A.

Another aspect of the invention provides an isolated polypeptide comprising the amino acid sequence of SEQ ID NO: 4, wherein the isolated polypeptide is cleavage specific for Asp-Asp-Asp-Asp-Lys (SEQ ID NO: 1), and has low non-specific proteolytic activity.

In another embodiment, the invention provides an isolated polypeptide as described herein, wherein the polypeptide is a recombinant polypeptide.

In still a further embodiment, the invention provides an isolated polypeptide as described herein, wherein the polypeptide has enhanced stability at −20 C, 4 C and 32 C.

In a particular aspect, the invention teaches a method for producing a polypeptide that is selected from the group consisting of a polypeptide comprising the amino acid sequence SEQ ID NO: 2, or SEQ ID NO: 4, a fragment of a polypeptide comprising the amino acid sequence of SEQ ID NO: 2, or SEQ ID NO: 4, wherein the fragment comprises at least 15 contiguous amino acids of SEQ ID NO: 2, or SEQ ID NO: 4, a naturally occurring allelic variant of a polypeptide comprising the amino acid sequence of SEQ ID NO:2, or SEQ ID NO:4, wherein the polypeptide is encoded by a nucleic acid molecule which hybridizes to a complement of a nucleic acid molecule comprising SEQ ID NO:3, or SEQ ID NO:5, under stringent conditions, and where the method comprises culturing the host cells of the invention under conditions in which the nucleic acid molecule is expressed.

In certain embodiments, the polypeptides are produced in an *E. coli* expression system.

Another particular aspect of the invention teaches a method for cleavage of a protein containing an Asp-Asp-Asp-Asp-Lys cleavage site (SEQ ID NO: 1) using any of the polypeptides of the invention described herein, the method comprising contacting the protein with any of the polypeptides of the invention, and wherein the contacting of the protein with the polypeptide results in specific cleavage.

In one embodiment, the protein is a fusion protein. In another embodiment, the fusion protein is a recombinant fusion protein. In a further embodiment, the protein is bacterially produced. In a more particular embodiment, the protein is a synthetic protein.

In a further aspect, the invention teaches a method for the preparation of recombinant protein using any of the polypeptides according to the invention as described herein, the method comprising providing a recombinant fusion protein containing a Asp-Asp-Asp-Asp-Lys cleavage site (SEQ ID NO: 1), and contacting the fusion protein with any of the polypeptides of the invention, wherein contacting the recombinant fusion protein with the polypeptide results in Asp-Asp-Asp-Asp-Lys (SEQ ID NO: 1) specific cleavage and preparation of recombinant protein.

In another aspect, the invention provides a kit comprising any of the polypeptides described herein for use in the cleavage of a protein containing an Asp-Asp-Asp-Asp-Lys cleavage site (SEQ ID NO: 1), and instructions for use.

In one embodiment, the protein is a fusion protein. In another embodiment, the fusion protein is a recombinant fusion protein. In further embodiments, the protein is a bacterially produced protein. In a particular embodiment, the protein is a synthetic protein.

BRIEF DESCRIPTION OF THE DRAWINGS

FIG. 5 (A-C) shows the expression of two distinct EP transcripts in the Medaka intestine. (A) Amino acid sequence alignment of EP-1 (upper) (SEQ ID NO: 71) and EP-2 (lower) (SEQ ID NO: 72) is shown. (B) RT-PCR analysis of the EP-1 and EP-2 transcript was performed using specific primer pairs with total RNAs isolated from the Medaka intestine. A transcript of Medaka cytoplasmic actin-1 (OLCA-1) was amplified as a control. PCR cycle numbers are indicated at the top of the figure. (C) Southern blot analysis was performed using Medaka genomic DNA (20 µg/lane) digested with various restriction enzymes as indicated.

FIG. 6(A-D) shows the in situ detection of EP mRNA in the Medaka ovary. Staining was performed with DIG-labeled antisense (A and C) and sense probes (B and D). (C) The follicles indicated by the box in (A) are shown at higher magnification. (D) The follicles indicated by the box in (B) are shown at higher magnification. Scale bars=500 µm in (A) and (B) and 200 µm in (C) and (D).

DETAILED DESCRIPTION

Figure 1A:
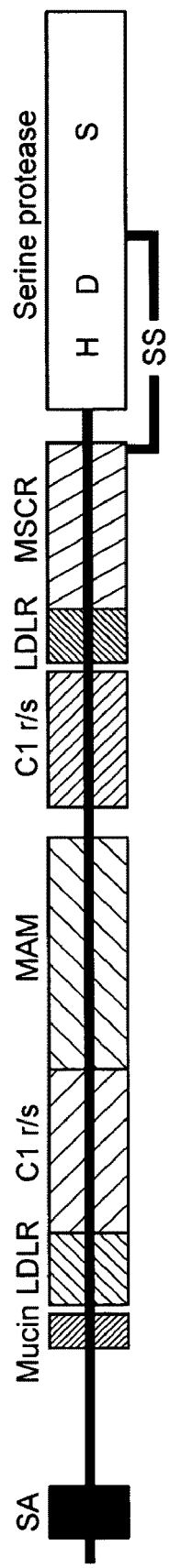
FIG. 1(A) is a schematic representation of the Medaka EP domain structures. Medaka EP consists of a putative signal anchor (SA), a mucin-like domain, a low-density-lipoprotein receptor (LDLR) domain, two complement component C1r or C1s (C1r/s) domains, a MAM domain (named for the motifs found in Meprin, *Xenopus laevis* A5 protein, and protein tyrosine phosphatase µ), a macrophage scavenger receptor (MSCR) domain, and a serine protease domain with active site residues of histidine (H), aspartate (D), and serine (S). The disulfide bond connecting the heavy and light-chain is shown.

The present invention provides novel EP variant polypeptides with enhanced substrate specificity, polynucleotides encoding the polypeptides, nucleotide construct, vectors and host cells comprising the polynucleotides, and methods for producing the polypeptides and polynucleotides.

Described herein is the cloning of cDNAs for enteropeptidase (EP) from the intestine of the medaka, *Oryzias latipes*, which is a small freshwater teleost. The mRNAs code for EP-1 (1043 residues) and EP-2 (1036 residues), both of which have a unique, conserved domain structure of the N-terminal heavy-chain and C-terminal catalytic serine protease light-chain. When compared with mammalian EP serine proteases, the medaka enzyme exhibits extremely low amidolytic activity for small synthetic peptide substrates.

The present invention describes twelve mutated forms of the medaka EP protease that were produced by site-directed mutagenesis. Among them, the mutant protease E173A, was found to have considerably reduced nonspecific hydrolytic activities both for synthetic and protein substrates without serious reduction of its Asp-Asp-Asp-Asp-Lys (D4K)-cleavage activity (SEQ ID NO: 1). For the cleavage of fusion proteins containing an Asp-Asp-Asp-Asp-Lys (D4K)-cleavage site (SEQ ID NO: 1), the medaka EP proteases were shown to have advantages over their mammalian counterparts. Based on the present invention, the mutated forms of the EP protease described by the present invention, including the E173A mutant EP protease, represent an improved proteases for use as a restriction proteases to specifically cleave fusion proteins.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "amino acid sequence" is recited herein to refer to an amino acid sequence of a protein molecule, "amino acid sequence" and like terms are not meant to limit the amino acid sequence to the complete, native amino acid sequence associated with the recited protein molecule; furthermore, an "amino acid sequence" can be deduced from the nucleic acid sequence encoding the protein.

The term "bacterial cell" is meant to include any Gram negative or Gram positive bacterial cell. Typically, Gram-negative bacteria can include *Gluconobacter, Rhizobium, Bradyrhizobium, Alcaligenes, Rhodobacter, Rhodococcus, Azospirillum, Rhodospirillum, Sphingomonas, Burkholderia, Desulfomonas, Geospirillum, Succinomonas, Aeromonas, Shewanella, Halochromatium, Citrobacter, Escherichia, Klebsiella, Zymomonas, Zymobacter,* and *Acetobacter.* Typically, Gram-positive bacteria can include *Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus, Sulfobacillus, Clostridium, Anaerobacter, Eubacterium, Streptococcus, Lactobacillus, Leuconostoc, Enterococcus, Lactococcus, Thermobifida, Cellulomonas,* and *Sarcina.*

The term "coding sequence" is defined herein as a polynucleotide sequence, which directly specifies the amino acid sequence of its protein product. By "fragment" is meant a portion (e.g., at least 5, 10, 25, 50, 100, 125, 150, 200, 250, 300, 350, 400, or 500 amino acids or nucleic acids) of a protein or nucleic acid molecule that is substantially identical to a reference protein or nucleic acid and retains the biological activity of the reference. In some embodiments the portion retains at least 50%, 75%, or 80%, or more preferably 90%, 95%, or even 99% of the biological activity of the reference protein or nucleic acid described herein, and retains at least one biological activity of the reference protein.

The term "fusion protein" as used herein is meant to refer to a protein created through genetic engineering from two or more proteins or peptides. As used herein, a fusion protein can refer to a protein in which a Asp-Asp-Asp-Asp-Lys (D4K) sequence (SEQ ID NO: 1) has been intentionally introduced for specific cleavage. Generally, cleavage of the fusion protein generates two polypeptides. A fusion protein according to the invention can be a recombinant fusion protein. In particular embodiments, a fusion protein can be generated, for example, from the addition of a vector-derived residue peptide at one terminus, for example the N-terminus, in addition to the amino acid sequence of the native. In this way, for example, a recombinant fusion protein can be constructed to have Asp-Asp-Asp-Asp-Lys (D4K) cleavage sites (SEQ ID NO: 1) in the vector and in the protein that contains Asp-Asp-Asp-Asp-Lys (D4K) sites (SEQ ID NO: 1) itself.

The term "homologue", as used herein, refers to a protein or nucleic acid sharing a certain degree of sequence "identity" or sequence "similarity" with a given protein, or the nucleic acid encoding the given protein. The term "percent identity" refers to the percentage of residues in two sequences that are the same when aligned for maximum correspondence. Sequence "similarity" is related to sequence "identity", but differs in that residues that are not exactly the same as each other, but that are functionally "similar" are taken into consideration.

The term "host cell" is meant to include any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

The term "hybridizes under stringent conditions" is intended to describe conditions for hybridization and washing under which nucleotide sequences at least 60%, 70%, 75%, 80%, 85%, 90%, or 95% homologous to each other typically remain hybridized to each other. Hybridization conditions are known to those skilled in the art and can be found in Current Protocols in Molecular Biology, John Wiley & Sons, N.Y., 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

The term "identical" is intended to include a first amino acid or nucleotide sequence which contains a sufficient or minimum number of the same or equivalent amino acid residues or nucleotides, e.g., an amino acid residue which has a similar side chain, to a second amino acid or nucleotide sequence such that the first and second amino acid or nucleotide sequences share common structural domains and/or a common functional activity. Accordingly, a homologous or identical nucleic acid molecule of the invention is at least 10, 15, 20, 25, 30 or more nucleotides in length and hybridizes under stringent conditions to a nucleic acid molecule encoding the amino acid sequence of SEQ ID NO: 2 or to a nucleic acid molecule encoding the amino acid sequence of SEQ ID NO: 4. Preferably, the molecule hybridizes under highly stringent conditions. In other embodiments, the nucleic acid is at least 15-20 nucleotides in length.

The terms "isolated," "purified," or "biologically pure" refer to material that is free to varying degrees from components which normally accompany it as found in its native state. Various levels of purity may be applied as needed according to this invention in the different methodologies set forth herein; the customary purity standards known in the art may be used if no standard is otherwise specified. The enteropeptidase polypeptides of the present invention can be in essentially or substantially pure form. For instance, they are essentially free of other polypeptide material with which it is natively associated. They can also be at least 20% pure, preferably at least 40% pure, more preferably at least 60% pure, even more preferably at least 80% pure, most preferably at least 90% pure, and even most preferably at least 95% pure, as determined by agarose electrophoresis. This can be accomplished by preparing the polypeptide by a variety of means of well-known recombinant methods or by classical purification methods.

By "isolated nucleic acid molecule" is meant a nucleic acid (e.g., a DNA, RNA, or analog thereof) that is free of the genes which, in the naturally occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

The term an "isolated polypeptide" (e.g., an isolated or purified biosynthetic enzyme) is substantially free of cellular material or other contaminating polypeptides from the microorganism from which the polypeptide is derived, or substantially free from chemical precursors or other chemicals when chemically synthesized. The terms "isolated polypeptide" and "isolated protein" refer to compounds comprising amino acids joined via peptide bonds and are used interchangeably. Polypeptide molecules have an amino terminus ("N-terminus") and a carboxy terminus ("C-terminus"). Peptide linkages occur between the backbone amino group of a first amino acid residue and the backbone carboxyl group of a second amino acid residue. Typically, the terminus of a polypeptide at which a new linkage would occur is the carboxy-terminus of the growing polypeptide chain, and polypeptide sequences are written from left to right beginning at the amino terminus.

The term "low" means a reduced amount, or a decreased amount, relative to an unmutated or unaltered nucleotide or polypeptide. Unaltered can mean unmutated. For example, an EP polypeptide of the invention that contains a mutation may have a low proteolytic activity as compared to an EP polypeptide that does not contain the same mutation. In exemplary embodiments the polypeptide has low proteolytic activity, which may be 10%, 15%, 25%, 50%, 75% or even 90% lower than unmutated or unaltered polypeptide.

The phrase "mutant nucleic acid molecule" or "mutant gene" is intended to include a nucleic acid molecule or gene having a nucleotide sequence which includes at least one alteration (e.g., substitution, insertion, deletion) such that the polypeptide or polypeptide that can be encoded by said mutant exhibits an activity that differs from the polypeptide or polypeptide encoded by the wild-type nucleic acid molecule or gene.

As used herein, the term "nucleotide" refers to a nucleoside phosphorylated at one of its pentose hydroxyl groups. The term "nucleoside" in turn refers to a compound consisting of a purine [guanine (G) or adenine (A)] or pyrimidine [thymine (T), uridine (U), or cytidine (C)] base covalently linked to a pentose. The term "polynucleotide" refers to a nucleic acid containing a sequence that is greater than about 100 nucleotides in length. The term "nucleic acid" refers to a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides.

The term "nucleic acid" is intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene can be endogenous to the host cell or can be recombinantly introduced into the host cell, e.g., as a plasmid maintained episomally or a plasmid (or fragment thereof) that is stably integrated into the genome.

The term "operably linked" denotes herein a configuration in which a control sequence is placed at an appropriate position relative to the coding sequence of the polynucleotide sequence such that the control sequence directs the expression of the coding sequence of a polypeptide.

The term "protease" is intended to include any polypeptide/s, alone or in combination with other polypeptides, that break peptide bonds between amino acids of proteins.

The term "proteolytic activity" is meant to refer to the cleavage activity of a substrate by an enzyme. In particular embodiments, the term refers to the enzymatic cleavage by enteropeptidases. In exemplary embodiments, the term is meant to refer to the specific activity of medaka EP for Asp-Asp-Asp-Asp-Lys cleavage sites (SEQ ID NO: 1). "Non-specific proteolytic activity" is meant to refer to cleavage activity that is not directed to a specific cleavage site. "Specific proteolytic activity" is meant to refer to cleavage activity that is directed to a specific cleavage site. Proteolytic activity can be The term "recombinant" is meant the product of genetic engineering or chemical synthesis.

The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). In some embodiments, a recombinant nucleic acid molecule (e.g., a recombinant DNA molecule) includes an isolated nucleic acid molecule or gene of the present invention (e.g., an isolated EP nucleic acid molecule encoding an EP polypeptide) operably linked to regulatory sequences.

By "substantially identical" is meant a protein or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 50%, are more preferably 60%, 70%, 75%, 80%, 85%, 90%, and most preferably 91%, 92%, 93%, 94%, 95%, 96%, 97%, 98%, 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "variant" when used in reference to a polypeptide refers to an amino acid sequence that differs by one or more amino acids from a reference polypeptide.

Enteropeptidase (EP)

Enteropeptidase (EP) is a serine protease enzyme that activates its substrates by cleavage. Enteropeptidase is an intestinal protease that removes an N-terminal fragment from trypsinogen. The remaining active fragment is trypsin. This cleavage initiates a cascade of proteolytic reactions leading to the activation of many pancreatic zymogens. See, for example, Matsushima et al., J. Biol. Chem. 269(31): 19976-19982 (1994), Kitamoto et al., Proc. Nat. Acad. Sci., 91(16): 7588-7592 (1994). Almost all of the trypsinogen sequences known to date contain a highly conserved tetra-aspartate sequence preceding the lysine-isoleucine scissile peptide bond. Although EP is widely considered to play a role in trypsinogen activation in all vertebrate species, there has been no report on EP from non-mammalian species. Japanese Patent Publication No. 2005-253352, incorporated herein by reference, has described an enteropeptidase sequence from the lower vertebrate medaka. However, the present study is thus the first to report on the molecular and biochemical characterizations of EP from medaka.

The amino acid sequence of the fish EP is homologous to those of its mammalian counterparts, with all the structural features found in mammalian EPs being conserved, including various unique domains in the N-terminal heavy-chain. However, the extent of identity varies from domain to domain. LDLR domains 1 and 2, C1 r/s domains 1 and 2, and the MAM domain are highly conserved between medaka and mammalian EP with 45-57% identity, while the identity in the mucin-like and MSCR domain between them is as low as 22%. This fact suggests that the former five domains in the heavy-chain play important roles throughout vertebrate species, although these roles are not known at present. As for the mucin-like and MSCR domain, a remarkable sequence homology is found among mammalian EPs, suggesting a conserved role for their respective domains in the molecular event involving EP in mammalian species. Indeed, a previous study clearly established the importance of the O-glycosylated mucin-like domain of bovine EP in apical targeting of the protein (12). It is not known at present whether the corresponding domain of medaka EP may also play such a role.

The heavy-chain of medaka EP has a hydrophobic segment near the N-terminus. This segment probably serves as a transmembrane anchor, as established for the mammalian EP. Consistent with this notion is the current observation that the 28-kDa immunoreactive protein was detected in the membrane fraction of medaka intestines by specific EP antibodies. The EP was also immunologically detected in the soluble fraction of the intestine. Therefore, as in the case of mammalian EPs, the medaka protease is synthesized as a single-chain zymogen in the intestine. After migrating to the surface of the intestine as a membrane-bound protein, some EP molecules probably undergo proteolytic attack by a protease(s) to generate soluble EP. The adult medaka fish intestinal epithelium is demonstrated to contain most of the cell types (enterocytes, goblet cells, and enteroendocrine cells) observed in the small intestine of other vertebrates, but lacks crypts containing Paneth cells and intestinal stem cells (22). The data presented herein suggests that medaka EP is localized in the enterocytes in the proximal intestinal epithelium.

Since EP is highly specific for the Asp-Asp-Asp-Asp-Lys (D4K) sequence (SEQ ID NO: 1), this motif has been intentionally introduced for the specific cleavage of fusion proteins. Bovine EP serine protease is now widely used for this purpose. The current system utilizing the bovine enzyme works reasonably well in many cases, but requires handling with great care. Often, difficulties are encountered that include (1) Bovine EP protease primarily cleaves at the EP-cleavage site of recombinant fusion proteins. However, other peptide bonds of the proteins are also hydrolyzed to a considerable degree by its nonspecific proteolytic activity. This results in a low yield of the protein in question. (2) For preparing active recombinant proteases, the bovine EP protease employed for cleavage of the inactive fusion protein presents an obstacle. This is particularly serious when the proteases to be examined are ones with very low activity for synthetic and protein substrates. Significant nonspecific activities of bovine EP protease often makes it difficult to determine whether the target recombinant proteases have been successfully activated.

Isolated Nucleic Acid Molecules

Included in the scope of the present invention are isolated nucleic acid molecules. The nucleic acid molecule can be single-stranded or double-stranded DNA. The isolated nucleic acid molecule of the invention can include a nucleic acid molecule which is free of sequences which naturally flank the nucleic acid molecule (i.e., sequences located at the 5' and 3' ends of the nucleic acid molecule) in the chromosomal DNA of the organism from which the nucleic acid is derived. For instance, an isolated nucleic acid molecule can contain less than about 10 kb, 5 kb, 4 kb, 3 kb, 2 kb, 1 kb, 0.5 kb, 0.1 kb, 50 bp, 25 bp or 10 bp of nucleotide sequences which naturally flank the nucleic acid molecule in chromosomal DNA of the microorganism from which the nucleic acid molecule is derived. Moreover, an "isolated" nucleic acid molecule, such as a cDNA molecule, can be substantially free of other cellular materials when produced by recombinant techniques, or substantially free of chemical precursors or other chemicals when chemically synthesized.

In certain embodiments of the invention, the nucleic acid corresponds to enteropeptidase 1 (SEQ ID NO: 3):

```
GTGGTGGGTGGGGTCAATGCTGAAAAGGGGCGTGGCCATGGATGGTGTC
CCTACACTGGAGGGGCGTCATGGCTGTGGTGCCTCACTGATCGGCAGAG
ACTGGTTGCTGACTGCTGCACACTGTGTCTATGGGAAGAACACACACCTG
CAGTACTGGTCAGCTGTTCTTGGCCTTCATGCTCAGAGCAGCATGAACTC
ACAGGAAGTTCAGATCCGGCAGGTGGACCGCATTATCATCAACAAGAACT
ACAACAGAAGAACCAAAGAGGCAGACATCGCCATGATGCACCTGCAGCAG
CCAGTCAACTTCACTGAGTGGGTTCTGCCTGTGTGTTTAGCATCAGAAGA
TCAACATTTTCCAGCTGGAAGAAGGTGTTTCATTGCAGGGTGGGGTCGGG
ACGCTGAAGGAGGATCTCTACCTGACATTCTACAGGAGGCTGAGGTTCCC
CTGGTGGACCAGGATGAGTGCCAGCGTCTCTTACCCGAGTACACCTTCAC
CTCCAGCATGCTATGTGCTGGATATCCTGAAGGCGGAGTTGACTCCTGTC
AGGGTGACTCTGGAGGACCTCTGATGTGCTTAGAAGATGCACGGTGGACT
CTGATTGGTGTGACATCATTTGGCGTTGGCTGTGGGCGTCCTGAGAGACC
TGGAGCTTATGCTCGAGTGTCTGCTTTCACTTCATGGATTGCTGAGACCA
GGCGCTCCTCGTTCTCAGATCTAGACTGA
```

In other embodiments of the invention, the nucleic acid corresponds to the enteropeptidase 1 with a E173A mutation (SEQ ID NO: 5):

```
GTGGTGGGTGGGGTCAATGCTGAAAAGGGGCGTGGCCATGGATGGTGTC
CCTACACTGGAGGGGCGTCATGGCTGTGGTGCCTCACTGATCGGCAGAG
ACTGGTTGCTGACTGCTGCACACTGTGTCTATGGGAAGAACACACACCTG
CAGTACTGGTCAGCTGTTCTTGGCCTTCATGCTCAGAGCAGCATGAACTC
ACAGGAAGTTCAGATCCGGCAGGTGGACCGCATTATCATCAACAAGAACT
ACAACAGAAGAACCAAAGAGGCAGACATCGCCATGATGCACCTGCAGCAG
CCAGTCAACTTCACTGAGTGGGTTCTGCCTGTGTGTTTAGCATCAGAAGA
TCAACATTTTCCAGCTGGAAGAAGGTGTTTCATTGCAGGGTGGGGTCGGG
ACGCTGAAGGAGGATCTCTACCTGACATTCTACAGGAGGCTGAGGTTCCC
```

-continued

```
CTGGTGGACCAGGATGCGTGCCAGCGTCTCTTACCCGAGTACACCTTCAC

CTCCAGCATGCTATGTGCTGGATATCCTGAAGGCGGAGTTGACTCCTGTC

AGGGTGACTCTGGAGGACCTCTGATGTGCTTAGAAGATGCACGGTGGACT

CTGATTGGTGTGACATCATTTGGCGTTGGCTGTGGGCGTCCTGAGAGACC

TGGAGCTTATGCTCGAGTGTCTGCTTTCACTTCATGGATTGCTGAGACCA

GGCGCTCCTCGTTCTCAGATCTAGACTGA
```

In one embodiment, an isolated nucleic acid molecule of the invention comprises a nucleotide sequence which is at least about 50% identical, and most preferably 60%, 65%, 70%, 75%, 80%, 85%, and more preferably 91%, 92%, 93%, 94%, 95%, 96%, 97%, 98%, 99% identical to the nucleotide sequence of SEQ ID NO: 3 or SEQ ID NO: 5, or a complement thereof. In another embodiment, the nucleic acid molecule of the invention comprises a fragment of at least about 5-25, more preferably 10-15 nucleotides of a nucleic acid comprising the nucleotide sequence of SEQ ID NO: 3 or SEQ ID NO: 5, or a complement thereof, that retains the biological activity of SEQ ID NO: 3 or SEQ ID NO: 5, e.g. the fragments have proteolytic activity, and in more specific embodiments, the fragments can cleave at Asp-Asp-Asp-Asp-Lys cleavage sites (SEQ ID NO: 1), and have low non-specific proteolytic activity. The term "low" means a reduced amount, or a decreased amount, relative to an unmutated or unaltered nucleotide or polypeptide. Unaltered can mean unmutated. In exemplary embodiments the polypeptide has low proteolytic activity, which may be 10%, 15%, 25%, 50%, 75% or even 90% lower than unmutated or unaltered polypeptide. In yet another embodiment, an isolated nucleic acid molecule of the invention encodes a nucleic acid molecule which encodes a polypeptide comprising an amino acid sequence that is at least about 50% homologous to the amino acid sequence of SEQ ID NO: 2 or SEQ ID NO: 4, and retains the biological activity of SEQ ID NO: 2 or SEQ ID NO: 4, e.g. retains, for example, proteolytic activity and in more specific embodiments, the fragments can cleave at Asp-Asp-Asp-Asp-Lys cleavage sites (SEQ ID NO: 1), and have low non-specific proteolytic activity. Typically, the terms "sequence identity" or "homologue" include a nucleotide or polypeptide sharing at least about 30-35%, advantageously at least about 35-40%, more advantageously at least about 40-50%, and even more advantageously at least about 60%, 70%, 80%, 90% or more identity with the amino acid sequence of a wild-type polypeptide or polypeptide described herein and having a substantially equivalent functional or biological activity as the wild-type polypeptide or polypeptide. For example, a enteropeptidase homologue shares at least about 30-35%, advantageously at least about 35-40%, more advantageously at least about 40-50%, and even more advantageously at least about 90%, 91%, 92%, 93%, 94%, 95%, 96%, 97%, 98%, 99% identity with the polypeptide having the amino acid sequence set forth as SEQ ID NO: 2 or SEQ ID NO: 4, and has substantially equivalent functional or biological activities (i.e., is a functional equivalent) of the polypeptide having the amino acid sequence set forth as SEQ ID NO: 2 or SEQ ID NO: 4 (e.g., has a substantially equivalent enteropeptidase activities).

In another embodiment, an isolated nucleic acid molecule encodes a variant of a polypeptide comprising the amino acid sequence of SEQ ID NO: 2 or SEQ ID NO: 4, wherein the nucleic acid molecule hybridizes to a complement of a nucleic acid molecule comprising SEQ ID NO: 3 or SEQ ID NO: 5, under stringent conditions. Such stringent conditions are known to those skilled in the art and can be found in Current Protocols in Molecular Biology, John Wiley & Sons, N.Y. (1989), 6.3.1-6.3.6. A particular, non-limiting example of stringent (e.g. high stringency) hybridization conditions are hybridization in 6× sodium chloride/sodium citrate (SSC) at about 45° C., followed by one or more washes in 0.2×SSC, 0.1% SDS at 50-65° C. Advantageously, an isolated nucleic acid molecule of the invention that hybridizes under stringent conditions to the sequence of SEQ ID NO: 3 or SEQ ID NO: 5 corresponding to a naturally-occurring nucleic acid molecule or a naturally occurring allelic variant. Typically, a naturally-occurring nucleic acid molecule includes an RNA or DNA molecule having a nucleotide sequence that occurs in nature.

Modification of a nucleotide sequence encoding a polypeptide of the present invention may be necessary for the synthesis of polypeptides substantially identical or similar to the polypeptide. The terms "substantially identical" or "substantially similar" to the polypeptide can refer to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 5, e.g., a subsequence thereof, and/or by introduction of nucleotide substitutions which do not give rise to another amino acid sequence of the polypeptide encoded by the nucleotide sequence. For a general description of nucleotide substitution, see, e.g., Ford et al., Protein Expression and Purification, 2:95-107 (1991).

A nucleic acid molecule of the present invention (e.g., a nucleic acid molecule having the nucleotide sequence of SEQ ID NO: 3 or SEQ ID NO: 5, can be isolated using standard molecular biology techniques and the sequence information provided herein. For example, nucleic acid molecules can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989) or can be isolated by the polymerase chain reaction using synthetic oligonucleotide primers designed based upon the sequence of SEQ ID NO: 3 or SEQ ID NO: 5. A nucleic acid of the invention can be amplified using cDNA, mRNA or alternatively, genomic DNA, as a template and appropriate oligonucleotide primers according to standard PCR amplification techniques.

In one embodiment, an isolated nucleic acid molecule of the invention is selected from the group consisting of a nucleic acid molecule comprising the nucleotide sequence of SEQ ID NO: 3 or SEQ ID NO: 5, or a complement thereof; and a nucleic acid molecule which encodes a polypeptide comprising the amino acid sequence of SEQ ID NO: 2 or SEQ ID NO: 4.

In another embodiment, the invention provides an isolated polynucleotide encoding a polypeptide, wherein the polynucleotide is a recombinant polynucleotide.

A recombinant polynucleotide can be a fusion. For example, a nucleic acid described herein (e.g., an EP nucleic acid) is expressed as a transcriptional or translational fusion with a detectable reporter, and expressed in an isolated cell (e.g., mammalian or insect cell) under the control of a heterologous promoter, such as an inducible promoter.

Host Cells

In another embodiment, the present invention provides a host cell. A host cell includes any cell type which is susceptible to transformation, transfection, or transduction with a nucleic acid construct or expression vector comprising a polynucleotide of the present invention. Host cells for use in expressing the EP polypeptides encoded by the expression vectors of the present invention include, but are not limited to, bacterial cells, such as *E. coli*; fungal cells, such as yeast cells (e.g., *Saccharomyces cerevisiae*); and animal cells such as CHO. Appropriate culture mediums and conditions for the above-described host cells are well known in the art.

Isolation and Cloning

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well-known polymerase chain reaction ("PCR") or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleotide sequence-based amplification (NASBA) may be used.

Amplification is the production of additional copies of a nucleic acid sequence and is generally carried out using PCR technologies well known in the art (Dieffenbach and G S Dvekler, PCR Primer, a Laboratory Manual, Cold Spring Harbor Press, Plainview N.Y. (1995)). Polymerase chain reaction ("PCR") refers to the methods disclosed in U.S. Pat. Nos. 4,683,195, 4,683,202 and 4,965,188, all of which are incorporated herein by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter.

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxyribonucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

A "primer" refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced (i.e., in the presence of nucleotides, an inducing agent such as DNA polymerase, and under suitable conditions of temperature and pH). The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method.

A probe refers to an oligonucleotide (i.e., a sequence of nucleotides), whether occurring naturally or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that the probe used in the present invention is labeled with any "reporter molecule," so that it is detectable in a detection system, including, but not limited to enzyme (i.e., ELISA, as well as enzyme-based histochemical assays), fluorescent, radioactive, and luminescent systems. It is not intended that the present invention be limited to any particular detection system or label. The terms "reporter molecule" and "label" are used herein interchangeably. In addition to probes, primers and deoxynucleoside triphosphates may contain labels; these labels may comprise, but are not limited to, $^{32}$P, $^{33}$P, or fluorescent molecules (e.g., fluorescent dyes).

As used herein, the terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists. J. Sambrook et al., Molecular Cloning: A Laboratory Manual, Cold Spring Harbor Press, NY, 9.31-9.58. (1989)

As used herein, the term "Northern blot analysis" and "Northern blot" and "Northern" as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists. J. Sambrook et al., supra, pp 7.39-7.52.

As used herein, the terms "Western blot analysis" and "Western blot" and "Western" refers to the analysis of protein(s)(or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

Isolated Polypeptides

Another aspect of the present invention features isolated enteropeptidase polypeptides (e.g., isolated enteropeptidase-1 polypeptides).

An isolated or purified polypeptide (e.g., an isolated or purified EP-1) is substantially free of cellular material or other contaminating polypeptides from the microorganism from which the polypeptide is derived, or substantially free from chemical precursors or other chemicals when chemically synthesized.

Included within the scope of the present invention are EP-1 polypeptides or genes products that are mammalian derived polypeptides or gene products. In a preferred embodiment, the EP-1 polypeptide or gene product is derived from the teleost Medaka. Further included within the scope of the present invention are EP-1 polypeptides or gene products that can be non-mammalian or mammalian derived polypeptides or gene products which differ from naturally-occurring EP-1 genes or polypeptides, for example, genes which have nucleic acids that are mutated, inserted or deleted, but which encode polypeptides substantially similar to the naturally-occurring gene products of the present invention, e.g., are cleavage specific for Asp-Asp-Asp-Asp-Lys (SEQ ID NO: 1), and has low non-specific proteolytic activity. Low non-specific proteolytic activity is meant to refer to a reduced amount, or a decreased amount, relative to an unmutated or unaltered nucleotide or polypeptide. Unaltered can mean unmutated. In exemplary embodiments the polypeptide has low proteolytic activity, which may be 10%, 15%, 25%, 50%, 75% or even 90% lower than unmutated or unaltered polypeptide.

In particular embodiments of the invention, the isolated polypeptide encodes EP-1, having SEQ ID NO: 2:

VVGGVNAEKGAWPWMVSLHWRGRHGCGASLIGRDWLLTAAHCVYGKNTHL

QYWSAVLGLHAQSSMNSQEVQIRQVDRIIINKNYNRRTKEADIAMMHLQQ

PVNFTEWVLPVCLASEDQHFPAGRRCFIAGWGRDAEGGSLPDILQEAEVP

LVDQDECQRLLPEYTFTSSMLCAGYPEGGVDSCQGDSGGPLMCLEDARWT

LIGVTSFGVGCGRPERPGAYARVSAFTSWIAETRRSSFSDLD*

In other particular embodiments of the invention, the isolated polypeptide encodes EP-1 with E173A mutation, having SEQ ID NO: 4:

VVGGVNAEKGAWPWMVSLHWRGRHGCGASLIGRDWLLTAAHCVYGKNTHL

QYWSAVLGLHAQSSMNSQEVQIRQVDRIIINKNYNRRTKEADIAMMHLQQ

PVNFTEWVLPVCLASEDQHFPAGRRCFIAGWGRDAEGGSLPDILQEAEVP

LVDQDACQRLLPEYTFTSSMLCAGYPEGGVDSCQGDSGGPLMCLEDARWT

LIGVTSFGVGCGRPERPGAYARVSAFTSWIAETRRSSFSDLD*

It is well understood that one of skill in the art can mutate (e.g., substitute) nucleic acids which, due to the degeneracy of the genetic code, encode for an identical amino acid as that encoded by the naturally occurring gene. This may be desirable in order to improve the codon usage of a nucleic acid. Moreover, it is well understood that one of skill in the art can mutate (e.g., substitute) nucleic acids which encode for conservative amino acid substitutions. It is further well understood that one of skill in the art can substitute, add or delete amino acids to a certain degree without substantially affecting the function of a gene product (e.g., a cleavage specific activity, for example cleavage specificity for Asp-Asp-Asp-Asp-Lys (SEQ ID NO: 1)) as compared with a naturally-occurring gene product, each instance of which is intended to be included within the scope of the present invention.

In an embodiment of the invention, the isolated nucleic acid molecule of the invention is selected from a nucleic acid molecule comprising the nucleotide sequence of SEQ ID NO: 3 or SEQ ID NO: 5, or a complement thereof. In another embodiment of the invention the nucleic acid molecule encodes a polypeptide comprising the amino acid sequence of SEQ ID NO: 2 or SEQ ID NO: 4.

Included in the scope of the invention are isolated polypeptides (e.g., an isolated EP polypeptide, more specifically an isolated EP-1 polypeptide that comprise a fragment of a polypeptide comprising the amino acid sequence of SEQ ID NO: 2 or SEQ ID NO: 4, wherein the fragment comprises at least 5-15 contiguous amino acids of SEQ ID NO: 2 or SEQ ID NO: 4 and retains at least one biological activity of the reference polypeptide that is cleavage specific for Asp-Asp-Asp-Asp-Lys (SEQ ID NO: 1), and has low non-specific proteolytic activity.

Also included in the scope of the invention are a variant or naturally occurring allelic variant of a polypeptide comprising the amino acid sequence of SEQ ID NO: 2 or SEQ ID NO: 4, wherein the polypeptide is encoded by a nucleic acid molecule which hybridizes to a complement of a nucleic acid molecule comprising SEQ ID NO: 3 or SEQ ID NO: 5 under stringent conditions.

Modification of a nucleotide sequence encoding a polypeptide of the present invention may be necessary for the synthesis of polypeptides substantially identical or similar to the polypeptide. The terms "substantially identical" or "substantially similar" to the polypeptide can refer to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 5, e.g., a subsequence thereof, and/or by introduction of nucleotide substitutions which do not give rise to another amino acid sequence of the polypeptide encoded by the nucleotide sequence. For a general description of nucleotide substitution, see, e.g., Ford et al., Protein Expression and Purification, 2:95-107 (1991).

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis. See, e.g., Cunningham and Wells, Science, 244: 1081-1085 (1989). In the latter technique, mutations are introduced at every positively charged residue in the molecule, and the resultant mutant molecules are tested for antimicrobial activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling. See, e.g., de Vos et al., Science, 255:306-312 (1992); Smith et al., Journal of Molecular Biology, 224:899-904 (1992); Wlodaver et al., FEBS Letters, 309:59-64 (1992).

In other embodiments, an isolated polypeptide of the present invention comprises an amino acid sequence which is a homologue of the at least one of the polypeptides set forth as SEQ ID NO: 2 or SEQ ID NO: 4 (e.g., comprises an amino acid sequence at least about 30-40% identical, advantageously about 40-50% identical, more advantageously about 50-60% identical, and even more advantageously about 90%, 91%, 92%, 93%, 94%, 95%, 96%, 97%, 98%, 99% identical to the amino acid sequence of SEQ ID NO: 2 or SEQ ID NO: 4, and has an activity that is substantially similar to that of the polypeptide encoded by the amino acid sequence of SEQ ID NO: 2 or SEQ ID NO: 4, respectively, for example is cleavage specific for Asp-Asp-Asp-Asp-Lys (SEQ ID NO: 1), and has low non-specific proteolytic activity.

To determine the percent identity of two amino acid sequences or of two nucleic acids, the sequences are aligned for optimal comparison purposes. (e.g., gaps can be introduced in the sequence of a first amino acid or nucleic acid sequence for optimal alignment with a second amino or nucleic acid sequence). When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions×100), advantageously taking into account the number of gaps and size of said gaps necessary to produce an optimal alignment.

The comparison of sequences and determination of percent identity between two sequences can be accomplished using a mathematical algorithm. A particular, non-limiting example of a mathematical algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to nucleic acid molecules of the invention. BLAST polypeptide searches can be performed with the XBLAST program, score=50, wordlength=3 to obtain amino acid sequences homologous to polypeptide molecules of the invention. To obtain gapped alignments for comparison purposes, Gapped BLAST can be utilized as described in Altschul et al. (1997) *Nucleic Acids Research* 25(17): 3389-3402. When utilizing BLAST and Gapped BLAST programs, the default parameters of the respective programs (e.g., XBLAST and NBLAST) can be used. Another particular, non-limiting example of a mathematical algorithm utilized for the comparison of sequences is the algorithm of Myers and Miller (1988) *Comput Appl Biosci.* 4:11-17. Such an algorithm is incorporated into the ALIGN program available, for example, at the GENESTREAM network server, IGH Montpellier, FRANCE or at the ISREC server. When utilizing the ALIGN program for comparing amino acid sequences, a PAM120 weight residue table, a gap length penalty of 12, and a gap penalty of 4 can be used.

In another embodiment, the percent identity between two amino acid sequences can be determined using the GAP program in the GCG software package, using either a Blossom 62 matrix or a PAM250 matrix, and a gap weight of 12, 10, 8, 6, or 4 and a length weight of 2, 3, or 4. In yet another embodiment, the percent homology between two nucleic acid sequences can be accomplished using the GAP program in the GCG software package, using a gap weight of 50 and a length weight of 3.

Also included in the scope of the invention are isolated polypeptides comprising a fragment of SEQ ID NO: 2 or SEQ ID NO: 4, wherein the amino acids of the fragment are arranged in any sequence such that the fragment is cleavage specific for Asp-Asp-Asp-Asp-Lys (SEQ ID NO: 1), and has the low non-specific proteolytic activity of SEQ ID NO:2 or SEQ ID NO:4

It is well understood that also included in the scope of the invention are synthetic or recombinant polypeptides.

In another preferred embodiment of the invention are provided isolated EP polypeptides comprising an amino acid sequence which is a variant of the polypeptide of SEQ ID NO: 2. As used herein, the term "variant" when used in reference to a polypeptide refers to an amino acid sequence that differs by one or more amino acids from a reference polypeptide. The variant may have "conservative" changes, wherein a substituted amino acid has similar structural or chemical properties. More rarely, a variant may have "non-conservative" changes. Similar minor variations may also include amino acid deletions or insertions, or both. An EP variant polypeptide and polynucleotide encoding the same can be generated using any technique known in the art, including site-directed mutagenesis. See, e.g., Ling et al., "Approaches to DNA mutagenesis: an overview," *Anal. Biochem.* 254(2):157-78 (1997); Dale et al., "Oligonucleotide-directed random mutagenesis using the phosphorothioate method," *Methods Mol. Biol.*, 57:369-74 (1996); Smith, "In vitro mutagenesis," *Ann. Rev. Genet.*, 19:423-462 (1985); Botstein et al., "Strategies and applications of in vitro mutagenesis," *Science*, 229:1193-1201 (1985); Carter, "Site-directed mutagenesis," *Biochem. J*, 237: 1-7 (1986); Kramer et al., "Point Mismatch Repair," *Cell*, 38:879-887 (1984); Wells et al., "Cassette mutagenesis: an efficient method for generation of multiple mutations at defined sites," *Gene*, 34:315-323 (1985); Minshull et al., "Protein evolution by molecular breeding," *Current Opinion in Chemical Biology*, 3:284-290 (1999); Christians et al., "Directed evolution of thymidine kinase for AZT phosphorylation using DNA family shuffling," *Nature Biotechnology*, 17:259-264 (1999); Crameri et al., "DNA shuffling of a family of genes from diverse species accelerates directed evolution," *Nature*, 391:288-291; Crameri et al., "Molecular evolution of an arsenate detoxification pathway by DNA shuffling," *Nature Biotechnology*, 15:436-438 (1997); Zhang et al., "Directed evolution of an effective fructosidase from a galactosidase by DNA shuffling and screening," *Proceedings of the National Academy of Sciences, U.S.A.*, 94:45-4-4509; Crameri et al., "Improved green fluorescent protein by molecular evolution using DNA shuffling," *Nature Biotechnology*, 14:315-319 (1996); Stemmer, "Rapid evolution of a protein in vitro by DNA shuffling," *Nature*, 370:389-391 (1994); Stemmer, "DNA shuffling by random fragmentation and reassembly: In vitro recombination for molecular evolution," *Proceedings of the National Academy of Sciences, U.S.A.*, 91:10747-10751 (1994); WO 95/22625; WO 97/0078; WO 97/35966; WO 98/27230; WO 00/42651; WO 01/75767 and U.S. Pat. No. 6,537,746 which issued to Arnold et al. on Mar. 25, 2003 and is entitled "Method for creating polynucleotide and polypeptide sequences." To maximize any diversity, several of the above-described techniques can be used in combination.

EP variant polypeptides of the present invention can be prepared, for example, by using a wild-type EP polypeptide as a starting material to be improved. The term "wild-type" as applied to a polynucleotide means that the nucleic acid fragment does not comprise any mutations from the form isolated from nature. The term "wild-type" as applied to a polypeptide (or protein) means that the protein will be active at a level of activity found in nature and typically will comprise the amino acid sequence as found in nature. In contrast, the term "modified" or "mutant" when made in reference to a polynucleotide or polypeptide (or protein), respectively, to a polynucleotide or to a polypeptide (or protein) which displays modifications in sequence and/or functional properties (i.e., altered characteristics) when compared to the wild-type polynucleotide or polypeptide. Thus, the term "wild type" indicates a starting or reference sequence prior to a manipulation of the invention.

Suitable sources of wild-type EP can be identified by screening genomic libraries of organisms for the EP activities described herein. In the present invention, a parental amino acid or nucleic acid sequence encoding the wild-type Medaka EP polypeptide was constructed. The sequence designated EP-1 (SEQ ID NO: 3 or 4) was utilized as the starting point for all experiments and library construction.

Also included in the scope of the invention are the isolated polypeptides described herein, wherein the polypeptide comprising the amino acid sequence of SEQ ID NO: 2 has at least one mutation. In certain embodiment, the mutation can be a substitution, deletion, or an addition. In exemplary embodiments, the mutation is a substitution. The substitution can occur anywhere in SEQ ID NO: 2, but preferably the substitution occurs at amino acid residue selected from the group consisting of: residue 93 through residue 193. In exemplary embodiments, the substitution comprises a substitution at one or more residues selected from position 63, 105, 144, 173 or 193. In exemplary embodiments, the substitution is at residue 63, and consists of K63R, K63A or K63E. In other exemplary embodiments, the substitution is at residue105, and consists of T105A, T105R, or T105E. In other exemplary embodiments, the substitution is at residue 144, and consists of F144S. In other exemplary embodiments, the substitution is at residue 173, and consists of E173A. In other exemplary embodiments, the substitution is at residue 193, and consists of P193E or P193A.

Based on the foregoing isolated enteropeptidase polypeptides, immunospecific antibodies can be raised against a EP polypeptide, or portions thereof as described herein, using standard techniques known in the art.

Methods of the Invention

In one embodiment of the present invention are methods for producing any of the polypeptides of the invention, for example a polypeptide comprising the amino acid sequence SEQ ID NO: 2, or SEQ ID NO: 4, a fragment of a polypeptide comprising the amino acid sequence of SEQ ID NO: 2, or SEQ ID NO: 4; wherein the fragment comprises at least 15 contiguous amino acids of SEQ ID NO: 2, or SEQ ID NO: 4, a naturally occurring allelic variant of a polypeptide comprising the amino acid sequence of SEQ ID NO:2, or SEQ ID NO:4, wherein the polypeptide is encoded by a nucleic acid molecule which hybridizes to a complement of a nucleic acid molecule comprising SEQ ID NO:3, or SEQ ID NO:5, under stringent conditions. The method for producing the above-mentioned polypeptides comprises culturing the host cells of the invention under conditions in which the nucleic acid molecule is expressed.

The term "nucleotide construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is inclusive of the term expression cassette or expression vector when the nucleic acid construct contains all the control sequences required for expression of a coding sequence (polynucleotide) of the present invention.

The term "coding sequence" is defined herein as a polynucleotide sequence, which directly specifies the amino acid sequence of its protein product. The boundaries of a genomic coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

The term control sequence includes all components, which are necessary or advantageous for the expression of a polynucleotide encoding a polypeptide of the present invention. Each control sequence may be native or foreign to the nucleotide sequence encoding the polypeptide or native or foreign to each other. Such control sequences may include, but are not limited to, a promoter, and transcriptional and translational stop signals. The control sequence may be an appropriate promoter sequence. The promoter sequence is a relatively short nucleic acid sequence that is recognized by a host cell for expression of the longer coding region that follows. The promoter sequence contains transcriptional control sequences, which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

The term "operably linked" denotes herein a configuration in which a control sequence is placed at an appropriate position relative to the coding sequence of the polynucleotide sequence such that the control sequence directs the expression of the coding sequence of a polypeptide.

The present invention provides an expression vector comprising the polynucleotide described above. The term "expression" includes any step involved in the production of the polypeptide including, but not limited to, transcription, post-transcriptional modification, translation, post-translational modification, and secretion. The term "expression vector" is defined herein as a linear or circular DNA molecule that comprises a polynucleotide encoding a polypeptide of the invention, and which is operably linked to additional nucleotides that provide for its expression.

In particular embodiments of the methods for producing any of the polypeptides of the invention, the polypeptide is produced in an *E. coli* expression system.

In one embodiment, the various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector which, exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

Preferably, the expression vector contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The procedures used to ligate the elements described above to construct the recombinant nucleic acid construct and expression vectors of the present invention are well known to one skilled in the art. See, e.g., J. Sambrook et al., Molecular Cloning, A Laboratory Manual, 2nd edition, Cold Spring Harbor, N.Y. (1989)

Manipulation of the isolated polynucleotide prior to its insertion into a vector may be desirable or necessary depending on the expression vector. An isolated polynucleotide encoding the EP polypeptides of the present invention may be manipulated in a variety of ways well known in the art to provide for expression of the polypeptide.

In certain embodiments, the host cell of the invention contains any of the nucleic acid molecules as described herein. In exemplary embodiments, the host cell is a bacterial cell. In certain embodiments, the bacterial cell is *Escherichia coli*.

Engineered host cells can be cultured in conventional nutrient media modified as appropriate for activating promoters, selecting transformants or amplifying the polynucleotides of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Also included in the methods of the invention are methods for cleavage of a protein containing an Asp-Asp-Asp-Asp-Lys cleavage site (SEQ ID NO: 1) with any of the EP-1 polypeptides of the invention as described herein, the method comprising contacting the protein with any of the polypeptides of claims 1-44, and wherein the contacting of the protein with the polypeptide results in specific cleavage. The protein that is the target for the EP-1 polypeptide, e.g. the protein that contains an Asp-Asp-Asp-Asp-Lys cleavage site (SEQ ID NO: 1) can be a fusion protein, a recombinant fusion protein. A fusion protein is a protein created through genetic engineering from two or more proteins/peptides. This can be achieved by creating a fusion gene: removing the stop codon from the DNA sequence of the first protein, then appending the DNA sequence of the second protein in frame. That DNA sequence will then be expressed by a cell as a single protein. A fusion protein can refer to a protein in which a Asp-Asp-Asp-Asp-Lys (D4K) sequence (SEQ ID NO: 1) has been intentionally introduced for specific cleavage. Generally, cleavage of the fusion protein generates two polypeptides. A fusion protein according to the invention can be a recombinant fusion protein. In particular embodiments, a fusion protein can be generated, for example, from the addition of a vector-derived residue peptide at one terminus, for example the N-terminus, in addition to the amino acid sequence of the native. In this way, for example, a recombinant fusion protein can be constructed to have Asp-Asp-Asp-Asp-Lys (D4K) cleavage sites (SEQ ID NO: 1) in the vector and in the protein that contains Asp-Asp-Asp-Asp-Lys (D4K) sites (SEQ ID NO: 1) itself. In certain embodiment, the recombinant fusion protein can be selected from, but not limited to, gelatinaseA, human kallikrein 8 and tissue type plasminogen activator (tPA). The protein can be bacterially produced. Also included in the scope of the invention are synthetic proteins.

Also included in the methods of the invention are methods for the preparation of a recombinant protein using any of the polypeptides of the invention as described herein, the method comprising providing a recombinant fusion protein containing a Asp-Asp-Asp-Asp-Lys cleavage site (SEQ ID NO: 1), and then contacting the fusion protein with any of the polypeptides according to the invention, wherein contacting the recombinant fusion protein with the polypeptide results in Asp-Asp-Asp-Asp-Lys (SEQ ID NO: 1) specific cleavage and preparation of recombinant protein.

Kits

The present polypeptides may be assembled into kits Included in the invention are kits comprising any of the polypeptides of the invention as described herein, e.g. enteropeptidase polypeptides that are cleavage specific for Asp-Asp-Asp-Asp-Lys (SEQ ID NO: 1), and have low non-specific proteolytic activity. In exemplary embodiments, the kits containing the polypeptides are used for cleavage of proteins containing an Asp-Asp-Asp-Asp-Lys cleavage site (SEQ ID NO: 1), and instructions for use. The kits can be used for cleavage of a fusion protein. Alternatively, the kits can be used for the cleavage of a recombinant fusion protein. In other embodiments, the kits can be used for the cleavage of a bacterially produced protein. The kits can also be used for the cleavage of a synthetic protein. The proteins suitable for cleavage by the polypeptides of the invention contain Asp-Asp-Asp-Asp-Lys cleavage sites (SEQ ID NO: 1).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention.

Having now generally described the invention, the same will be more readily understood through reference to the following Examples, which are provided by way of illustration, and are not intended to be limiting of the present invention, unless specified.

EXAMPLES

Methods of the Invention

The results reported herein were obtained using the following Materials and Methods cDNA Cloning of Medaka Trypsinogen.

For medaka trypsinogen, two degenerate oligonucleotide PCR primers were synthesized based on the cDNA sequence for conserved regions in serine protease (sense primer: 5'-GT(G/T)(C/G) T(C/G/T)(A/T) C(A/T) GCTGC(C/T) CACTG-3' (SEQ ID NO: 7), which corresponds to the amino acid sequence NH2-Val-Leu-Thr-Ala-Ala-His-Cys-COOH (SEQ ID NO: 8); and antisense primer: 5'-(A/T) GGGCC (A/T) CC (A/T/G) GAGTC (A/T) CC-3' (SEQ ID NO: 9), which corresponds to the amino acid sequence NH2-Gly-Asp-Ser-Gly-Gly-Pro-COOH (SEQ ID NO: 10)). cDNAs were PCR-amplified under the conditions described for EP in the main text. A 435-bp fragment was subcloned into pBluescript (II) KS+ (Stratagene, La Jolla, Calif.) and sequenced.

A 5' portion of medaka trypsinogen was obtained by the 5'-RACE method (1) using the 5'-RACE system, Version 2.0 (Invitrogen, Carlsbad, Calif.). The antisense primers used were 5'-AGGAGGTGATGAACTG-3' (SEQ ID NO: 11) (GSP-1; nucleotides 273 to 288, AB272106), 5'-CTCGGTTCCGTCATTGTTCCGGGAT-3' (SEQ ID NO: 12) (GSP-2; nucleotides 249 to 272, AB272106) and 5'-CCAGACGCACCTCCACTCGGGACT-3' (SEQ ID NO: 13) (nested GSP; nucleotides 214 to 237, AB272106). The two rounds of PCR reactions were performed under the conditions of 35 cycles of 0.5 min at 94° C., 0.5 min at 55° C., and 1 min at 72° C. for the first PCR and 35 cycles of 0.5 min at 94° C., 0.5 min at 60° C., and 1 min at 72° C. for the second PCR. The amplified products were then subcloned into pBluescript II plasmid (Stratagene) and sequenced.

A 3' portion of medaka trypsinogen was obtained by the 3'-RACE method (1) using the 3'-Full RACE Core Set (Takara, Tokyo, Japan). The sense primers used were 5'-CATGATCACCAACTCCATGTTCTG-3' (SEQ ID NO: 14) (RACE1; nucleotides 545 to 568, AB272106) and 5'-TGGATACCTGGAGGGAGG-3' (SEQ ID NO: 15) (RACE2; nucleotides 572 to 589, AB272106). The two rounds of PCR reactions were performed under the conditions of 35 cycles of 0.5 min at 94° C., 0.5 min at 55° C., and 1 min at 72° C. for the first PCR and 35 cycles of 0.5 min at 94° C., 0.5 min at 57° C., and 1 min at 72° C. for the second PCR. The amplified products were then subcloned into pBluescript II plasmid (Stratagene) and sequenced.

RT-PCR Analysis of EP Transcripts.

To identify two distinct EP transcripts, enteropeptidase-1 (EP-1) and enteropeptidase-2 (EP-2), expressed in the medaka intestine, RT-PCR was conducted with KOD plus DNA polymerase (Toyobo, Osaka, Japan) using medaka intestine total RNA. The primers used were 5'-AGAACAT-CACAGGTGAACCGGTGA-3' (SEQ ID NO: 16) (sense primer, nucleotides 1-24, AB272104) and 5'-TTCTGACATTCCTGAAGGGACAGC-3' (SEQ ID NO: 17) (antisense primer, nucleotides 3930-3953, AB272104). PCR conditions were 2 min at 94° C. for heating, followed by 30 cycles of 30 sec at 94° C. for denaturing, 15 sec at 60° C. for annealing and 6 min at 68° C. for extension. The products were sequenced as described above. In some experiments, RT-PCR analyses were performed using specific primers: 5'-CAAGAACTACAACAGAAGAA-3' (SEQ ID NO: 18) (sense) and 5'-GTGTATTGAGAAAAAGGTTGTTAA-3' (SEQ ID NO: 19) (antisense) for EP-1 (nucleotides 2719-3415, AB272104) and 5'-CAAGAACTACAACAGAAGAA-3' (SEQ ID NO: 18) (sense) and 5'-CTGTACTAAGAAAAAATTTGTCAT-3' (SEQ ID NO: 20) (antisense) for EP-2 (nucleotides 2747-3443, AB272105). PCR conditions were 3 min at 94° C. for heating, followed by 20, 22, 24, 26 and 28 cycles of 30 sec at 94° C. for denaturing, 30 sec at 60° C. for annealing and 30 sec at 72° C. for extension.

For ovary 1.5- and 1.3-kb EP transcripts, RACE methods (1) were used. The sequence of the 5'-end was confirmed by the 5'-RACE using a 5'-RACE system (Invitrogen). The primers used were as follows: 5'-AGGTAACCAAGCAGAG-3' (SEQ ID NO: 21) (nucleotides 3207-3222, AB272104) for the reverse transcriptase reaction, 5'-GAGAACGAGGAGCGCCTGGTCTCA-3' (SEQ ID NO: 22) (nucleotides 3169-3192, AB272104) for the first PCR, and 5'-ATCCATGAAGTGAAAGCAGACACT-3' (SEQ ID NO: 23) (nucleotides 3142-3165, AB272104) for the second PCR. The PCR was performed under the conditions of 35 cycles of 30 sec at 94° C., 30 sec at 55° C., and 2 min at 72° C. The 3'-end of the transcripts was determined by the 3'-RACE method (1). 3'-RACE was conducted using a 3'-Full RACE Core Set (Takara) as described above.

RT-PCR Detection of EP mRNA in the Gastrointestinal Tract.

The gastrointestinal tract was obtained from mature medaka (body sizes, 3-4 cm), and divided into 8 pieces (about 0.5 mm each). Specimens from five fish were combined for total RNA preparation. Aliquots of 2 μg of the total RNAs were used for reverse transcription. PCR was performed for 25 cycles using Ex Taq DNA polymerase (Takara) and the primers 5'-AGGACCAAACGGAACATTTC-3' (SEQ ID NO: 24) (sense, nucleotides 802-821, AB272104) and 5'-GAGAGGGACGCAGGAGGA-3' (SEQ ID NO: 25) (antisense, 1422-1439, AB272104).

Northern Blotting.

Two μg of poly(A) RNA from various tissues of the medaka were electrophoretically fractionated and transferred to a Nytran-plus membrane (Schleicher and Schuell, Dassel, Germany). The blots were hybridized with 32P-labelled cDNA fragments (nucleotides 3359-3953 in AB272104 for EP and 572-835 in AB272106 for trypsinogen) in buffer containing 50% formamide, 5×0.15 M NaCl/8.65 mM NaH2PO4/1.25 mM EDTA (SSPE), 1% SDS, 5×Denhardt's solution, and 100 μg/ml denatured salmon sperm DNA. The membranes were washed twice in 2×SSC/0.05% SDS and then twice in 0.1×SSC/0.1% SDS at 50° C. As a control, medaka cytoplasmic actin (OLCA1) mRNA was detected with a 32P-labeled 312-bp DNA fragment of the fish cDNA (2).

Southern Blotting.

Medaka genome DNA was extracted as described previously (3), with the exception that the whole-genome DNA was purified from the medaka whole body. Twenty μg of the genomic DNA was completely digested with various restriction enzymes. The digested DNA was fractionated on a 0.7% agarose gel and alkaline-transferred to a Nytran membrane (Schleicher & Schuell). The blot was hybridized at 60° C. for 16 h in 6×SSPE, 5×Denhardt's solution, 1% SDS, 10% dextran sulfate, and 100 µg/ml denatured herring sperm DNA with a 32P-labeled 595-bp fragment of medaka EP cDNA (nucleotides 3359-3953, AB272104). The membrane was washed at 60° C. in 0.1×SSC/0.1% SDS and exposed to Kodak Biomax Film.

In Situ Hybridization.

In situ hybridization was performed using frozen intestine and ovary sections (15 µm) as described previously (4). RNA probes were prepared by in vitro transcription of reverse-transcriptase fragments of cDNAs with T3 or T7 RNA polymerase using a digoxigenin (DIG) RNA-labeling kit (Boehringer-Mannheim, Mannheim, Germany). A 595-bp cDNA fragment (nucleotides 3359-3953, AB272104) was used as a specific probe. The hybridization was conducted at 50° C. for 18 h in 50% formamide, 5'Denhardt's solution, 6' SSPE, and 0.5 mg/ml yeast transfer RNA. The sections were washed once at 50° C. in 50% formamide/2' SSC for 30 min, once at 50° C. in 2' SSC for 20 min, and twice at 50° C. in 0.2° SSC for 20 min. The hybridization probes were detected using a Dig Nucleic Acid Detection Kit (Roche Molecular Biochemicals, Mannheim, Germany).

Preparation of Recombinant Proteins.

For preparation of medaka recombinant trypsinogen, a trypsinogen cDNA fragment (nucleotides 72-755, AB272106) containing its coding sequence, but without the putative signal sequence, was amplified by PCR using the following primers: 5'-CCGGAATTCCTTGACGATGACAAG-3' (SEQ ID NO: 26) and 5'-CCCAAGCTTTCAGTTGCTAGCCATGGT-3' (SEQ ID NO: 27). The PCR product was digested with EcoR I and Hind III, gel-purified and ligated into the pET30a expression vector. The expression of recombinant medaka trypsinogen in the *Escherichia coli* expression system and its purification with an Ni2+-Sepharose column were the same as for the wild-type EP protein described above. The purified recombinant protein was renatured by dialysis against 50 mM Tris.HCl (pH 8.0) and further purified with a column of Resource Q. These procedures yielded a fusion protein of medaka trypsinogen that had a vector-derived 52-residue peptide at its N-terminus in addition to the 227-residue sequence of the fish trypsinogen. Thus, this recombinant fusion protein contained two EP-cleavage sites: one from the vector used and the other from trypsinogen itself.

For preparation of the insertional mutant of the human tissue-type plasminogen activator (tPA), a cDNA coding for human tPA (5) was first obtained by RT-PCR from a human ovary total RNA (Stratagene) using the primers 5'-CCCAAGCTTATGAAGAGAGGGCTCTGCTGT-3' (SEQ ID NO: 28) (sense-1) and 5'-CTTATCGTCATCATGATGATGATGGTGTCTGGCTCCTCTTCT-3' (SEQ ID NO: 29) (antisense-1) (BC007231). Using the cDNA as a template, two PCR products were amplified with following primer combinations: sense-1 and antisense-1; and 5'-CACCATCATCATCATGATGACGAC-GATAAGTCTTACCAAGTGATC-3' (SEQ ID NO: 30) (sense-2) and 5'-CCGCTCGAGTCACGGTCGCATGTTGTCACGAAT-3' SEQ ID NO: 31) (antisense-2). Using a mixture of these amplified DNAs as templates, the second PCR was performed with the sense-1 and antisense-2 primer. The PCR products were digested with HindIII and XhoI, then gel-purified and ligated into the pCMV tag4 mammalian expression vector (Stratagene). The resulting mutant was confirmed by DNA sequencing and transfected into CHO cells cultured in F-12 medium (Invitrogen) containing 10% fetal bovine serum (Biological Industries, Beit Haemek, Israel). Transfection was performed using Lipofectamin 2000 (GE Healthcare Biosciences, Uppsala, Sweden). The above procedure produced a fusion protein of human tPA having 11 extra amino acid residues (His-His-His-His-His-His-Asp-Asp-Asp-Asp-Lys (SEQ ID NO: 32): a His-tag sequence followed by an EP-cleavage site) at the N-terminus of mature tPA. This fusion protein secreted from transfected CHO cells was collected from the culture media using an Ni2+-Sepharose column. Treatment of the fusion protein with EP proteases generated mature tPA without the 11-residue N-terminal peptide.

Recombinant human kallikrein 8 was prepared as described previously (6).

Recombinant medaka gelatinase A was prepared as described previously (4).

Production of Anti-Medaka EP Protease Antisera.

The protein antigen was produced using the bacterial expression system with pET30a as described above. The recombinant protein eluted from an Ni2+-Sepharose column was injected into rabbits. The specific antibody was affinity-purified using membranes onto which pure antigen was blotted (4).

Western Blotting and Immunohistochemistry.

Whole tissues of medaka intestines, ovaries, and testes were separately homogenized in PBS containing 5 mM EDTA and protease inhibitor cocktail (Wako Chemicals, Osaka, Japan), and centrifuged at 18,000' g for 10 min to obtain supernatant fractions. The supernatants were analyzed by Western blot analysis (4). For fractionation of medaka intestines, tissues were homogenized in 50 mM Tris.HCl (pH 7.4), 10 mM KCl, 10 mM MgCl2, 1 mM dithiothreitol, 5 mM EDTA and protease inhibitor cocktail (Wako), and centrifuged at 1,600' g for 8 min. The pellet was collected as crude nuclei. The supernatant was further centrifuged at 100,000' g for 30 min. The resulting supernatant and pellet were used as a cytosol and membrane fraction, respectively (7). The primary antibodies were affinity-purified EP protease antibodies as described above. Intestine sections (15 µm) were cut on a cryostat and thaw-mounted onto slides coated with silan. Sections on slides that were fixed with 4% paraformaldehyde in PBS for at least 15 min were treated with 3% H2O2 in PBS. After being blocked with BlockAce (Dainippon Seiyaku, Osaka, Japan) for 1 h at room temperature, each section was incubated with purified primary antibodies for 1 h at room temperature, and was then washed with PBS. Bound antibodies were detected using DakoCytomatin EnVision+ System-labeled polymer-HRP anti-rabbit (Dako, Carpinteria, Calif.) according to the manufacturer's instructions. Immunocomplexes were detected using an AEC kit (Vector Laboratories, Burlingame, Calif.).

Gel Filtration Chromatography.

Gel filtration chromatography was performed using a HiLoad 16/60 Superdex 200 µg column (GE Healthcare Biosciences) equilibrated with 50 mM Tris.HCl (pH 8.0) and 0.2 M NaCl. Medaka intestine was homogenized in the same buffer containing 5 mM EDTA and protease inhibitor cocktail (Wako) and centrifuged at 18,000 g for 10 min to obtain the supernatant. The resulting supernatant was applied to the column at a flow rate of 24 ml/h. Fractions of 1 ml were collected and assayed for EP protease activity using GD4K-βNA (SEQ ID NO: 6) as a substrate. The active fractions were pooled and used for Western blotting. Calibration of the column was conducted using an HMW gel filtration calibration kit (GE Healthcare Biosciences).

Enzyme Stability.

One hundred nanograms of medaka, porcine, and bovine enteropeptidase were separately incubated at 37° C. in 20 mM Tris.HCl buffer (pH 7.4) containing 50 mM NaCl and 2 mM CaCl2. The enzyme activity was measured at various time points (0 to 96 h) using GD4K-βNA (SEQ ID NO: 6) as a substrate.

Inhibitor Assay.

Active medaka enteropeptidase was preincubated with various inhibitors at 37□ in 20 mM Tris.HCl buffer (pH 7.4) containing 50 mM NaCl and 2 mM CaCl2. After incubation for 10 min, the enzyme activity was measured using GD4K-βNA (SEQ ID NO: 6) as a substrate.

Example 1 cDNA Cloning and Expression of Medaka EP

RNA was isolated from the intestine and ovary of Medaka using Isogen (Nippon Gene, Tokyo, Japan). From the thus-obtained total RNA of the Medaka intestine, the first strand of cDNA was synthesized using a SuperScript First-Strand Synthesis System for RT-PCR (Invitrogen, Carlsbad, Calif.). Two degenerate oligonucleotide PCR primers were synthesized based on the cDNA sequences for conserved C-terminal catalytic protease domains in mammalian EPs (sense primer: 5'-TCIGC(C/T)GC(A/C)CACTG(C/T)GT(C/G)TA(CM(A/G)G(A/G)-3' (SEQ ID NO: 33), which corresponds to the sequence around the active site histidine, NH$_2$-Ser-Ala-Ala-His-Cys-Val-Tyr-Gly-COOH (SEQ ID NO: 34); and anti-sense primer: 5'-(G/T)A(A/G)TGG(C/T)CC(G/T)CC(A/T)GAATC(A/C)CCCTG-3' (SEQ ID NO: 35), which corresponds to the sequence around the active site serine, NH$_2$—Gln-Gly-Asp-Ser-Gly-Gly-Pro-Leu-COOH (SEQ ID NO: 36)).

The thus-obtained cDNAs were amplified under the following PCR conditions: 3 min at 94° C. for denaturation, 30 cycles of 0.5 min at 94° C., 0.5 min at 55° C. for annealing, and 0.5 min at 72° C. for extension, followed by 7 min final extension at 72° C. Fragments of about 0.5-kb in size were recovered from the PCR products by agarose gel purification and subcloned into pBluescript, (II) KS+ (Stratagene, La Jolla, Calif.). A 461-bp clone was obtained and was used as a probe for further screening of a Medaka cDNA library.

A Medaka intestine random cDNA library was constructed in λgt10 and was packaged using Gigapack III packaging extract (Stratagene). Approximately 6×10$^5$ plaques from the library were transferred to nylon membranes (Schleicher and Schuell, Dassel, Germany) and hybridized at 65° C. in a buffer containing 5×SSPE, 0.5% SDS, 5×Denhardt's solution (Wako, Osaka, Japan), and 100 μg/ml denatured salmon sperm DNA with the $^{32}$P-labeled 461-bp PCR fragment described above. Filters were washed with increasing stringency, with a final wash of 0.1×SSC/0.1% SDS at 50° C. Phage DNA was subcloned into pBluescript (II) KS+ for sequencing. An EP clone containing 2689-bp cDNA (nucleotides 611-3298) was obtained. Further screening was conducted with the same library using an EP 477-bp probe (nucleotides 630-1101), and resulted in isolation of a 1364-bp cDNA containing the 5' portion of the EP sequence.

A 3' portion of Medaka EP was obtained by the 3'-RACE method (Frohman et al., *Proc. Natl. Acad. Sci. USA,* 85:8998-9002 (1988)) using the 3'-Full RACE Core Set (Takara, Tokyo, Japan). The sense primers used were 5'-GACATTC-TACAGGAGGCTGAGGTT-3' (SEQ ID NO: 37) (RACE 1; nucleotides 2900 to 2923) and 5'-CGTCTCTTACCCGAG-TACACCTTC-3' (SEQ ID NO: 38) (RACE 2; nucleotides 2951 to 2974). The two rounds of PCR reactions were performed under the conditions of 35 cycles of 0.5 min at 94° C., 0.5 min at 55° C., and 1 min at 72° C. for the first PCR and 35 cycles of 0.5 min at 94° C., 0.5 min at 57° C., and 1 min at 72° C. for the second PCR. The amplified products were then subcloned into pBluescript II plasmid (Stratagene) and sequenced.

Medaka EP mRNA exists in two distinct forms, EP-1 and EP-2, in the intestine. A comparison of the entire amino acid sequences of EP-1 (1043 residues) and EP-2 (1036 residues) reveals a difference of only 22 amino acids, including an insertion of 7 residues in EP-2. Here, two distinct Medaka EP cDNA clones, designated as EP-1 (3997-bp, deposited in the DDBJ database, Accession No. AB272104) and EP-2 (4036-bp, AB272105), were obtained. The full-length EP-1 cDNA clone contained an ORF that codes a protein of 1043 amino acids, while the EP-2 clone codes a protein of 1036 amino acid residues (FIG. 5). The deduced amino acid sequence of the Medaka EP was homologous with those of its mammalian counterparts. As in mammalian EPs, unique domain structures were found in the N-terminal heavy chain of the fish protein, as shown in FIG. 1A. However, the extent of sequence identity between the Medaka and mammalian EPs varies considerably from one domain to another: the identity is 21% in the mucin-like domain, 45% in LDLR domain 1, 41% in C1 r/s domain 1, 49% in the MAM domain, 57% in C1 r/s domain 2, 47% in LDLR domain 2, and 23% in the MSCR domain. The C-terminal serine protease domain of Medaka EP exhibited 53% identity for mammalian EP serine proteases.

RT-PCR analyses using primer sets specific for the two Medaka Eps observed that the band intensities of amplified products were greater in EP-1 than EP-2 at every PCR cycle (FIG. 5B). RT-PCR using primers common to the two EP transcripts was also performed. Amplified products (1235 bp for EP-1 and 1246 bp for EP-2) were gel-purified and subcloned into pBluescript (II) KS$^+$, and the recombinant plasmids were transformed into *E. coli,* strain JM109. Forty-four clones were randomly picked for the nucleotide sequence analyses; 26 clones were for EP-1 and 18 clones for EP-2. The results indicated that EP-1 is a dominant EP species expressed in the Medaka intestine. The result of Southern blot analysis supports the presence of at least two distinct copies of the EP gene in the Medaka (FIG. 5C).

Figures 1, 1B, 2:
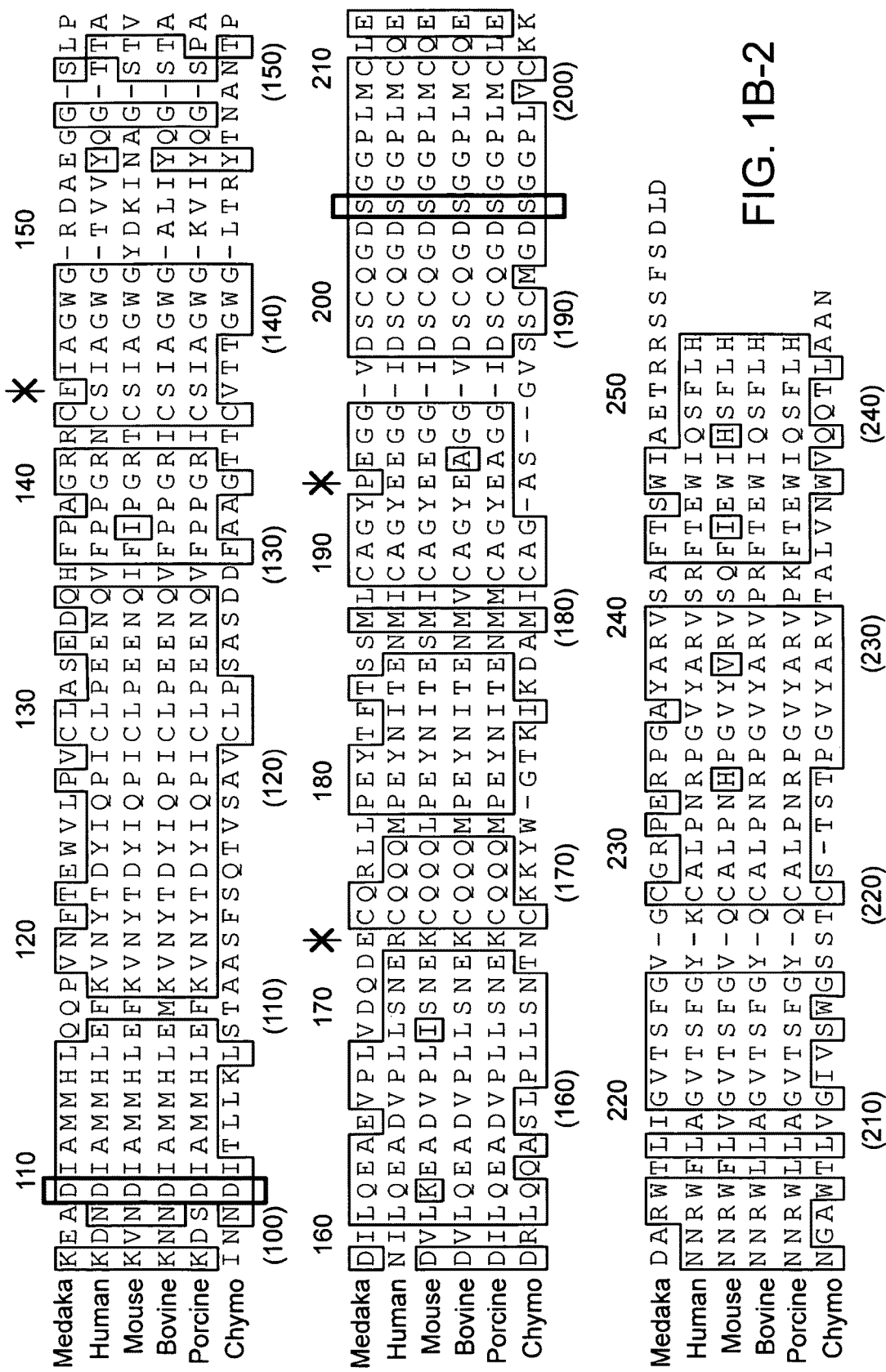
FIG. 1(B) shows amino acid sequence alignment of the EP serine protease domain. Amino acid residues are numbered based on the sequence of Medaka EP (top numbers). For comparison, the data for bovine chymotrypsinogen (Chymo) are included among the chymotrypsinogen residue numbers (in parenthesis at the bottom of each block). The arrow indicates a putative activation site between the heavy and light chains. The active site residues (H, D and S) are boxed. The positions of mutations are indicated by asterisks. Figure discloses SEQ ID NOS 65-70, respectively, in order of appearance.
FIG. 2 (A-F) shows the specificity of Medaka EP-1 protease on peptide and protein substrates. (A) Active recombinant EP proteases were assayed using a GD4K-βNA (SEQ ID NO: 6) substrate as a substrate. Bovine (Nvg), bovine EP protease available from Novagen; Bovine (Neb), bovine EP protease available from NEB. (B) Active recombinant EP proteases were assayed using various synthetic peptide substrates. (C) Active EP proteases were analyzed by gelatin zymography. (D) Fibronectin (4 µg) was incubated with active EPs (100 ng) at 37° C. for 12 h. (E) Laminin ((10 µg) was incubated with active recombinant EPs (100 ng) at 37° C. for 12 h. (F) Two µg of the control protein containing the D4K site (SEQ ID NO: 1) was incubated with active recombinant EPs (100 ng) at 37° C. for 1 h.
Figure 1C:
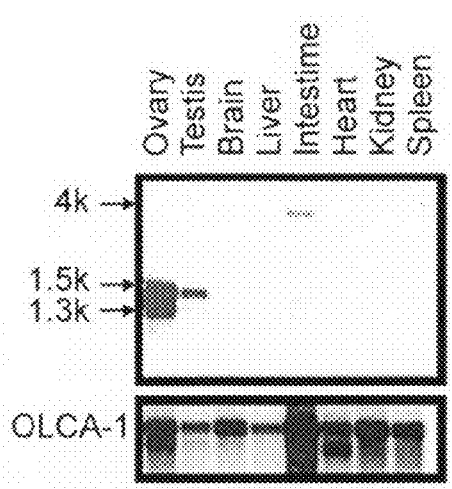
FIG. 1(C) shows Northern blotting analysis of the expression of Medaka EP mRNA in various tissues. The sizes of the detected mRNAs are shown at the left. The lower panel shows the results for Medaka cytoplasmic actin mRNA as a control.

Northern blot analysis of EP using various fish tissues revealed that the intestine expresses an approximately 4 kb transcript, and this size is consistent with that of the full-length cDNA, as shown in FIG. 1C. Very strong signals at 1.3 kb and 1.5 kb were detected in the ovary and testis. Further analyses indicated that they were transcripts with 1090 bp (corresponding to 2908-3997 in AB272104) and 1241 bp (corresponding to 2757-3997 in AB272104). Both transcripts were found not to code for any functional protein. In situ hybridization analysis indicated that EP mRNA was localized in the cytoplasm of small growing follicles in the ovary of mature female Medaka, as shown in FIG. 6. Neither Western blotting nor immunohistochemical analysis using specific antibodies for the Medaka EP protease detected corresponding proteins. Therefore, no further study was conducted with ovary EP transcripts.

Because no translated product of the transcripts was detected in the ovary, the biological meaning of their occurrence in this organ is not known. In this context, it is of interest to note the recent identification of non-coding RNAs in eukaryotic cells. Such studies indicate that non-coding RNAs regulate gene expression by novel mechanisms such as RNA interference, gene co-suppression, gene silencing, imprinting and DNA methylation (21). A possibility may be that EP transcripts expressed in the fish ovary play a role as non-coding RNAs in the oocytes of growing follicles.

Figure 1D:
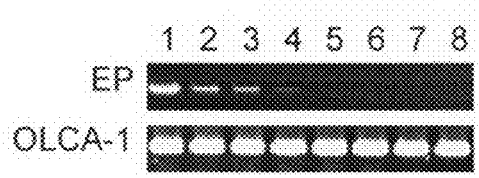
FIG. 1(D) shows RT-PCR analysis of the expression of EP mRNA in the gastrointestinal tract. The Medaka gastrointestinal tract was divided into 8 pieces, from the stomach (lane 1) to the anus (lane 8), and the PCR products in each piece was electrophoresed.
Figure 1E:
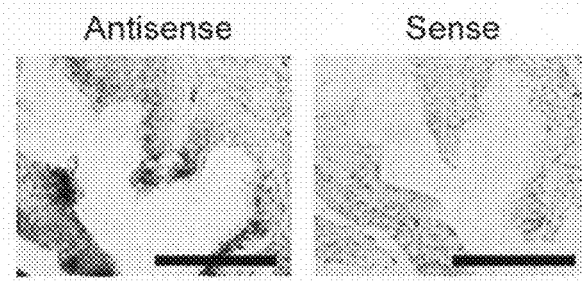
FIG. 1(E) shows in situ hybridization of EP mRNA in the Medaka intestine. Neighboring sections of Medaka intestine were hybridized with EP antisense (left panel) or sense RNA probe (right panel). Scale bars: 100 µm.
Figure 1F:
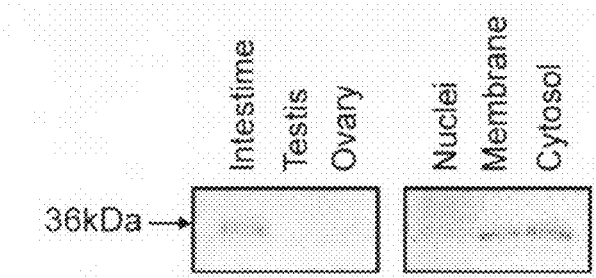
FIG. 1(F) shows Western blotting analysis of the expression of the Medaka EP protein. Extracts of the intestine, testis, and ovary (left panel), and of nuclei, membrane and cytosol fractions of the Medaka intestine (right panel) were analyzed. The size of the EP protein detected is shown at the right.
Figure 1G:
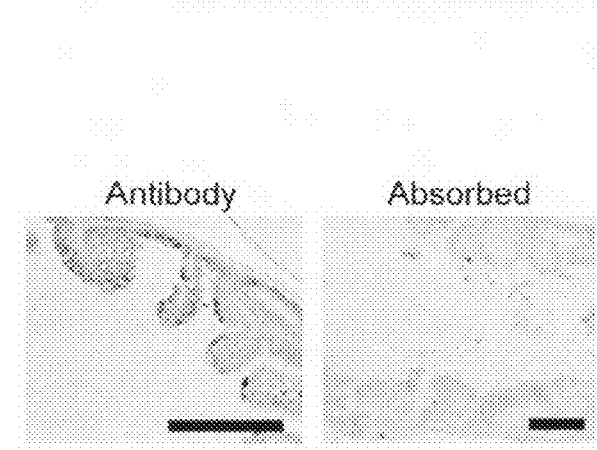
FIG. 1(G) shows immunohistochemical analysis of EP in the Medaka intestine using the Medaka anti-EP antibody (left panel). The control section was stained with the primary antibody previously treated with the antigen (right panel). Scale bars: 200 µm.

In RT-PCR using primers common to the two species of Medaka EP, transcripts were detected in the intestinal segments proximal to the stomach, as shown in FIG. 1D. In situ hybridization analysis localized EP expression to the intestinal epithelium (FIG. 1E). Western blot analysis under reducing conditions of the extract of Medaka intestine, but not ovary and testis extract, using specific anti-EP antibodies against the catalytic domain detected a 36-kDa immunoreactive band (FIG. 1F, Left). A polypeptide band of the same molecular mass was detected in both soluble and membrane fractions of the intestine (FIG. 1F, Right). Western blotting of the intestine extract under nonreducing conditions gave no clear band (data not shown). By immunohistochemical analysis using the antibody, the epithelial localization of EP in the intestine was demonstrated (FIG. 1G).

Figure 7A:
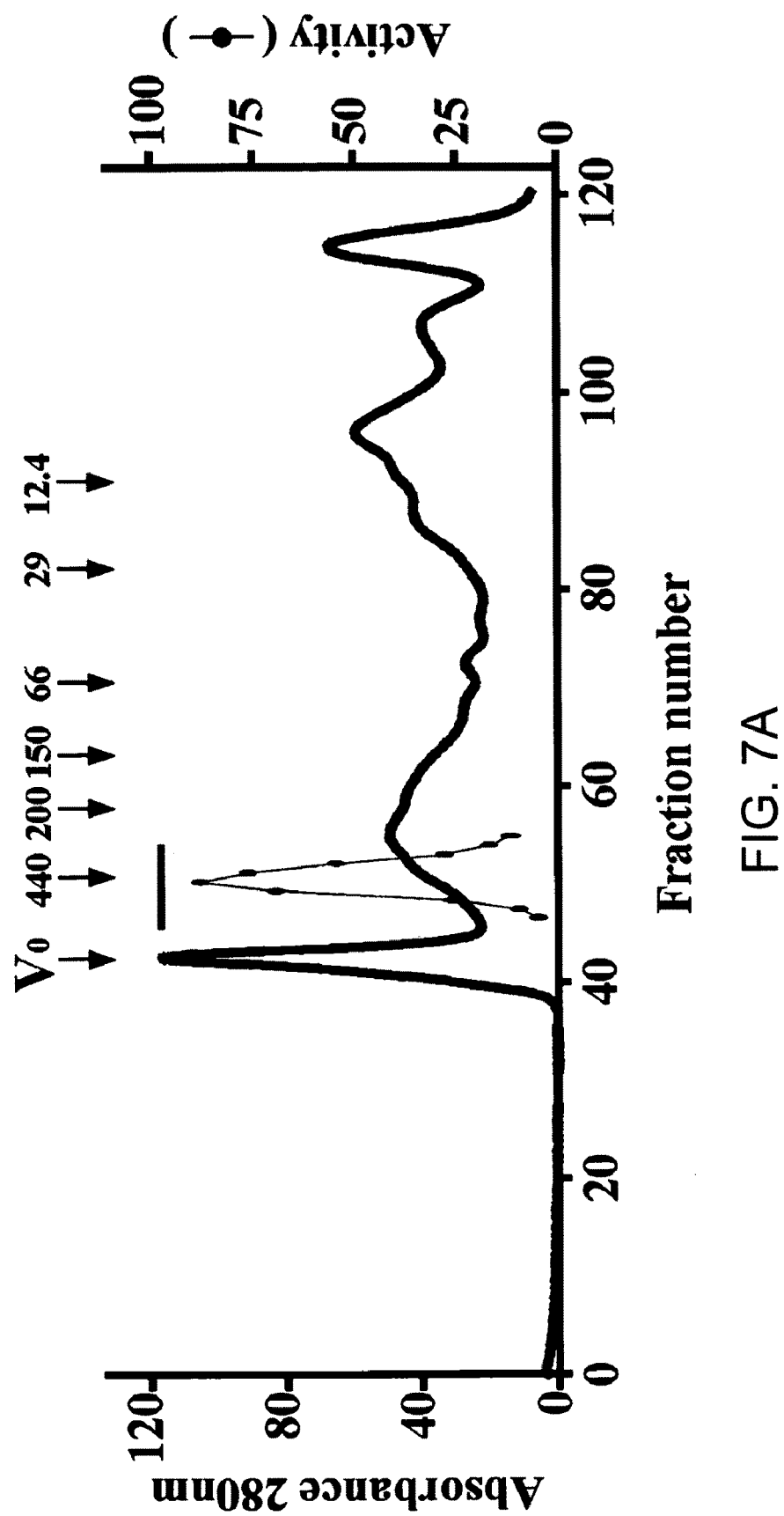
FIG. 7 (A and B) shows gel filtration analysis of Medaka intestine extracts. (A) The intestine extract was fractionated using a HiLoad 16/60 Superdex 200 µg column. Fractions having GD4K-βNA-hydrolyzing (SEQ ID NO: 6) activity (indicated by a bar) were pooled. (B) The pooled active fraction was subjected to SDS-PAGE/Western blotting analysis under a reducing condition (left panel) or nonreducing condition (right panel) using anti-Medaka EP protease antibody.
Figure 7B:
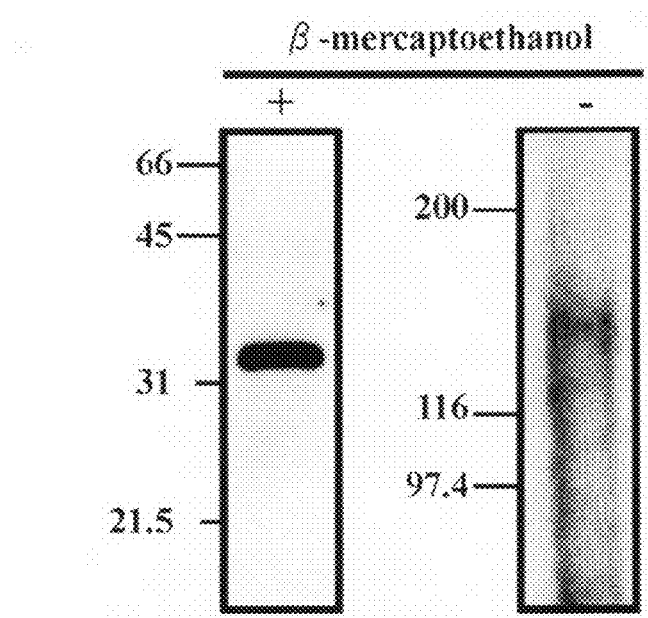

The extract of Medaka intestines exhibited enzyme activity for the synthetic EP substrate $GD_4K$-βNA (SEQ ID NO: 6). Using this activity as a marker, the apparent molecular mass of intact EP was estimated to be 440 kDa by gel filtration (FIG. 7A). The above fraction having $GD_4K$-βNA-hydrolyzing activity (SEQ ID NO: 6) showed a 36-kDa polypeptide in Western blotting under reducing conditions (FIG. 7B, Left). Again, the same fraction did not show any clear band with the current antibody when analyzed under non-reducing conditions (FIG. 7B, Right).

The data presented herein suggests that EP-1 and EP-2 mRNA are expressed at a ratio of approximately 6:4 in the intestine. It remains to be determined whether they are indeed translated at this ratio. Moreover, it is not known at present whether they have a discrete role in vivo.

Taken together, the above results indicate that the fish intestine contains active, membrane-bound EP. Part of the molecule exists in the intestine in a soluble form that is probably detached from the epithelial cell membrane.

Example 2

Preparation and Properties of Recombinant EP Serine Protease Domain

A DNA fragment including the coding sequence for the Medaka EP-1 or EP-2 catalytic domain was amplified by PCR using a pBluescript II plasmid containing cDNA of the catalytic domain as the template. The upper and lower primers were 5'-CGCGGATCCCAAGCTGGTGTGGTGGGTGG-3' (SEQ ID NO: 39) and 5'-CCCAAGCTTTCAGTCTA-GATCTGAGAA-3' (SEQ ID NO: 40), respectively, which had BamHI and HindIII sites at the respective 5' termini. The product was ligated into the cloning site of a pET30a expression vector (Novagen, Madison, Wis.). Expression of the recombinant Medaka EP catalytic domain in the *Escherichia coli* expression system was carried out as described previously (Ogiwara et al., *Proc. Natl. Acad. Sci. USA*, 102:8442-8447 (2005)). The Medaka EP catalytic domain was produced as a fusion protein with an extra amino acid sequence of 50 residues at its N-terminus; the vector-derived N-terminal stretch contained a His-tag and an S-protein sequence. Harvested cells were lysed and the insoluble materials were dissolved in a solubilization buffer containing 6 M urea, 50 mM Tris.HCl (pH 7.6), and 0.5 M NaCl. Solubilized proteins were subjected to affinity chromatography on $Ni^{2+}$-Sepharose (GE Healthcare Biosciences, Piscataway, N.J.), and eluted with the same buffer containing 50 mM histidine. Eluted recombinant proteins were renatured by dialysis against 50 mM Tris.HCl (pH 8.0). The fusion protein was then incubated in 50 mM Tris.HCl (pH 8.0) containing 0.5 M NaCl with trypsin immobilized on Sepharose 4B at room temperature for 1 h. The immobilized trypsin was then removed by filtration. The resulting sample, which contained not only active EP protease but also inactive enzyme protein, was fractionated on a column of Resource Q in AKTA Purifier (GE Healthcare Biosciences, Uppsala, Sweden) to remove inactive enzyme. A trace amount of trypsin often contained in the sample thus prepared was removed by passing through an aprotinin-Sepharose 4B column (Sigma).

Active recombinant enzyme of the porcine EP serine protease domain (Ile800 to His1034) (Matsushima et al., *J. Boil. Chem.*, 269:19976-19982 (1994)) was prepared basically according to the method described above. Bovine EP serine protease was obtained from Novagen and New England Biolabs (NEB) (Schwalbach, Germany).

Figure 8A:
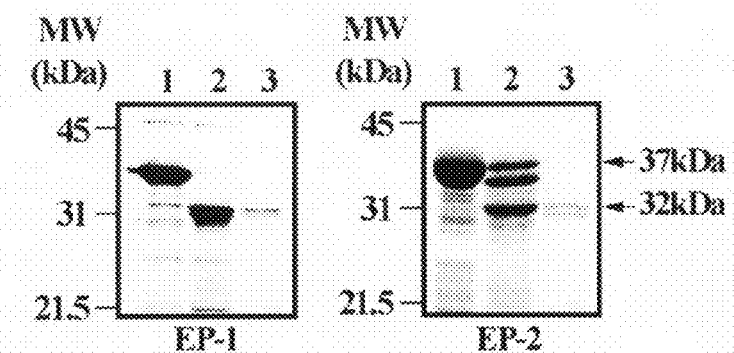
FIG. 8 (A-C) shows some enzymatic properties of recombinant Medaka EP-1 and EP-2 protease. (A) The purity of purified recombinant Medaka EP-1 and EP-2 protease was assessed by SDS-PAGE. Lane 1, Medaka EP fusion protein; lane 2, Medaka EP protease treated with immobilized trypsin; lane 3, Medaka EP protease purified using a resource Q column. (B) The enzyme activities of EP proteases were determined at various pHs using GD4K-βNA (SEQ ID NO: 6) as a substrate. (C) Recombinant Medaka trypsinogen was incubated at 37° C. with EPs for 15, 30 and 45 min. After incubation, samples were analyzed by SDS-PAGE and visualized by CBB staining (upper panel). The relative amount of the active form of Medaka trypsin at each time point were calculated based on the results shown in the upper panel (lower panel). The results are presented as the means (±SD) of three separate experiments.
Figure 8B:
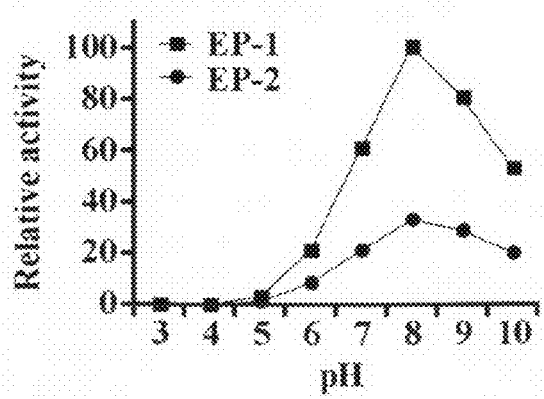

The active 32-kDa carboxyl-terminal serine protease domains of both EP-1 and EP-2 were prepared to characterize their enzymatic properties, as shown in FIG. 8A. Both enzymes showed maximal activities for $GD_4K$-βNA (SEQ ID NO: 6) at pH 8, but EP-1 was approximately three times more active than EP-2, as shown in FIG. 8B.

Figure 8C:
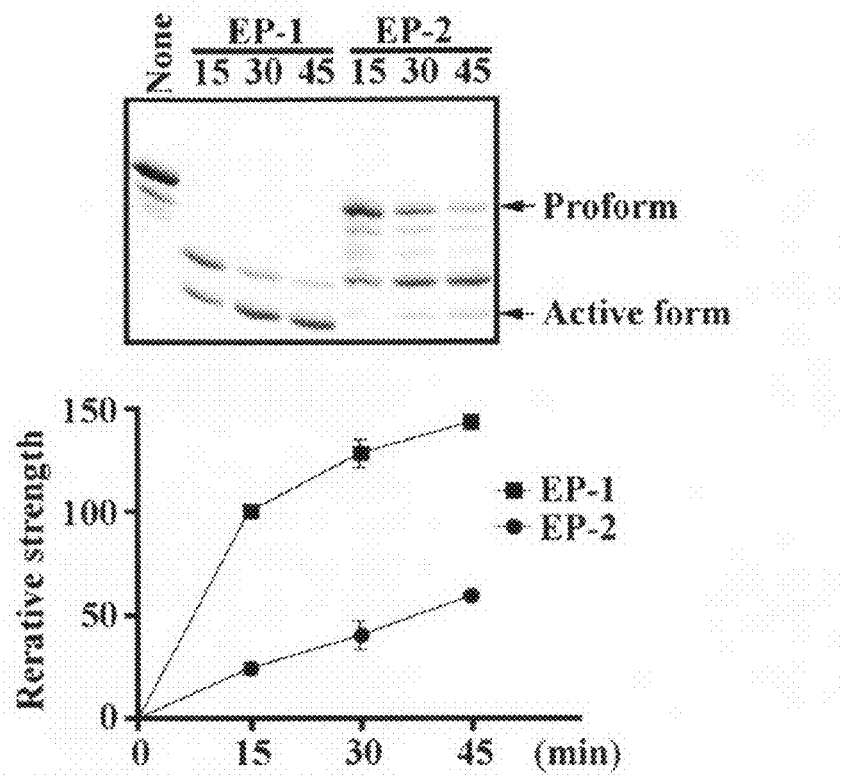
Figure 9B:
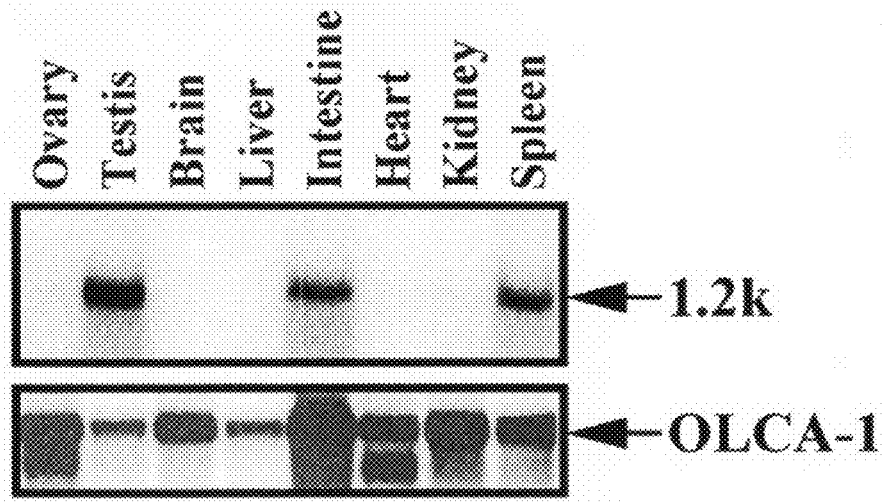
FIG. 9 (A and B) shows the cloning and expression of Medaka trypsinogen. (A) Amino acid sequence alignment of trypsinogen of the Medaka (SEQ ID NO: 73), human (BAA08257) (SEQ ID NO: 74), mouse (AAH61135) (SEQ ID NO: 75), and salmon (CAA49676) (SEQ ID NO: 76) is shown. A well conserved $D_4K$-cleavage site (SEQ ID NO: 1) for EP is indicated by a broken line. Active site residues (H, D, and S) are boxed. (B) The tissue distribution of Medaka trypsinogen mRNA was analyzed by Northern blotting (upper panel). The sizes of the detected mRNAs are shown at the right. The lower panel shows the detection of Medaka cytoplasmic actin-1 (OLCA-1) mRNA as a control.

To examine the effects of EP-1 and EP-2 on the physiological substrate trypsinogen, a 866-bp Medaka trypsinogen cDNA (AB272106), which codes for a protein of 242 amino acids (FIG. 9, supporting information), was obtained from the intestine. Using the sequence, a recombinant fusion protein of Medaka trypsinogen was prepared. The trypsinogen was converted to active trypsin by EP-1 faster than by EP-2 (FIG. 8C). The behavior of the two proteases for various protease inhibitors was undistinguishable, as illustrated in Table 1, below.

TABLE 1

| Inhibitor | Concentration | Inhibition (%) | |
|---|---|---|---|
| | | EP-1 | EP-2 |
| EDTA | 5.0 mM | 5 | 10 |
| DFP | 0.2 mM | 99 | 99 |
| Benzamidine | 1.0 mM | 79 | 78 |
| Antipain | 0.1 mM | 18 | 20 |
| Leupeptin | 0.1 mM | 43 | 47 |
| Chymostatin | 0.1 mM | 0 | 0 |
| Aprotinin | 0.01 mg/ml | 0 | 5 |
| SBTI | 0.1 mg/ml | 99 | 99 |
| E-64 | 0.2 mM | 0 | 0 |
| Pepstatin | 0.1 mM | 0 | 3 |

Table 1 shows the effects of inhibitors on medaka EP-1 and EP-2 protease activity. The enzyme activities of medaka EP-1 and EP-2 protease were determined in the presence of various inhibitors using GD4K-βNA (SEQ ID NO: 6) as a substrate. Values are expressed as the percent inhibitions of the respective control activities. Results are the averages of triplicate determinations. From these results, together with the finding that EP-1 is the dominantly expressed form in the intestine, EP-1 was chosen to be used in the following experiments.

Figure 2A:
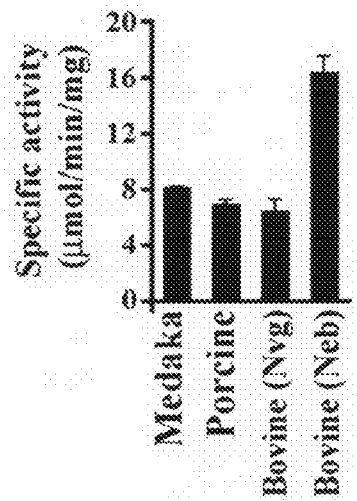
Figure 2B:
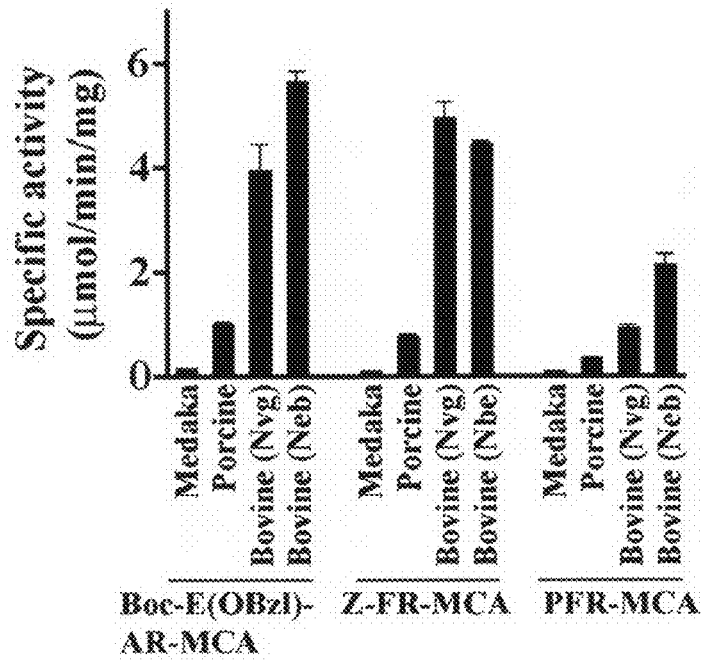

The serine protease domain of Medaka EP-1 cleaved $GD_4K$-βNA (SEQ ID NO: 6) at a rate comparable to those of the porcine and bovine enzymes (FIG. 2A). Surprisingly, the amidolytic activities of Medaka EP-1 protease for the synthetic MCA-containing peptide substrates Boc-Glu(OBzl)-Ala-Arg-MCA, Z-Phe-Arg-MCA, and Pro-Phe-Arg-MCA were much lower than those of the EP proteases of mammalian origin (FIG. 2B). The kinetic parameters of the proteases for these substrates were determined, and shown in Table 2, below. Generally, the $k_{cat}/K_m$ values of the Medaka enzyme were 1-2 orders of magnitude smaller than those of the mammalian proteases for all MCA-containing synthetic substrates.

TABLE 2

| | GD4K-βna (SEQ ID NO: 6) | | | Boc-E(OlBz)-AR-MCA | | |
|---|---|---|---|---|---|---|
| | Km (mM) | kcat (min$^{-1}$) | kcat/Km (mM$^{-1}$·min$^{-1}$) | Km (mM) | kcat (min$^{-1}$) | kcat/Km (mM$^{-1}$·min$^{-1}$) |
| EP-1(WT) | 0.7 | 940 | 1300 | 0.2 | 6.7 | 34 |
| K63R | 0.2 | 210 | 1100 | 1.2 | 12 | 10 |
| T105E | 0.4 | 260 | 650 | 1.3 | 11 | 9 |
| E173A | 0.3 | 320 | 1100 | 1.0 | 10 | 10 |
| P193E | 0.4 | 290 | 730 | 0.2 | 2.3 | 12 |
| Porcine | 0.4 | 530 | 1300 | 0.3 | 110 | 370 |
| Bovine (Nvg) | 0.8 | 770 | 960 | 0.5 | 740 | 1500 |
| Bovine (Neb) | 0.5 | 1500 | 3000 | 0.4 | 570 | 1400 |

| | Z-FR-MCA | | | PFR-MCA | | |
|---|---|---|---|---|---|---|
| | Km (mM) | kcat (min$^{-1}$) | kcat/Km (mM$^{-1}$·min$^{-1}$) | Km (mM) | kcat (min$^{-1}$) | kcat/Km (mM$^{-1}$·min$^{-1}$) |
| EP-1(WT) | 0.1 | 2.9 | 29 | 10 | 140 | 14 |
| K63R | 0.1 | 1.4 | 14 | 1.1 | 11 | 10 |
| T105E | 0.1 | 2.0 | 20 | 1.3 | 16 | 12 |
| E173A | 0.4 | 2.3 | 6 | 1.0 | 9.2 | 9 |
| P193E | 0.2 | 1.7 | 9 | 1.0 | 27 | 27 |
| Porcine | 0.2 | 55 | 280 | 3.9 | 300 | 77 |
| Bovine (Nvg) | 0.5 | 720 | 1400 | 4.0 | 790 | 200 |
| Bovine (Neb) | 0.4 | 600 | 1500 | 2.9 | 1300 | 450 |

Figure 2C:
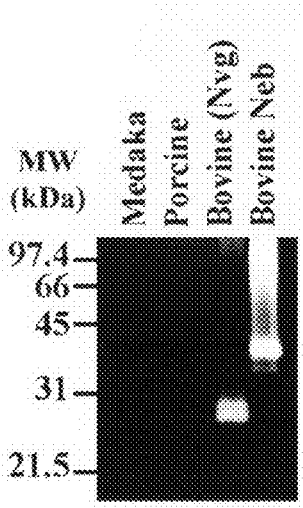
Figure 2D:
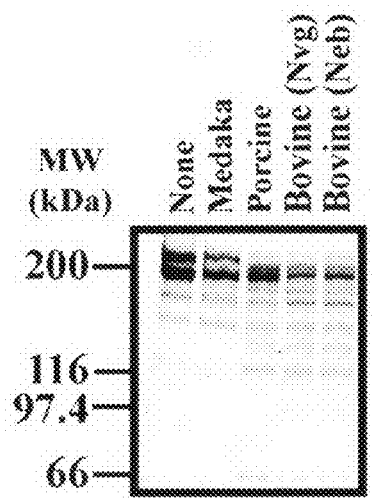
Figure 2E:
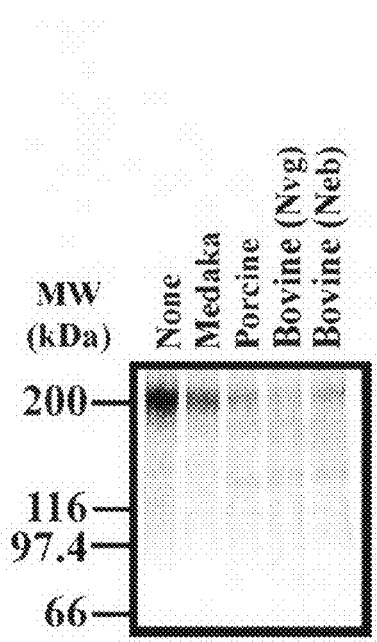
Figure 2F:
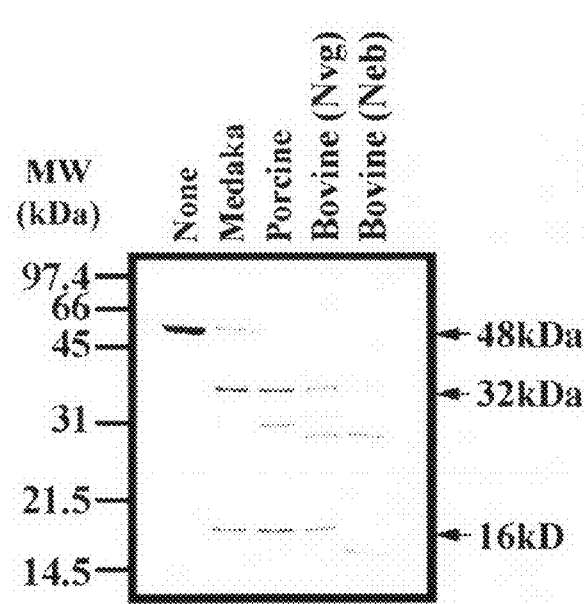

Next, the proteolytic activity of the Medaka protease was examined using gelatin (FIG. 2C), fibronectin (FIG. 2D), and laminin (FIG. 2E). For comparison, the mammalian proteases were also tested under the same conditions. Little or no hydrolysis was observed with the fish enzyme for the proteins, while these substrates were detectably hydrolyzed by the mammalian proteases. Finally, the fusion protein containing an EP-cleavage site (available from Novagen) was tested with various EP proteases. Clearly, the Medaka protease specifically cleaved the fusion protein to generate two polypeptides having expected molecular masses of 16- and 32-kDa (FIG. 2F). In contrast, the mammalian enzymes not only produced the two expected polypeptides but also further degraded the products, presumably due to their extensive nonspecific proteolytic activities. These results demonstrate that the Medaka EP-1 protease intrinsically has much more strict cleavage specificity than its mammalian counterparts.

Figure 10:
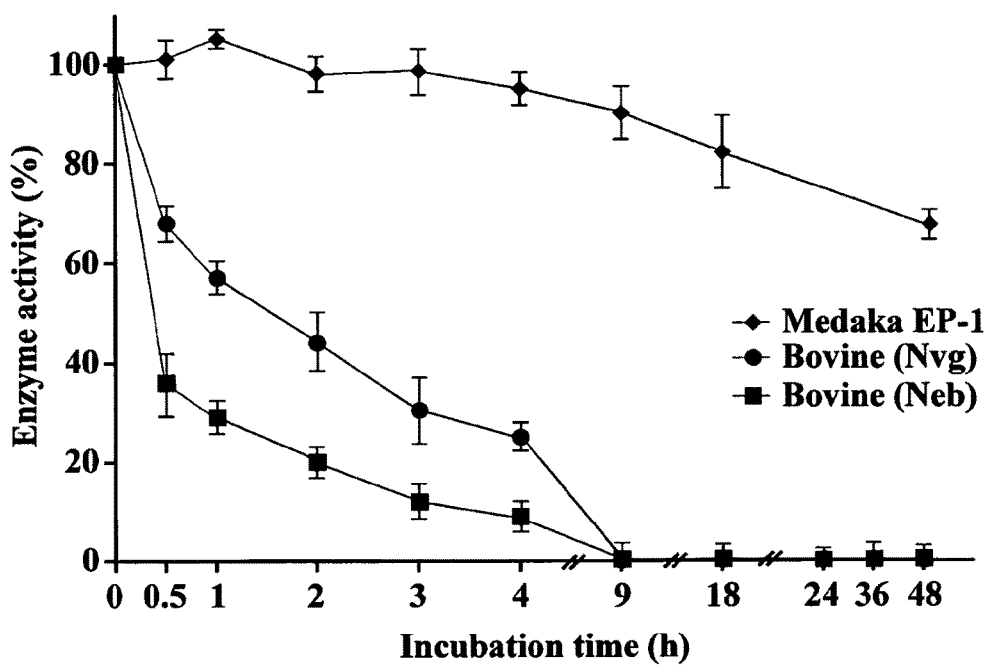
FIG. 10 shows the stability of EP protease. Medaka and mammalian EP proteases were incubated at 37° C. in 20 mM Tris.HCl (pH 7.4), 0.2 M NaCl and 2 mM $CaCl_2$. Aliquots of the reaction mixtures were taken at the indicated times for an activity assay using GD4K-βNA (SEQ ID NO: 6) as a substrate. The enzyme activities relative to that at 0-time are shown.

Active recombinant Medaka EP-1 was stable at −20° C. and 4° C.; the initial enzyme activity was retained at both temperatures for at least six months with no detectable change in the electrophoretic pattern. When Medaka EP-1 alone was kept at 37° C. at neutral pH, about 30% loss of enzyme activity was observed after 4 days of incubation (FIG. 10). In a parallel experiment using bovine EP protease, a sharp decline in enzyme activity was seen after even just a few hours of incubation at 37° C.

Example 3

Site-Directed Mutagenesis

Site-directed mutagenesis of Medaka EP-1 was carried out to produce various mutant proteases. For each mutant, two PCR products were first amplified with Medaka EP-1 cDNA as a template using the following primer combinations: one primer combination was the "upper" primer described above and the respective antisense primer, and another combination was the "lower" primer described above and the sense primer. These primers are shown in Table 3, below. Using a mixture of these amplified DNAs as templates, the second PCR was performed with the "upper" and "lower" primer. The PCR products were digested with BamHI and HindIII, gel-purified, and ligated into the pET30a expression vector. All mutants were confirmed by DNA sequencing. The subsequent procedures for preparation of mutant proteases were the same as for the wild-type protein described above. The active recombinant protein concentrations were determined using the active site titrant p-nitrophenyl-p'-guanidinobenzoate HCl (Sigma) using the method described previously (Chase et al., *Biochem. Biophys. Res. Commun.*, 29:508-514 (1976)).

TABLE 3

| Mutant | SEQ ID NO | Primer sequences |
|---|---|---|
| K63R | 41 | Sense<br>5'-GTCTATGGGAGGAACACACAC-3' |
| | 42 | Antisense<br>5'-GTGTGTGTTCCTCCCATAGAC-3' |
| K63A | 43 | Sense<br>5'-GTCTATGGGGCGAACACACAC-3' |
| | 44 | Antisense<br>5'-GTGTGTGTTCGCCCCATAGAC-3' |
| K63E | 45 | Sense<br>5'-GTCTATGGGGAGAACACACAC-3' |
| | 46 | Antisense<br>5'-GTGTGTGTTCTCCCCATAGAC-3' |
| T105R | 47 | Sense<br>5'-AACAGAAGAAGGAAAGAGGCA-3' |
| | 48 | Antisense<br>5'-TGCCTCTTTCCTTCTTCTGTT-3' |
| T105A | 49 | Sense<br>5'-AACAGAAGAGCCAAAGAGGCA-3' |
| | 50 | Antisense<br>5'-TGCCTCTTTGGCTCTTCTGTT-3' |
| T105E | 51 | Sense<br>5'-AACAGAAGAGAAAAGAGGCA-3' |
| | 52 | Antisense<br>5'-TGCCTCTTTTTCTCTTCTGTT-3' |
| F144S | 53 | Sense<br>5'GGAAGAAGGTGTTCCATTGCAGGGTGG-3' |
| | 54 | Antisense<br>5'-CCACCCTGCAATGGAACACCTTCTTCC-3' |
| F144A | 55 | Sense<br>5'-GGAAGAAGGTGTGCCATTGCAGGGTGG-3' |
| | 56 | Antisense<br>5'-CCACCCTGCAATGGCACACCTTCTTCC-3' |
| E173K | 57 | Sense<br>5'-GTGGACCAGGATAAGTGCCAGCGTCTC-3' |
| | 58 | Antisense<br>5'-GAGACGCTGGCACTTATCCTGGTCCAC-3' |
| E173A | 59 | Sense<br>5'-GAGACGCTGGCACTTATCCTGGTCCAC-3' |

TABLE 3-continued

| Mutant | SEQ ID NO | Primer sequences |
|---|---|---|
| | 60 | Antisense<br>5'-GAGACGCTGGCACGCATCCTGGTCCAC-3' |
| P193E | 61 | Sense<br>5'-TGTGCTGGATATGAAGAAGGCGGAGTT-3' |
| | 62 | Antisense<br>5'-AACTCCGCCTTCTTCATATCCAGCACA-3' |
| P193A | 63 | Sense<br>5'-TGTGCTGGATATGCTGAAGGCGGAGTT-3' |
| | 64 | Antisense<br>5'-AACTCCGCCTTCAGCATATCCAGCACA-3' |

Amino acid residues that differed from those of mammalian EP proteases in the corresponding positions were the primary focus. Five such residues were mutated, and shown in the sequences shown in FIG. 1B and in FIG. 3A. A total of 12 mutants could convert the recombinant Medaka trypsinogen to its active enzyme (data not shown).

Example 4

Enzyme Assays

EP activity was routinely determined using the specific substrate Gly-Asp-Asp-Asp-Asp-Lys-β-naphthylamide (GD$_4$K-βNA) (SEQ ID NO: 6) (Sigma) according to the method of Mikhailova and Rumsh (Mikhailova et al., *FEBS Lett.*, 442:226-230 (1999)). Enzyme activity for various 4-methylcoumaryl-7-amide (MCA)-containing peptide substrates was determined by the method of Barrett (Barrett et al., J., *Biochem. J.*, 187:909-912 (1980)). For kinetic studies, initial velocities, extrapolated from the plot of product versus time, were transformed into double-reciprocal plots (Lineweaver et al., *J. Am. Chem. Soc.*, 56:658-663 (1934)). The maximum velocities ($V_{max}$) and $K_m$ and $k_{cat}$ values were obtained from the intercepts of these plots. For all experiments, the results of at least three separate determinations are shown.

Figure 3A:
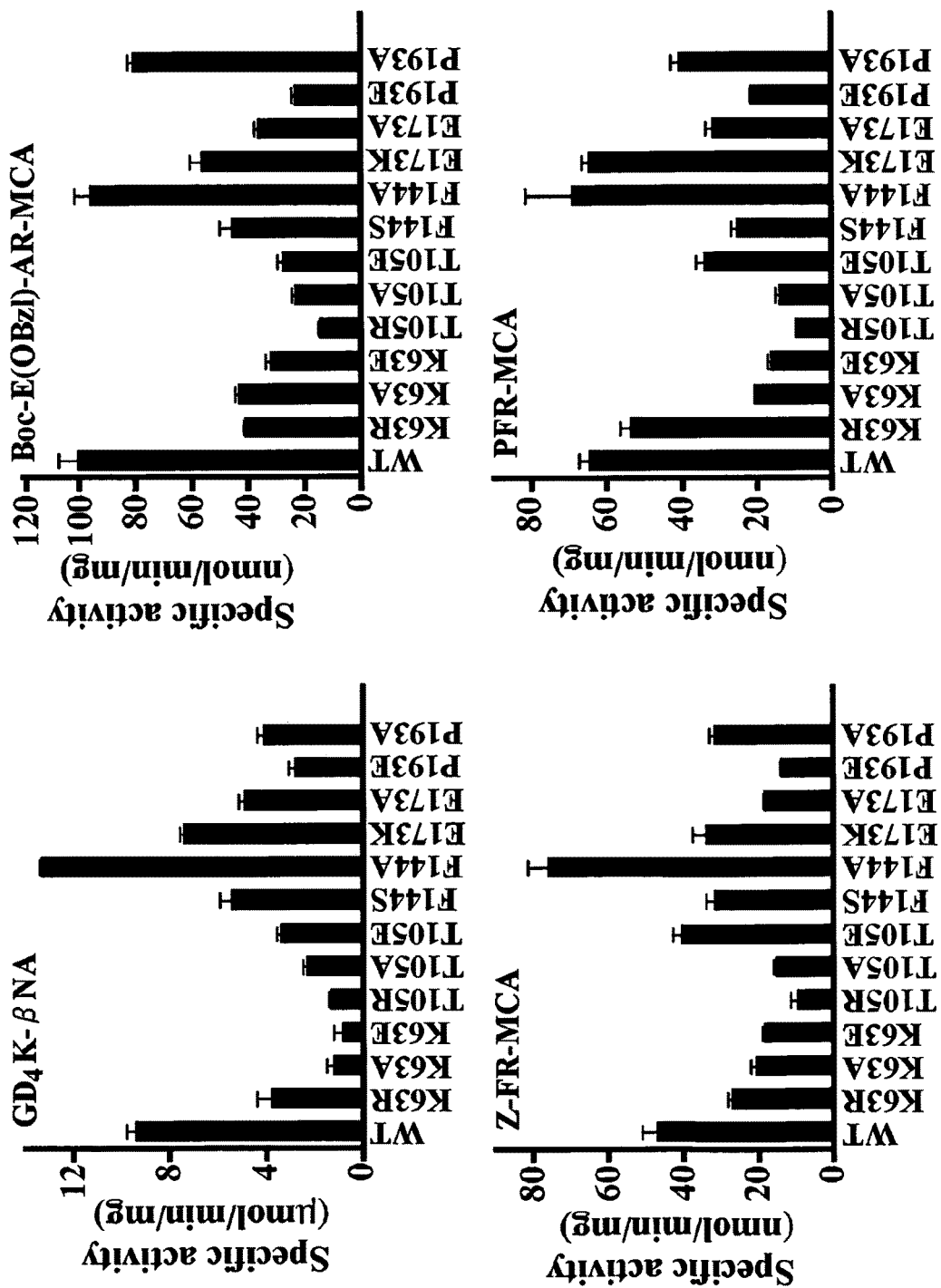
FIG. 3(A-C) shows the specificity of mutant Medaka EP proteases on peptide and protein substrates. (A) The specific activities of wild-type (EP-1) and mutant EP protease were determined using synthetic peptide substrates. (B) High-molecular-weight (HMW) kininogen (5 µg) was incubated with active EP proteases (100 ng) at 37° C. for 2 h and analyzed by SDS-PAGE. (C) Fibrinogen (10 µg) was incubated with active EP proteases (100 ng) at 37° C. for 12 h and analyzed by SDS-PAGE.
Figure 11:
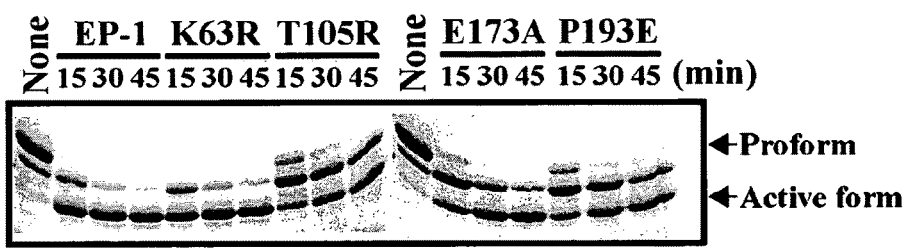
FIG. 11 shows the activation of Medaka trypsinogen by Medaka wild-type (EP-1) and mutant EP proteases. Medaka recombinant trypsinogen was separately incubated with EP proteases at 37° C. for 15, 30 and 45 min, and analyzed by SDS-PAGE followed by CBB staining (upper panel). The relative amount of the active form of Medaka trypsin at each time point was calculated based on the results shown in the upper panel (lower panel). The results are presented as the means (±SD) of three separate experiments.
Figure 11:
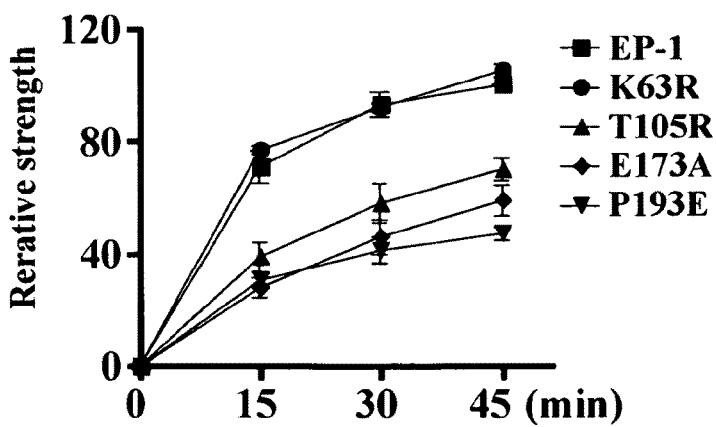
Figure 12:
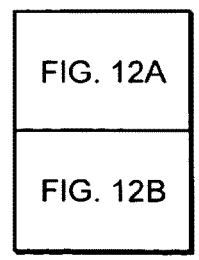
FIG. 12 shows the sequence listings.
SEQ ID NO:1—$D_4K$ Sequence
SEQ ID NO:2—Amino Acid Sequence of EP-1
SEQ ID NO:3—Nucleic Acid Sequence of EP-1
SEQ ID NO:4—Amino Acid Sequence of EP-173
SEQ ID NO:5—Nucleic Acid Sequence of EP-173

Substitutions of residues to those conserved in the mammalian EP protease (namely, K63R, T105E, F144S, E173K, and P193E) consistently resulted in reduced enzyme activity for synthetic peptide substrates, as shown in FIG. 3A. The same held true for all the other mutants except for F144A, which hydrolyzed the GD$_4$K-βNA (SEQ ID NO: 6) as well as the three MCA-containing substrates at an elevated rate when compared with the wild-type enzyme. Among the 12 mutants, K63R, T105E, E173A, and P193E were chosen for further characterization. For the recombinant Medaka trypsinogen, K63R converted to trypsin as fast as the wild type enzyme, while the other mutants activated trypsinogen at a reduced rate, as shown in FIG. 11. The mutant proteases were characterized by kinetic studies. Interestingly, E173A retained a $k_{cat}/K_m$ value comparable to the wild-type enzyme for GD$_4$K-βNA (SEQ ID NO: 6). However, the $k_{cat}/K_m$ values for the MCA-containing substrates were lowered (see Table 2, above).

Figure 3C:
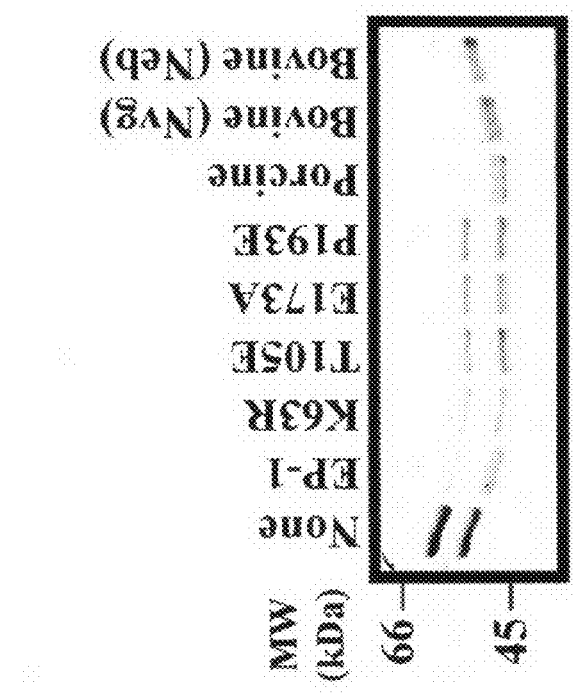
Figure 3B:
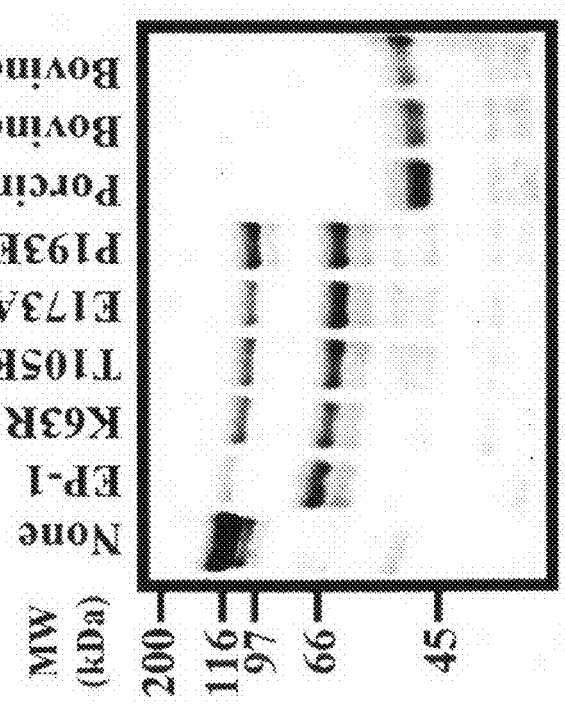

The mutant proteases had lower nonspecific proteolytic activity for human HMW kininogen (FIG. 3B) and human fibrinogen (FIG. 3C), both of which were degraded noticeably by mammalian EP proteases. Neither human fibronectin nor laminin was hydrolyzed by the mutants (data not shown).

These results indicate that the substitution of glutamic acid by alanine at 173 caused a significant reduction in unwanted, nonspecific enzyme activities for both the synthetic and protein substrates without seriously deteriorating the mutant's cleavage specificity for the GD$_4$K sequence (SEQ ID NO: 6).

Example 5

Hydrolysis of Proteins by the EP Catalytic Serine Protease Domain

The effect of Medaka EP serine protease on various fusion proteins containing a D$_4$K-cleavage site (SEQ ID NO: 1) was examined. Human plasma fibronectin (Chemicon, Temecula, Calif.), human fibrinogen (Merk Biosciences, Tokyo, Japan), human high-molecular-weight (HMW) kininogen (Calbiochem, La Jolla, Calif.), mouse laminin (Biomedical Technologies Inc., Stoughton, Mass.), D4K-cleavage site-containing (SEQ ID NO: 1) control protein (Novagen), Medaka gelatinase A (Ogiwara et al., *Proc. Natl. Acad. Sci. USA*, 102:8442-8447 (2005)) and trypsinogen (this study), human kallikrein 8 (hK8) (Rajapakse et al., *FEBS Lett.*, 579:6879-6884 (2005)) and human tissue-type plasminogen activator (tPA) were incubated at 37° C. in 20 mM Tris.HCl buffer (pH 7.4) containing 50 mM NaCl and 2 mM CaCl$_2$ with various EP serine proteases at ratios (w/w) ranging from 20:1 to 100:1. After incubation, samples were subjected to SDS-PAGE followed by Coomassie Brilliant Blue staining. Gelatin zymography was conducted as described previously (Ogiwara et al., *Proc. Natl. Acad. Sci. USA*, 102:8442-8447 (2005)), except gel was incubated in 20 mM Tris.HCl buffer (pH 7.4) containing 50 mM NaCl and 2 mM CaCl$_2$.

To produce Medaka trypsinogen, two degenerate oligonucleotide PCR primers were synthesized based on the cDNA sequence for conserved regions in serine protease (sense primer: 5'-GT(G/T)(C/G)T(C/G/T)(A/T)C(A/T)GCTGC(C/T)CACTG-3' (SEQ ID NO: 7), which corresponds to the amino acid sequence NH2-Val-Leu-Thr-Ala-Ala-His-Cys-COOH (SEQ ID NO: 8); and antisense primer: 5'-(A/T)GGGCC(A/T)CC(A/T/G)GAGTC(A/T)CC-3' (SEQ ID NO: 9), which corresponds to the amino acid sequence NH2-Gly-Asp-Ser-Gly-Gly-Pro-COOH (SEQ ID NO: 10)). cDNAs were PCR-amplified under the conditions described for EP in the main text. A 435-bp fragment was subcloned into pBluescript (II) KS+ (Stratagene, La Jolla, Calif.) and sequenced.

A 5' portion of Medaka trypsinogen was obtained by the 5'-RACE method (Frohman et al., *Proc. Natl. Acad. Sci. USA*, 85:8998-9002 (1988)) using the 5'-RACE system, Version 2.0 (Invitrogen, Carlsbad, Calif.). The antisense primers used were 5'-AGGAGGTGATGAACTG-3' (SEQ ID NO: 11) (GSP-1; nucleotides 273 to 288, AB272106), 5'-CTCGGT-TCCGTCATTGTTCCGGGAT-3' (SEQ ID NO: 12) (GSP-2; nucleotides 249 to 272, AB272106) and 5'-CCAGACGCAC-CTCCACTCGGGACT-3' (SEQ ID NO: 13) (nested GSP; nucleotides 214 to 237, AB272106). The two rounds of PCR reactions were performed under the conditions of 35 cycles of 0.5 min at 94° C., 0.5 min at 55° C., and 1 min at 72° C. for the first PCR and 35 cycles of 0.5 min at 94° C., 0.5 min at 60° C., and 1 min at 72° C. for the second PCR. The amplified products were then subcloned into pBluescript II plasmid (Stratagene) and sequenced.

A 3' portion of Medaka trypsinogen was obtained by the 3'-RACE method (Frohman et al., *Proc. Natl. Acad. Sci. USA*, 85:8998-9002 (1988)) using the 3'-Full RACE Core Set (Takara, Tokyo, Japan). The sense primers used were 5'-CAT-GATCACCAACTCCATGTTCTG-3' (SEQ ID NO: 14) (RACE1; nucleotides 545 to 568, AB272106) and 5'-TG-GATACCTGGAGGGAGG-3' (SEQ ID NO: 15) (RACE2; nucleotides 572 to 589, AB272106). The two rounds of PCR reactions were performed under the conditions of 35 cycles of 0.5 min at 94° C., 0.5 min at 55° C., and 1 min at 72° C. for the first PCR and 35 cycles of 0.5 min at 94° C., 0.5 min at 57° C., and 1 min at 72° C. for the second PCR. The amplified products were then subcloned into pBluescript II plasmid (Stratagene) and sequenced.

To produce Medaka recombinant trypsinogen, a trypsinogen cDNA fragment (nucleotides 72-755, AB272106) containing its coding sequence, but without the putative signal sequence, was amplified by PCR using the following primers: 5'-CCGGAATTCCTTGACGATGACAAG-3' (SEQ ID NO: 26) and 5'-CCCAAGCTTTCAGTTGCTAGCCATGGT-3' (SEQ ID NO: 27). The PCR product was digested with EcoR I and Hind III, gel-purified and ligated into the pET30a expression vector. The expression of recombinant Medaka trypsinogen in the *Escherichia coli* expression system and its purification with an $Ni^{2+}$-Sepharose column were the same as for the wild-type EP protein described above. The purified recombinant protein was renatured by dialysis against 50 mM Tris.HCl (pH 8.0) and further purified with a column of Resource Q.

These procedures yielded a fusion protein of Medaka trypsinogen that had a vector-derived 52-residue peptide at its N-terminus in addition to the 227-residue sequence of the fish trypsinogen. Thus, this recombinant fusion protein contained two EP-cleavage sites: one from the vector used and the other from trypsinogen itself.

To produce the insertional mutant of the human tissue-type plasminogen activator (tPA), a cDNA (BC007231) coding for human tPA (Pie et al., J. Biol. Chem., 275, 33988-33997 (200)) was first obtained by RT-PCR from a human ovary total RNA (Stratagene) using the primers 5'-CCCAAGCTTATGAAGAGAGGGCTCTGCTGT-3' (SEQ ID NO: 28) (sense-1) and 5'-CTTATCGTCATCATGATGATGATGATG-GTGTCTGGCTCCTCTTCT-3' (SEQ ID NO: 29) (antisense-1).

Using the cDNA as a template, two PCR products were amplified with following primer combinations: sense-1 and antisense-1; and 5'-CACCATCATCATCATCATGATGAC-GACGATAAGTCTTACCAAGTGATC-3' SEQ ID NO: 30) (sense-2) and 5'-CCGCTCGAGTCACGGTCGCATGT-TGTCACGAAT-3' (SEQ ID NO: 31) (antisense-2). Using a mixture of these amplified DNAs as templates, the second PCR was performed with the sense-1 and antisense-2 primer. The PCR products were digested with HindIII and XhoI, then gel-purified and ligated into the pCMV tag4 mammalian expression vector (Stratagene). The resulting mutant was confirmed by DNA sequencing and transfected into CHO cells cultured in F-12 medium (Invitrogen) containing 10% fetal bovine serum (Biological Industries, Beit Haemek, Israel). Transfection was performed using Lipofectamin 2000 (GE Healthcare Biosciences, Uppsala, Sweden). The above procedure produced a fusion protein of human tPA having 11 extra amino acid residues (His-His-His-His-His-His-Asp-Asp-Asp-Asp-Lys (SEQ ID NO: 32): a His-tag sequence followed by an EP-cleavage site) at the N-terminus of mature tPA. This fusion protein secreted from transfected CHO cells was collected from the culture media using an $Ni^{2+}$-Sepharose column. Treatment of the fusion protein with EP proteases generated mature tPA without the 11-residue N-terminal peptide.

Recombinant human kallikrein 8 was prepared as described previously (Rajapakse et al., FEBS Lett., 579:6879-6884 (2005)). Recombinant Medaka gelatinase A was prepared as described previously (Ogiwara et al., Proc. Natl. Acad. Sci. USA, 102:8442-8447 (2005)).

Figure 4B:
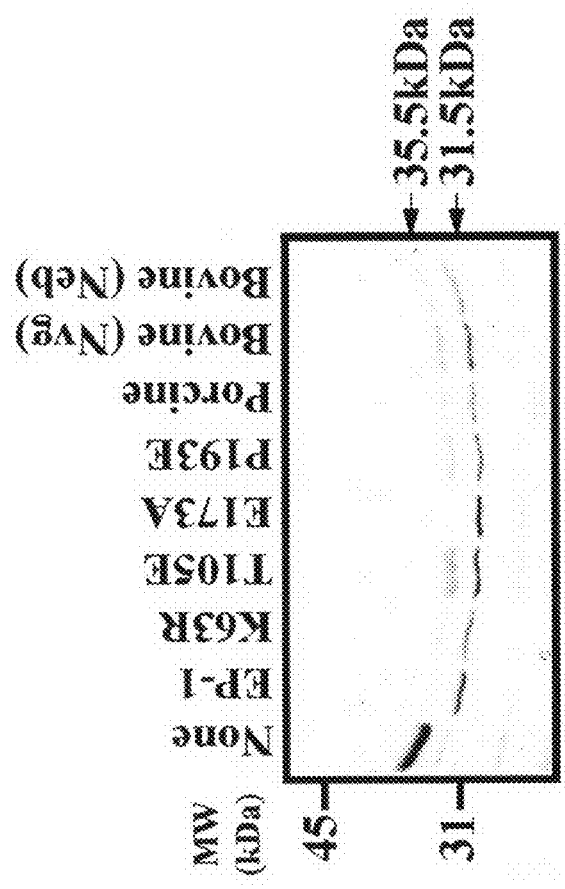
FIG. 4 (A-C) shows the effects of various EP proteases on protein substrates containing a $D_4K$-cleavage site (SEQ ID NO: 1). (A) A recombinant fusion protein of Medaka gelatinase A (5 µg) was separately incubated with active EP proteases (100 ng) at 37° C. for 1 h, and analyzed by SDS-PAGE. (B) A recombinant fusion protein of human kallikrein 8 (hK8) (5 µg) was incubated with active EP proteases (100 ng) at 37° C. for 2 h. After incubation, the samples were analyzed by SDS-PAGE (upper panel), or assayed for activity with Pro-Phe-Arg-MCA (middle panel), or Boc-Glu(OBzl)-Ala-Arg-MCA (lower panel). (C) Culture media collected from two culture dishes (10 cm in diameter) of CHO cells transfected with the pCMV tag4 vector containing the human sctPA sequence were affinity-purified using $Ni^{2+}$-Sepharose, and the resulting eluate was separately treated with active EP proteases (100 ng) at 37° C. for 1 h. The samples were then analyzed by SDS-PAGE/Western blotting using anti-human tPA antibody (upper panel) or anti-His probe antibody (lower panel). The position of sctPA (58- and 61-kDa) detected with the antibodies is shown.
Figure 4A:
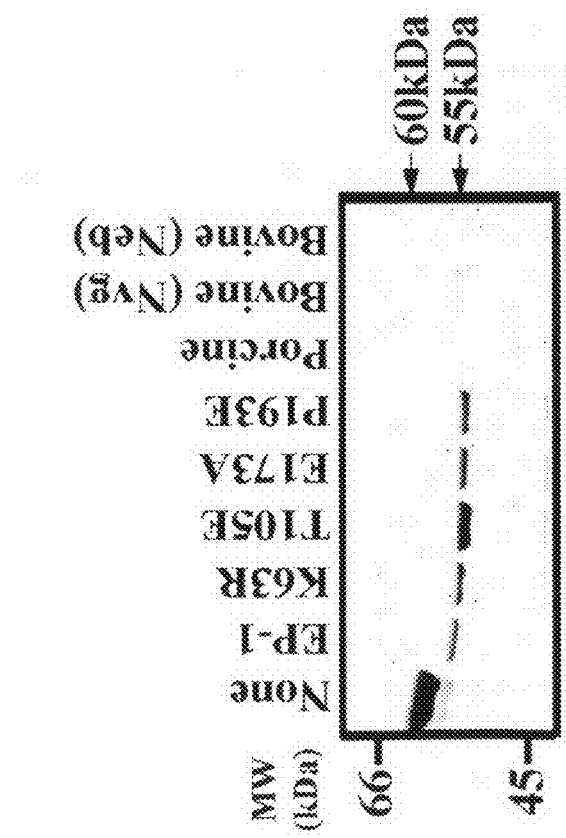

Medaka gelatinase A (Ogiwara et al., Proc. Natl. Acad. Sci. USA, 102:8442-8447 (2005)) was synthesized as a fusion protein containing a His-tag and $D_4K$ sequence (SEQ ID NO: 1 at the N-terminus in the E. coli expression system using the pET30 expression vector. A 60-kDa fusion protein was converted by wild-type or mutant proteases to a 55-kDa protein (FIG. 4A). Under the condition of incubation at the same substrate/protease ratio, the fusion protein was extensively digested by mammalian EP serine proteases.

Next, a 35.5-kDa protein of human kallikrein 8 (hK8) in the same E. coli expression system was synthesized. Digestion with Medaka wild-type and mutant EP proteases generated 31.5-kDa active hK8 by cleaving the $D_4K$ sequence (SEQ ID NO: 1) (FIG. 4B, Top). Under these conditions, the porcine protease extensively degraded the substrate. The EP protease-treated samples were directly assayed for hK8 activity using Pro-Phe-Arg-MCA, a good synthetic peptide substrate of hK8 (Rajapakse et al., FEBS Lett., 579:6879-6884 (2005)). All the samples treated with the Medaka or mammalian EP proteases exhibited Pro-Phe-Arg-MCA-hydrolyzing activity (FIG. 4B, Middle). As expected, none of the Medaka EP proteases (wild-type EP-1, K63R, E173A, or E193A) showed any significant enzyme activity. In contrast, considerable enzyme activities were detected with porcine and bovine (Neb) EP proteases. The fusion protein, which had been digested with the bovine (Nvg) protease, had very low activity, presumably due to inactivation of the EP protease itself during incubation. The substrate Boc-Glu(OBzl)-Ala-Arg-MCA, which is slightly cleaved by active hK8, was rapidly hydrolyzed with the samples treated with mammalian, but not Medaka, EP proteases (FIG. 4B, Bottom).

Enzyme activities were also detected individually with the EP proteases of mammalian origin at a comparable level, indicating that the activities were due to the action of mammalian EP proteases included in the samples. These results demonstrate that the Medaka EP protease used for cleaving the fusion protein has no serious effect on hK8 activity.

Figures 1, 2, 4C, 5A:
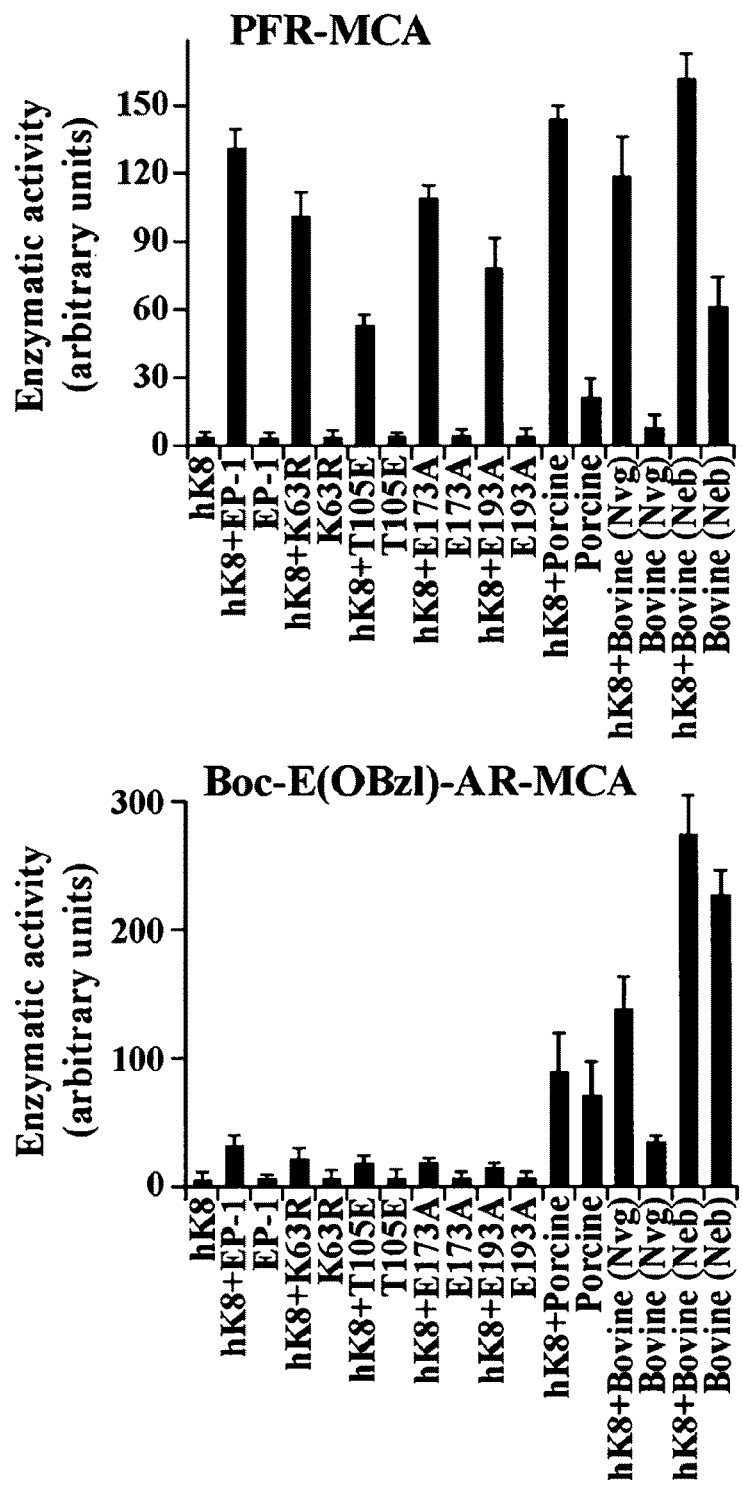

Finally, a human single-chain tPA fusion protein containing an 11-residue sequence of a His-tag/EP-susceptible site at the N-terminus of mature tPA was generated by CHO cells, and used as a substrate for Medaka and mammalian EP proteases. The protein samples treated with the Medaka wild-type or mutant EP proteases, but not with mammalian ones, showed two polypeptides (53- and 55-kDa) detectable with anti-human tPA antibodies (FIG. 4C, Upper). However, the specific antibody for the His-tag sequence did not recognize the polypeptides (FIG. 4C, Lower).

These results indicate that the Medaka proteases properly cleaved the fusion protein at the EP-cleavage site to produce single-chain tPA. These results suggest that the Medaka proteases are more effective than their mammalian counterparts as fusion protein cleavage enzymes for the preparation of desired recombinant proteins.

Taken together, with the exception of medaka EP protease residue position 105 (bovine #98), the residues that were mutated were located at a considerable distance from the enzyme active site. Although mutagenesis had different effects on each of the enzyme activities, one of the mutants, E173A, was interesting in that it showed significantly lower activities than the wild-type enzyme toward all the synthetic substrates tested. In addition, this mutant enzyme still retained a low nonspecific proteolytic activity for protein substrates (HMW kininogen and fibrinogen), with no serious reduction of the D4K (SEQ ID NO: 1) cleaving activity for fusion proteins (gelatinase A, hK8, and tPA). As demonstrated in the present study, the serine protease domain of medaka EP itself has a stricter specificity for almost all of the substrates tested when compared with the mammalian EP protease. Medaka wild-type EP protease would be adequate for the recombinant protein preparation of non-proteolytic enzymes. However, in view of the efficient cleavage at the D4K site (SEQ ID NO: 1) and the minimum nonspecific hydrolysis at the peptide and amide bonds, use of the mutant enzymes, in particular the E173A mutant enzyme, is preferred. The medaka wild-type EP protease and its mutant can be prepared in large quantity in the *E. coli* expression system. Using the medaka EP serine proteases as fusion protein cleavage enzymes, the desired recombinant proteins can be easily and effectively produced.

A number of embodiments of the invention have been described. Nevertheless, it will be understood that various modifications may be made without departing from the spirit and scope of the invention. Accordingly, other embodiments are within the scope of the following claims.

REFERENCES

Light, A. & Janska, H. (1989) Trends Biochem. Sci. 14, 110-112.
Grishan, F. K., Lee, P. C., Lebenthal, E., Johnson, P., Bradley, C. A. & Greene, H. L. (1983) Gastroenterology 85, 727-731.
LaVallie, E. R., Rehemtulla, A., Racie, L. A., DiBlasio, E. A., Ferenz, C., Grant, K. L., Light, A. & McCoy, J. M. (1993) J. Biol. Chem. 268, 23311-13317.
Kitamoto, Y., Yuan, X., Wu, Q., McCourt, D. W. & Sadler, J. E. (1994) Proc. Natl. Acad. Sci. USA 91, 7588-7592.
Kitamoto, Y., Veile, R. A., Donis-Keller, H. & Sadler, J. E. (1995) Biochemistry 34, 4562-4568.
Matsushima, M., Ichinose, M., Yahagi, N., Kakei, K., Tsukada, S., Miki, K., Kurokawa, K., Tashiro, K., Shiokawa, K., Shinomiya, K., et al. (1994) J. Boil. Chem. 269, 19976-19982.
Yahagi, N., Ichinose, M., Matsushima, M., Matsubara, Y., Miki, K., Kurokawa, K., Fukamachi, H., Tashiro, K., Shiokawa, K., Kageyama, T., et al. (1996) Biochem. Biophys. Res. Commun. 219, 806-812.
Yuan, X., Zheng, X., Lu, D., Rubin, D. C., Pung, C. Y. & Sadler, J. E. (1998) Am. J. Physiol. 274, 342-349.
Lu, D., Yuan, X., Zheng. X. & Sadler, J. E. (1997) J. Biol. Chem. 272, 31293-31300.
Mikhailova, A., G. & Rumsh, L., D. (1999) FEBS Lett. 442, 226-230.
Lu, D., Fütterer, K., Korolev, S., Xinglong, Z., Tan, K., Waksman, G. & Sadler, J. E. (1999) J. Mol. Biol. 292, 361-373.
Zheng, X. & Sadler, J., E. (2002) J. Biol. Chem. 277, 6858-6863.
Collins-Racie, L., A., McColgan, J., M., Grant, K., L., DiBlasio-Smith, E., A., McCoy, J., M. & LaVallie, E., R. (1995) Biotechnology 13, 982-987.
Bricteux-Gregoire, S., Schyns, R., & Florkin., M. (1972) Comp. Biochem. Physiol. 42B, 23-39.
Frohman, M. A., Dush, M. K. & Martin, G. R. (1988) Proc. Natl. Acad. Sci. USA 85, 8998-9002.
Ogiwara, K., Takano, N., Shinohara, M., Murakami, M. & Takahashi, T. (2005) Proc. Natl. Acad. Sci. USA 102, 8442-8447.
Chase, T., J., R. & Shaw, E. (1976) Biochem. Biophys. Res. Commun. 29, 508-514.
Barrett, A., J. (1980) Biochem. J. 187, 909-912.
Lineweaver, H. & Bruk, D. (1934) J. Am. Chem. Soc. 56, 658-663.
Rajapakse, S., Ogiwara, K., Takano, N., Moriyama, A. & Takahashi, T. (2005) FEBS Lett. 579, 6879-6884.
Costa F. F. (2005) Gene 357, 83-94.
Rombout, J. H., Stroband, H., W. & Taverne-Thiele, J., J. (1984) Cell Tissue Res. 236, 207-216.
Frohman, M. A., Dush, M. K. & Martin, G. R. (1988) Proc. Natl. Acad. Sci. USA 85, 8998-9002.
Kusakabe, R., Kusakabe, T. & Suzuki, N. (1999) Int. J. Dev. Biol. 43, 541-554.
Kimura, A., Yoshida, I., Takagi, N. & Takahashi, T. (1999) J. Biol. Chem. 274, 24047-24053.
Ogiwara, K., Takano, N., Shinohara, M., Murakami, M. & Takahashi, T. (2005) Proc. Natl. Acad. Sci. USA 102, 8442-8447.
Pennica, D., Holmes, W. E., Kohr, W. J., Harkins, R. N., Vehar, G. A., Ward, C. A., Bennett, W. F., Yelverton, E., Seeburg, P. H., Heyneker, H. L., et. al. (1983) Nature 301, 214-221.
Rajapakse, S., Ogiwara, K., Takano, N., Moriyama, A. & Takahashi, T. (2005) FEBS Lett. 579, 6879-6884.
Pie, D., Kang, T. & Qi, H. (2000) J. Biol. Chem. 275, 33988-33997.

What is claimed is:

1. An isolated nucleic acid molecule comprising
   (a) a nucleic acid molecule encoding the amino acid sequence of SEQ ID NO:4 or a proteolytically active fragment thereof; or
   (b) a nucleic acid molecule encoding a variant of the amino acid sequence of SEQ ID NO:2 wherein the amino acid at an amino acid residue position selected from the group consisting of position 63, position 105, position 144, position 173, and position 193 is mutated, and wherein the amino acid positions are numbered according to the amino acid sequence set forth in SEQ ID NO:65, or a proteolytically active fragment thereof having enteropeptidase activity; or
   (c) a nucleic acid molecule which is the complement of (a) or (b).

2. The isolated nucleic acid molecule of claim 1 which is
   (a) a nucleic acid molecule comprising the nucleotide sequence of SEQ ID NO:5,
   (b) a nucleic acid molecule comprising a variant of the nucleic acid sequence of SEQ ID NO:3, wherein the codon at a codon position corresponding to an amino acid residue position selected from the group consisting of position 63, position 105, position 144, position 173, or position 193, of SEQ ID NO:65 is mutated; or
   (c) a nucleic acid molecule which is the complement of (a) or (b).

3. The isolated nucleic acid molecule of claim 1 or 2 further comprising vector nucleic acid sequences.

4. The nucleic acid molecule of claim 1 or 2 operably linked to a surrogate promoter.

5. The nucleic acid molecule of claim 1 or 2 further comprising nucleic acid sequences encoding a heterologous polypeptide.

6. An isolated host cell which is transformed with the nucleic acid molecule of claim 1 or 2.

7. The isolated host cell of claim 6, wherein the host cell is selected from the group of bacterial cells, fungal cells, and animal cells.

8. The isolated host cell of claim 7, wherein the bacterial cell is an *Escherichia coli* host cell.

9. A method for producing an enteropeptidase selected from the group consisting of:
   a) an enteropeptidase comprising the amino acid sequence of SEQ ID NO:4 or a variant of the amino acid sequence of SEQ ID NO:2 wherein an amino acid at an amino acid residue position selected from the group consisting of position 63, position 105, position 144, position 173, and position 193 is mutated;
   b) an enteropeptidase comprising a proteolytically active fragment of the amino acid sequence of SEQ ID NO:4 or a proteolytically active fragment of a variant of the amino acid sequence of SEQ ID NO:2 wherein an amino acid at an amino acid residue position selected from the group consisting of position 63, position 105, position 144, position 173, and position 193 is mutated; and
   c) an enteropeptidase encoded by the nucleic acid sequence of SEQ ID NO:5 or by a nucleic acid molecule that is a variant of the nucleic acid sequence of SEQ ID NO:3, wherein a codon at a codon position corresponding to an amino acid residue position selected from the group consisting of position 63, position 105, position 144, position 173, or position 193 is mutated;
   said method comprising culturing the host cell of claim 6 under conditions in which the nucleic acid molecule is expressed and the enteropeptidase is produced, and wherein the amino acid residue positions are numbered according to the amino acid sequence set forth in SEQ ID NO:65.

10. The method of claim 9, wherein the enteropeptidase is produced in an *Escherichia coli* host cell.

11. An isolated enteropeptidase selected from the group consisting of:
    (a) an enteropeptidase comprising the amino acid sequence of SEQ ID NO:4;
    (b) a variant of the amino acid sequence of SEQ ID NO:2 wherein the amino acid at an amino acid residue position selected from the group consisting of position 63, position 105, position 144, position 173, and position 193 is mutated; and
    (c) an enteropeptidase comprising a proteolytically active fragment of the amino acid sequence of (a) or (b);
    wherein said isolated enteropeptidase has a proteolytic activity of cleaving the 4-methylcoumaryl-7-amide (MCA)-substrate Boc-Glu(OBzl)-Ala-Arg-MCA and wherein the amino acid residue positions are numbered according to the amino acid sequence set forth in SEQ ID NO:65.

12. The isolated enteropeptidase of claim 11, wherein the mutation is selected from the group consisting of a substitution, deletion, and addition.

13. The isolated enteropeptidase of claim 12, wherein the mutation is a substitution.

14. The isolated enteropeptidase of claim 13, wherein the substitution is at residue position 63.

15. The isolated enteropeptidase of claim 14, wherein the substitution at residue position 63 is K63R, K63A, or K63E.

16. The isolated enteropeptidase of claim 13, wherein the substitution is at residue position 105.

17. The isolated enteropeptidase of claim 16, wherein the substitution at residue position 105 is T105A, T105R, or T105E.

18. The isolated enteropeptidase of claim 13, wherein the substitution is at residue position 144.

19. The isolated enteropeptidase of claim 18, wherein the substitution at residue position 144 is F144S.

20. The isolated enteropeptidase of claim 13, wherein the substitution is at residue position 173.

21. The isolated enteropeptidase of claim 20, wherein the substitution at residue position 173 is E173A.

22. The isolated enteropeptidase of claim 13, wherein the substitution is at residue position 193.

23. The isolated enteropeptidase of claim 22, wherein the substitution at residue position 193 is P193E or P193A.

24. The isolated enteropeptidase of claim 11, comprising the amino acid sequence of SEQ ID NO:4.

25. The isolated enteropeptidase according to claim 11, wherein the enteropeptidase is a recombinant enteropeptidase.

26. The isolated enteropeptidase according to claim 11, wherein the enzyme activity of the enteropeptidase in cleaving a $GD_4K$-βNA substrate has an enhanced stability at 37° C. when incubated at pH 7.4 in 0.2 M NaCl and 2 mM $CaCl_2$ by comparison with the enzyme activity of bovine enteropeptidase in cleaving a $GD_4K$-βNA substrate when incubated at pH 7.4 in 0.2 M NaCl and 2 mM $CaCl_2$.

27. The isolated enteropeptidase according to claim 11, wherein the enteropeptidase is cleavage specific for Asp-Asp-Asp-Asp-Lys (SEQ ID NO:1).

28. The isolated enteropeptidase according to claim 11, wherein the proteolytic activity of said isolated enteropeptidase for a peptide substrate other than SEQ ID NO:1 is less specific than that for the peptide sequence of SEQ ID NO:1.

29. The isolated enteropeptidase of claim 28, wherein the peptide substrate is selected from the group consisting of kininogen, fibrinogen, fibronectin, gelatin and laminin.

30. The isolated enteropeptidase of claim 28, wherein the peptide substrate is a synthetic peptide substrate comprising 4 methylcoumaryl-7-amide (MCA).

31. The isolated enteropeptidase of claim 30, wherein the synthetic peptide substrate is selected from the group consisting of Boc-Glu(OBzl)-Ala-Arg-MCA, Z-Phe-Arg-MCA, and Pro-Phe-Arg-MCA.

32. The isolated enteropeptidase of claim 28, wherein the peptide substrate consists of a fusion protein.

33. The isolated enteropeptidase of claim 32, wherein the fusion protein comprises SEQ ID NO:1 fused to a protein selected from the group consisting of gelatinase A, human kallikrein 8 and tissue type plasminogen activator (tPA).

34. An isolated enteropeptidase comprising a variant of the amino acid sequence of SEQ ID NO:2, wherein the amino acid at an amino acid residue position selected from the group consisting of position 63, position 105, position 144, position 173 and position 193, is mutated, wherein the isolated enteropeptidase variant is cleavage specific for Asp-Asp-Asp-Asp-Lys (SEQ ID NO:1), and has less proteolytic activity for peptide sequences other than that for SEQ ID NO:1, and wherein the amino acid positions are numbered according to the amino acid sequence set forth in SEQ ID NO:65.

35. The isolated enteropeptidase variant according to claim 34, wherein the mutation is a substitution selected from the group consisting of K63R, K63A, K63E, T105A, T105R, T105E, F144S, E173A, P193A, and P193A.

36. The isolated enteropeptidase variant according to claim 35, wherein the mutation is E173A.

37. An isolated enteropeptidase comprising the amino acid sequence of SEQ ID NO:4, wherein the isolated enteropeptidase is cleavage specific for Asp-Asp-Asp-Asp-Lys (SEQ ID NO:1), and has less proteolytic activity for peptide sequences other than that for SEQ ID NO:1.

38. A method for cleaving a protein containing an Asp-Asp-Asp-Asp-Lys cleavage site (SEQ ID NO:1) with the enteropeptidase of claim 11, the method comprising:

contacting the protein with the enteropeptidase; wherein the contacting of the protein with the enteropeptidase results in specific cleavage, at the cleavage site of Asp-Asp-Asp-Asp-Lys (SEQ ID NO:1).

39. The method of claim 38, wherein the protein is a fusion protein.

40. The method of claim 39, wherein the fusion protein is recombinantly produced by an isolated host cell.

41. The method of claim 38, wherein the protein is recombinantly produced by a bacterial host cell.

42. A method for preparing a recombinant protein by cleavage with an enteropeptidase of claim 11, the method comprising:

providing a recombinant fusion protein comprising a Asp-Asp-Asp-Asp-Lys cleavage site (SEQ ID NO:1) fused to said recombinant fusion protein; and contacting the fusion protein with the enteropeptidase;

wherein contacting the recombinant fusion protein with the enteropeptidase results in a specific cleavage at the Asp-Asp-Asp-Asp-Lys cleavage site (SEQ ID NO:1) and the preparation of the recombinant protein.

43. A kit comprising the enteropeptidase of claim 11 and instructions for use in cleaving a protein comprising an Asp-Asp-Asp-Asp-Lys cleavage site (SEQ ID NO:1).

44. The kit of claim 43, wherein the protein is a fusion protein.

45. The kit of claim 44, wherein the fusion protein is recombinantly produced by an isolated host cell.

46. The kit of claim 43, wherein the protein is recombinantly produced by a bacterial host cell.

47. The kit of claim 43, wherein the protein is a synthetic protein.

48. The isolated enteropeptidase of claim 11, wherein the enteropeptidase activity of said isolated enteropeptidase is less than 34 $mM^{-1}$ $min^{-1}$ $k_{cat}/K_m$ using Boc-Glu(OBzl)-Ala-Arg-MCA as a substrate.

* * * * *